US011807670B2

(12) United States Patent
Chan et al.

(10) Patent No.: US 11,807,670 B2
(45) Date of Patent: Nov. 7, 2023

(54) FUSION PROTEINS WITH IMPROVED PROPERTIES

(71) Applicant: The Chinese University of Hong Kong, Hong Kong (CN)

(72) Inventors: Michael Chan, Hong Kong (CN); Marianne Lee, Hong Kong (CN); Bradley Heater, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/323,215

(22) PCT Filed: Jul. 10, 2017

(86) PCT No.: PCT/CN2017/092393
§ 371 (c)(1),
(2) Date: Feb. 4, 2019

(87) PCT Pub. No.: WO2018/028371
PCT Pub. Date: Feb. 15, 2018

(65) Prior Publication Data

US 2019/0185522 A1 Jun. 20, 2019

Related U.S. Application Data

(60) Provisional application No. 62/373,072, filed on Aug. 10, 2016.

(51) Int. Cl.
| | |
|---|---|
| *C07K 14/325* | (2006.01) |
| *C12N 9/96* | (2006.01) |
| *C12N 11/02* | (2006.01) |
| *C07K 19/00* | (2006.01) |
| *C12N 15/62* | (2006.01) |
| *C12N 9/00* | (2006.01) |
| *C12N 9/24* | (2006.01) |
| *C12N 9/48* | (2006.01) |
| *C12N 9/14* | (2006.01) |
| *C12N 9/20* | (2006.01) |
| *C12P 7/64* | (2022.01) |

(52) U.S. Cl.
CPC ........... *C07K 14/325* (2013.01); *C07K 19/00* (2013.01); *C12N 9/14* (2013.01); *C12N 9/20* (2013.01); *C12N 9/2402* (2013.01); *C12N 9/48* (2013.01); *C12N 9/93* (2013.01); *C12N 9/96* (2013.01); *C12N 11/02* (2013.01); *C12N 15/62* (2013.01); *C12P 7/64* (2013.01)

(58) Field of Classification Search
None
See application file for complete search history.

(56) References Cited

U.S. PATENT DOCUMENTS 5,306,628 A 4/1994 Sivasubramanian et al.

FOREIGN PATENT DOCUMENTS

| | | | | |
|---|---|---|---|---|
| CN | 102276728 A | 12/2011 | | |
| WO | 2012158555 A2 | 11/2012 | | |
| WO | WO-2013085540 A2 * | 6/2013 | .......... | C12N 9/2462 |

OTHER PUBLICATIONS

Homaei AA et al. Enzyme immobilization: an update. 2013. Journal of Chemical Biology. 6:185-205. (Year: 2013).*
GenBank Cry3Aa protein; Q9S6N9. p. 1. 2006.*
Borrelli GM et al. Recombinant Lipases and Phospholipases and Their Use as Biocatalysts for Industrial Applications. 2015. Int. J. Mol. Sci. 16, 20774-20840. (Year: 2015).*
Sekhon SS et al. Immobilization of para-nitrobenzyl esterase-CLEA on electrospun polymer nanofibers for potential use in the synthesis of cephalosporin-derived antibiotics. 2014. Mol. Cell Toxicol. 10:215-221. (Year: 2014).*
Feng, et al. "Research progress on crystallized proteins and its impact factors _. " Journal of Anhui Agricultural Sciences (2010).
Guo, et al. "Bacillus thuringiensis Cry3Aa fused to a cellulase-binding peptide shows increased toxicity against the longhorned beetle." Applied microbiology and biotechnology 93, No. 3 (2012): 1249-1256.
Nair, et al. "Cry Protein Crystals: A Novel Platform for Protein Delivery." PloS one 10, No. 6 (2015): e0127669.
International Search Report in PCT/CN2017/092393, dated Sep. 28, 2017.

* cited by examiner

*Primary Examiner* — Paul J Holland
(74) *Attorney, Agent, or Firm* — Kilpatrick Townsend and Stockton LLP

(57) ABSTRACT

It provides novel fusion proteins that are capable of self-crystallization and exhibit improved physical properties such as enhanced tolerance to organic solvents and increased thermostability. Polynucleotides encoding the fusion proteins as well as methods of making and using such fusion proteins are also described.

12 Claims, 45 Drawing Sheets

Specification includes a Sequence Listing.

Table 1 List of mutations in engineered Dieselzymes

| Construct | Mutations present |
|---|---|
| Dieselzyme 1 | G181C/S238C* |
| Dieselzyme 2 | G181C/S238C/K208N/L64I/A70T/F225L/Q277L |
| Dieselzyme 3 | G181C/S238C/K208N/L64I/A70T/F225L/Q277L/G202E/G266S/D270N/N17S# |
| Dieselzyme 4 | G181C/S238C/K208N/L64I/A70T/F225L/Q277L/G202E/G266S/D270N/N17S/I255F/R33T |

| Construct | Details |
| --- | --- |
| Cry3A-lipA | LipA fused to full length Cry3A |
| Cry3A(1-626)-lipA | C-terminal 18 amino acid residues removed and incorporation of a flexible linker |
| Cry3A(1-301)-lipA-Cry3A(495-644) | LipA sandwiched between domain I and domain III of Cry3A |
| Cry3A(1-290)-lipA | LipA fused to domain I of Cry3A |
| Cry3A(498-644)-lipA | LipA fused to domain III of Cry3A |

SEQUENCE LISTING

```
<160> NUMBER OF SEQ ID NOS: 9

<210> SEQ ID NO 1
<211> LENGTH: 1183
<212> TYPE: PRT
<213> ORGANISM: Bacillus thuringiensis

<400> SEQUENCE: 1

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60
```

```
Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Val Thr Gln Ile Pro Leu Thr Lys Ser Thr Asn
465                 470                 475                 480
```

```
Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
            530                 535                 540

Ile Asn Gln Gly Asn Phe Ser Ala Thr Met Cys Ser Gly Ser Asn Leu
545                 550                 555                 560

Gln Ser Gly Ser Phe Arg Thr Val Gly Phe Thr Thr Pro Phe Asn Phe
                565                 570                 575

Pro Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
                595                 600                 605

Thr Phe Glu Ala Glu Tyr Asp Leu Glu Arg Ala Gln Lys Ala Val Asn
            610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
                660                 665                 670

Ala Lys Arg Leu Ser Asp Glu Arg Asn Leu Leu Gln Asp Pro Asn Phe
            675                 680                 685

Arg Gly Ile Asn Arg Gln Leu Asp Arg Gly Trp Arg Gly Ser Thr Asp
            690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
            770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
            805                 810                 815

Glu Gly Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895
```

-continued

Asn Ile Val Tyr Lys Glu Ala Lys Glu Ser Val Asp Ala Leu Phe Val
                900                 905                 910

Asn Ser Gln Tyr Asp Arg Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln Asn Asn His Arg Ser Val Leu Val
        995                 1000                1005

Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly
    1025                1030                1035

Tyr Gly Glu Gly Cys Val Thr Ile His Glu Ile Glu Asn Asn Thr
    1040                1045                1050

Asp Glu Leu Lys Phe Ser Asn Cys Val Glu Glu Val Tyr Pro
    1055                1060                1065

Asn Asn Thr Val Thr Cys Asn Asp Tyr Thr Ala Thr Gln Glu Glu
    1070                1075                1080

Tyr Glu Gly Thr Tyr Thr Ser Arg Asn Arg Gly Tyr Asp Gly Ala
    1085                1090                1095

Tyr Glu Ser Asn Ser Ser Val Pro Ala Asp Tyr Ala Ser Ala Tyr
    1100                1105                1110

Glu Glu Lys Ala Tyr Thr Asp Gly Arg Arg Asp Asn Pro Cys Glu
    1115                1120                1125

Ser Asn Arg Gly Tyr Gly Asp Tyr Thr Pro Leu Pro Ala Gly Tyr
    1130                1135                1140

Val Thr Lys Glu Leu Glu Tyr Phe Pro Glu Thr Asp Lys Val Trp
    1145                1150                1155

Ile Glu Ile Gly Glu Thr Glu Gly Thr Phe Ile Val Asp Ser Val
    1160                1165                1170

Glu Leu Leu Leu Met Glu Glu Val Asp Ala
    1175                1180

<210> SEQ ID NO 2
<211> LENGTH: 1155
<212> TYPE: PRT
<213> ORGANISM: Bacillus thuringiensis

<400> SEQUENCE: 2

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

```
Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
            290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
            370                 375                 380

Glu Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495
```

```
Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
                595                 600                 605

Val Thr Phe Glu Ala Glu Tyr Asp Leu Glu Arg Ala Gln Lys Ala Val
            610                 615                 620

Asn Glu Leu Phe Thr Ser Phe Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
            690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
            835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Pro Ala Asp Lys Arg Val His Ser
            900                 905                 910
```

Ile Arg Glu Ala Tyr Leu Pro Glu Leu Ser Val Ile Pro Gly Val Asn
            915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
            965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
            995                 1000                1005

Ala Tyr Lys Glu Gly Tyr Gly Glu Gly Cys Val Thr Ile His Glu
        1010                1015                1020

Ile Glu Asn Asn Thr Asp Glu Leu Lys Phe Ser Asn Cys Val Glu
        1025                1030                1035

Glu Glu Val Tyr Pro Asn Asn Thr Val Thr Cys Asn Asp Tyr Thr
        1040                1045                1050

Ala Thr Gln Glu Glu Tyr Glu Gly Thr Tyr Thr Ser Arg Asn Arg
        1055                1060                1065

Gly Tyr Asp Gly Ala Tyr Glu Ser Asn Ser Ser Val Pro Ala Asp
        1070                1075                1080

Tyr Ala Ser Ala Tyr Glu Glu Lys Ala Tyr Thr Asp Gly Arg Arg
        1085                1090                1095

Asp Asn Pro Cys Glu Ser Asn Arg Gly Tyr Gly Asp Tyr Thr Pro
        1100                1105                1110

Leu Pro Ala Gly Tyr Val Thr Lys Glu Leu Glu Tyr Phe Pro Glu
        1115                1120                1125

Thr Asp Lys Val Trp Ile Glu Ile Gly Glu Thr Glu Gly Thr Phe
        1130                1135                1140

Ile Val Asp Ser Val Glu Leu Leu Leu Met Lys Glu
        1145                1150                1155

<210> SEQ ID NO 3
<211> LENGTH: 633
<212> TYPE: PRT
<213> ORGANISM: Bacillus thuringiensis

<400> SEQUENCE: 3

Met Asn Val Leu Asn Ser Gly Arg Thr Thr Ile Cys Asp Ala Tyr
1               5                   10                  15

Asn Val Val Ala His Asp Pro Phe Ser Phe Glu His Lys Ser Leu Asp
                20                  25                  30

Thr Ile Gln Lys Glu Trp Met Glu Trp Lys Arg Thr Asp His Ser Leu
            35                  40                  45

Tyr Val Ala Pro Val Val Gly Thr Val Ser Ser Phe Leu Leu Lys Lys
        50                  55                  60

Val Gly Ser Leu Ile Gly Lys Arg Ile Leu Ser Glu Leu Trp Gly Ile
65              70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
        115                 120                 125

-continued

```
Gln Gln Val Asp Asn Phe Leu Asn Pro Thr Gln Asn Pro Val Pro Leu
130                 135                 140
Ser Ile Thr Ser Ser Val Asn Thr Met Gln Gln Leu Phe Leu Asn Arg
145                 150                 155                 160
Leu Pro Gln Phe Gln Ile Gln Gly Tyr Gln Leu Leu Leu Pro Leu
                165                 170                 175
Phe Ala Gln Ala Ala Asn Met His Leu Ser Phe Ile Arg Asp Val Ile
                180                 185                 190
Leu Asn Ala Asp Glu Trp Gly Ile Ser Ala Ala Thr Leu Arg Thr Tyr
                195                 200                 205
Arg Asp Tyr Leu Arg Asn Tyr Thr Arg Asp Tyr Ser Asn Tyr Cys Ile
210                 215                 220
Asn Thr Tyr Gln Thr Ala Phe Arg Gly Leu Asn Thr Arg Leu His Asp
225                 230                 235                 240
Met Leu Glu Phe Arg Thr Tyr Met Phe Leu Asn Val Phe Glu Tyr Val
                245                 250                 255
Ser Ile Trp Ser Leu Phe Lys Tyr Gln Ser Leu Met Val Ser Ser Gly
                260                 265                 270
Ala Asn Leu Tyr Ala Ser Gly Ser Gly Pro Gln Gln Thr Gln Ser Phe
                275                 280                 285
Thr Ala Gln Asn Trp Pro Phe Leu Tyr Ser Leu Phe Gln Val Asn Ser
                290                 295                 300
Asn Tyr Ile Leu Ser Gly Ile Ser Gly Thr Arg Leu Ser Ile Thr Phe
305                 310                 315                 320
Pro Asn Ile Gly Gly Leu Pro Gly Ser Thr Thr Thr His Ser Leu Asn
                325                 330                 335
Ser Ala Arg Val Asn Tyr Ser Gly Gly Val Ser Ser Gly Leu Ile Gly
                340                 345                 350
Ala Thr Asn Leu Asn His Asn Phe Asn Cys Ser Thr Val Leu Pro Pro
                355                 360                 365
Leu Ser Thr Pro Phe Val Arg Ser Trp Leu Asp Ser Gly Thr Asp Arg
370                 375                 380
Glu Gly Val Ala Thr Ser Thr Asn Trp Gln Thr Glu Ser Phe Gln Thr
385                 390                 395                 400
Thr Leu Ser Leu Arg Cys Gly Ala Phe Ser Ala Arg Gly Asn Ser Asn
                405                 410                 415
Tyr Phe Pro Asp Tyr Phe Ile Arg Asn Ile Ser Gly Val Pro Leu Val
                420                 425                 430
Ile Arg Asn Glu Asp Leu Thr Arg Pro Leu His Tyr Asn Gln Ile Arg
                435                 440                 445
Asn Ile Glu Ser Pro Ser Gly Thr Pro Gly Gly Ala Arg Ala Tyr Leu
                450                 455                 460
Val Ser Val His Asn Arg Lys Asn Asn Ile Tyr Ala Ala Asn Glu Asn
465                 470                 475                 480
Gly Thr Met Ile His Leu Ala Pro Glu Asp Tyr Thr Gly Phe Thr Ile
                485                 490                 495
Ser Pro Ile His Ala Thr Gln Val Asn Asn Gln Thr Arg Thr Phe Ile
                500                 505                 510
Ser Glu Lys Phe Gly Asn Gln Gly Asp Ser Leu Arg Phe Glu Gln Ser
                515                 520                 525
Asn Thr Thr Ala Arg Tyr Thr Leu Arg Gly Asn Gly Asn Ser Tyr Asn
530                 535                 540
```

```
Leu Tyr Leu Arg Val Ser Ser Ile Gly Asn Ser Thr Ile Arg Val Thr
545                 550                 555                 560

Ile Asn Gly Arg Val Tyr Thr Val Ser Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Ile Val Ala Ser Asp Asn Thr Asn Val Thr Leu Asp Ile Asn
        595                 600                 605

Val Thr Leu Asn Ser Gly Thr Pro Phe Asp Leu Met Asn Ile Met Phe
    610                 615                 620

Val Pro Thr Asn Leu Pro Pro Leu Tyr
625                 630
```

<210> SEQ ID NO 4
<211> LENGTH: 652
<212> TYPE: PRT
<213> ORGANISM: Bacillus thuringiensis

<400> SEQUENCE: 4

```
Met Ile Arg Lys Gly Gly Arg Lys Met Asn Pro Asn Asn Arg Ser Glu
1               5                   10                  15

His Asp Thr Ile Lys Thr Glu Asn Asn Glu Val Pro Thr Asn His
            20                  25                  30

Val Gln Tyr Pro Leu Ala Glu Thr Pro Asn Pro Thr Leu Glu Asp Leu
        35                  40                  45

Asn Tyr Lys Glu Phe Leu Arg Met Thr Ala Asp Asn Asn Thr Glu Ala
    50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
            100                 105                 110

Pro Trp Lys Ala Phe Met Glu Gln Val Glu Ala Leu Met Asp Gln Lys
        115                 120                 125

Ile Ala Asp Tyr Ala Lys Asn Lys Ala Leu Ala Glu Leu Gln Gly Leu
    130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu
                165                 170                 175

Leu Phe Ser Gln Ala Glu Ser His Phe Arg Asn Ser Met Pro Ser Phe
            180                 185                 190

Ala Ile Ser Gly Tyr Glu Val Leu Phe Leu Thr Thr Tyr Ala Gln Ala
        195                 200                 205

Ala Asn Thr His Leu Phe Leu Leu Lys Asp Ala Gln Ile Tyr Gly Glu
    210                 215                 220

Glu Trp Gly Tyr Glu Lys Glu Asp Ile Ala Glu Phe Tyr Lys Arg Gln
225                 230                 235                 240

Leu Lys Leu Thr Gln Glu Tyr Thr Asp His Cys Val Lys Trp Tyr Asn
                245                 250                 255

Val Gly Leu Asp Lys Leu Arg Gly Ser Ser Tyr Glu Ser Trp Val Asn
            260                 265                 270

Phe Asn Arg Tyr Arg Arg Glu Met Thr Leu Thr Val Leu Asp Leu Ile
        275                 280                 285
```

```
Ala Leu Phe Pro Leu Tyr Asp Val Arg Leu Tyr Pro Lys Glu Val Lys
290                 295                 300

Thr Glu Leu Thr Arg Asp Val Leu Thr Asp Pro Ile Val Gly Val Asn
305                 310                 315                 320

Asn Leu Arg Gly Tyr Gly Thr Thr Phe Ser Asn Ile Glu Asn Tyr Ile
                325                 330                 335

Arg Lys Pro His Leu Phe Asp Tyr Leu His Arg Ile Gln Phe His Thr
            340                 345                 350

Arg Phe Gln Pro Gly Tyr Tyr Gly Asn Asp Ser Phe Asn Tyr Trp Ser
        355                 360                 365

Gly Asn Tyr Val Ser Thr Arg Pro Ser Ile Gly Ser Asn Asp Ile Ile
370                 375                 380

Thr Ser Pro Phe Tyr Gly Asn Lys Ser Ser Glu Pro Val Gln Asn Leu
385                 390                 395                 400

Glu Phe Asn Gly Glu Lys Val Tyr Arg Ala Val Ala Asn Thr Asn Leu
                405                 410                 415

Ala Val Trp Pro Ser Ala Val Tyr Ser Gly Val Thr Lys Val Glu Phe
            420                 425                 430

Ser Gln Tyr Asn Asp Gln Thr Asp Glu Ala Ser Thr Gln Thr Tyr Asp
        435                 440                 445

Ser Lys Arg Asn Val Gly Ala Val Ser Trp Asp Ser Ile Asp Gln Leu
450                 455                 460

Pro Pro Glu Thr Thr Asp Glu Pro Leu Glu Lys Gly Tyr Ser His Gln
465                 470                 475                 480

Leu Asn Tyr Val Met Cys Phe Leu Met Gln Gly Ser Arg Gly Thr Ile
                485                 490                 495

Pro Val Leu Thr Trp Thr His Lys Ser Val Asp Phe Phe Asn Met Ile
            500                 505                 510

Asp Ser Lys Lys Ile Thr Gln Leu Pro Leu Val Lys Ala Tyr Lys Leu
        515                 520                 525

Gln Ser Gly Ala Ser Val Val Ala Gly Pro Arg Phe Thr Gly Gly Asp
530                 535                 540

Ile Ile Gln Cys Thr Glu Asn Gly Ser Ala Ala Thr Ile Tyr Val Thr
545                 550                 555                 560

Pro Asp Val Ser Tyr Ser Gln Lys Tyr Arg Ala Arg Ile His Tyr Ala
                565                 570                 575

Ser Thr Ser Gln Ile Thr Phe Thr Leu Ser Leu Asp Gly Ala Pro Phe
            580                 585                 590

Asn Gln Tyr Tyr Phe Asp Lys Thr Ile Asn Lys Gly Asp Thr Leu Thr
        595                 600                 605

Tyr Asn Ser Phe Asn Leu Ala Ser Phe Ser Thr Pro Phe Glu Leu Ser
610                 615                 620

Gly Asn Asn Leu Gln Ile Gly Val Thr Gly Leu Ser Ala Gly Asp Lys
625                 630                 635                 640

Val Tyr Ile Asp Lys Ile Glu Phe Ile Pro Val Asn
                645                 650

<210> SEQ ID NO 5
<211> LENGTH: 1180
<212> TYPE: PRT
<213> ORGANISM: Bacillus thuringiensis
```

<400> SEQUENCE: 5

```
Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
        35                  40                  45

Asn Met Cys Gln Gln Asn Gln Gln Tyr Gly Gly Asp Phe Glu Thr Phe
    50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
        115                 120                 125

Ile Ala Ser Thr Tyr Ile Ser Asn Ala Asn Lys Ile Leu Asn Arg Ser
    130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
            180                 185                 190

Pro Pro Asn Pro Ser Asp Cys Asp Tyr Tyr Asn Ile Leu Val Leu Ser
        195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
            260                 265                 270

Asn Leu Ile Lys Thr Thr Pro Asp Ser Asn Leu Asp Gly Asn Ile Asn
        275                 280                 285

Trp Asn Thr Tyr Asn Thr Tyr Arg Thr Lys Met Thr Thr Ala Val Leu
    290                 295                 300

Asp Leu Val Ala Leu Phe Pro Asn Tyr Asp Val Gly Lys Tyr Pro Ile
305                 310                 315                 320

Gly Val Gln Ser Glu Leu Thr Arg Glu Ile Tyr Gln Val Leu Asn Phe
                325                 330                 335

Glu Glu Ser Pro Tyr Lys Tyr Tyr Asp Phe Gln Tyr Gln Glu Asp Ser
            340                 345                 350

Leu Thr Arg Arg Pro His Leu Phe Thr Trp Leu Asp Ser Leu Asn Phe
        355                 360                 365

Tyr Glu Lys Ala Gln Thr Thr Pro Asn Asn Phe Phe Thr Ser His Tyr
    370                 375                 380

Asn Met Phe His Tyr Thr Leu Asp Asn Ile Ser Gln Lys Ser Ser Val
385                 390                 395                 400

Phe Gly Asn His Asn Val Thr Asp Lys Leu Lys Ser Leu Gly Leu Ala
                405                 410                 415
```

```
Thr Asn Ile Tyr Ile Phe Leu Leu Asn Val Ile Ser Leu Asp Asn Lys
            420                 425                 430

Tyr Leu Asn Asp Tyr Asn Asn Ile Ser Lys Met Asp Phe Phe Ile Thr
            435                 440                 445

Asn Gly Thr Arg Leu Leu Glu Lys Glu Leu Thr Ala Gly Ser Gly Gln
            450                 455                 460

Ile Thr Tyr Asp Val Asn Lys Asn Ile Phe Gly Leu Pro Ile Leu Lys
465                 470                 475                 480

Arg Arg Glu Asn Gln Gly Asn Pro Thr Leu Phe Pro Thr Tyr Asp Asn
                    485                 490                 495

Tyr Ser His Ile Leu Ser Phe Ile Lys Ser Leu Ser Ile Pro Ala Thr
            500                 505                 510

Tyr Lys Thr Gln Val Tyr Thr Phe Ala Trp Thr His Ser Ser Val Asp
            515                 520                 525

Pro Lys Asn Thr Ile Tyr Thr His Leu Thr Thr Gln Ile Pro Ala Val
            530                 535                 540

Lys Ala Asn Ser Leu Gly Thr Ala Ser Lys Val Val Gln Gly Pro Gly
545                 550                 555                 560

His Thr Gly Gly Asp Leu Ile Asp Phe Lys Asp His Phe Lys Ile Thr
                    565                 570                 575

Cys Gln His Ser Asn Phe Gln Gln Ser Tyr Phe Ile Arg Ile Arg Tyr
            580                 585                 590

Ala Ser Asn Gly Ser Ala Asn Thr Arg Ala Val Ile Asn Leu Ser Ile
            595                 600                 605

Pro Gly Val Ala Glu Leu Gly Met Ala Leu Asn Pro Thr Phe Ser Gly
610                 615                 620

Thr Asp Tyr Thr Asn Leu Lys Tyr Lys Asp Phe Gln Tyr Leu Glu Phe
625                 630                 635                 640

Ser Asn Glu Val Lys Phe Ala Pro Asn Gln Asn Ile Ser Leu Val Phe
                    645                 650                 655

Asn Arg Ser Asp Val Tyr Thr Asn Thr Thr Val Leu Ile Asp Lys Ile
                    660                 665                 670

Glu Phe Leu Pro Ile Thr Arg Ser Ile Arg Glu Asp Arg Glu Lys Gln
            675                 680                 685

Lys Leu Glu Thr Val Gln Gln Ile Ile Asn Thr Phe Tyr Ala Asn Pro
            690                 695                 700

Ile Lys Asn Thr Leu Gln Ser Glu Leu Thr Asp Tyr Asp Ile Asp Gln
705                 710                 715                 720

Ala Ala Asn Leu Val Glu Cys Ile Ser Glu Glu Leu Tyr Pro Lys Glu
                    725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
            770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
                    805                 810                 815

Pro Tyr Thr Arg Tyr Leu Val Arg Gly Phe Val Gly Ser Ser Lys Asp
            820                 825                 830
```

```
Val Glu Leu Val Val Ser Arg Tyr Gly Glu Ile Asp Ala Ile Met
    835                 840                 845

Asn Val Pro Ala Asp Leu Asn Tyr Leu Tyr Pro Ser Thr Phe Asp Cys
850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
                885                 890                 895

His Val Val Cys Gln Asp Ser His Gln Phe Ser Phe Thr Ile Asp Thr
                900                 905                 910

Gly Ala Leu Asp Thr Asn Glu Asn Ile Gly Val Trp Val Met Phe Lys
                915                 920                 925

Ile Ser Ser Pro Asp Gly Tyr Ala Ser Leu Asp Asn Leu Glu Val Ile
    930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
                965                 970                 975

Gln Ala Tyr Asp Val Ala Lys Gln Ala Ile Asp Ala Leu Phe Thr Asn
                980                 985                 990

Val Gln Asp Glu Ala Leu Gln Phe Asp Thr Thr Leu Ala Gln Ile Gln
                995                 1000                1005

Tyr Ala Glu Tyr Leu Val Gln Ser Ile Pro Tyr Val Tyr Asn Asp
    1010                1015                1020

Trp Leu Ser Asp Val Pro Gly Met Asn Tyr Asp Ile Tyr Val Glu
    1025                1030                1035

Leu Asp Ala Arg Val Ala Gln Ala Arg Tyr Leu Tyr Asp Thr Arg
    1040                1045                1050

Asn Ile Ile Lys Asn Gly Asp Phe Thr Gln Gly Val Met Gly Trp
    1055                1060                1065

His Val Thr Gly Asn Ala Asp Val Gln Gln Ile Asp Gly Val Ser
    1070                1075                1080

Val Leu Val Leu Ser Asn Trp Ser Ala Gly Val Ser Gln Asn Val
    1085                1090                1095

His Leu Gln His Asn His Gly Tyr Val Leu Arg Val Ile Ala Lys
    1100                1105                1110

Lys Glu Gly Pro Gly Asn Gly Tyr Val Thr Leu Met Asp Cys Glu
    1115                1120                1125

Glu Asn Gln Glu Lys Leu Thr Phe Thr Ser Cys Glu Glu Gly Tyr
    1130                1135                1140

Ile Thr Lys Thr Val Asp Val Phe Pro Asp Thr Asp Arg Val Arg
    1145                1150                1155

Ile Glu Ile Gly Glu Thr Glu Gly Ser Phe Tyr Ile Glu Ser Ile
    1160                1165                1170

Glu Leu Ile Cys Met Asn Glu
    1175                1180

<210> SEQ ID NO 6
<211> LENGTH: 686
<212> TYPE: PRT
<213> ORGANISM: Bacillus thuringiensis
```

<400> SEQUENCE: 6

```
Met Asn Ser Tyr Gln Asn Lys Asn Glu Tyr Glu Ile Leu Asn Ala Pro
1               5                   10                  15

Ser Asn Asn Thr Asn Met Pro Asn Arg Tyr Pro Phe Ala Asn Asp Pro
            20                  25                  30

Asn Ala Met Met Lys Asn Gly Asn Tyr Lys Asp Trp Leu Asp Ile Cys
        35                  40                  45

Asn Pro Glu Tyr Arg Tyr Ser Asn Pro Glu Ala Tyr Arg Asn Thr Lys
    50                  55                  60

Ala Ala Met Ser Phe Gly Val Gly Leu Val Ser Thr Ile Leu Gly Val
65                  70                  75                  80

Leu Gly Gly Pro Ile Ser Val Thr Leu Gly Ala Ile Ile Gly Val Val
                85                  90                  95

Thr Ala Val Leu Glu Phe Ile Pro Ala Asp Tyr Asp Asn Thr Lys
            100                 105                 110

Glu Thr Trp Gly Val Leu Ile Ala Ala Ile Lys Glu Leu Ile Tyr Glu
            115                 120                 125

Glu Ile Lys Gly Glu Ala Met Asn Ala Ala Lys Ala Lys Leu Asp Gly
    130                 135                 140

Leu Tyr Lys Val Met Lys Asn Tyr Asp Asn Lys Leu Asn Val Trp Lys
145                 150                 155                 160

Asn Gly Asp Lys Ser Pro Val Glu Gln Asn Glu Ile Gln Arg Val Phe
                165                 170                 175

Ala Asp Thr Asn Asn Ser Phe Leu Leu Leu Ile Ser Gln Phe Gln Gln
            180                 185                 190

Leu Gly His Glu Val Ser Phe Leu Pro Leu Phe Ala Val Ala Ala Asn
    195                 200                 205

Phe His Leu Leu Leu Leu Arg Asp Val Ser Ile Tyr Gly Lys Glu Trp
210                 215                 220

Gly Tyr Thr Asn Asn Ile Ile Glu Gly Tyr His Ser Asp Gln Leu Asp
225                 230                 235                 240

Met Thr Gln Asp Tyr Thr Asn Tyr Ala Val Asp Thr Tyr Asn Lys Gly
                245                 250                 255

Leu Glu Glu Ala Lys Lys Ile Lys Asn Ser Asp Lys Leu Asp Trp Asp
            260                 265                 270

Phe Tyr Asn Gln Tyr Arg Arg Asp Met Thr Leu Thr Val Leu Asp Val
    275                 280                 285

Ile Ala Leu Phe Pro Thr Tyr Asp Val Arg Lys Tyr Pro Ile Ser Thr
290                 295                 300

Lys Val Glu Leu Thr Arg Glu Ile Tyr Thr Asp Met Ile Asn Tyr Ile
305                 310                 315                 320

Asn Asn Pro Phe Met Thr Asn Pro Val Glu Gly Gln Arg Phe Ala Gly
                325                 330                 335

Tyr Thr Val Ala Gln Phe Asn Ser Ile Glu Asn Ala Leu Thr Arg Glu
            340                 345                 350

Pro His Leu Phe Thr Trp Leu Lys Glu Val Thr Gly Tyr Phe Tyr Ala
    355                 360                 365

Gln Tyr Gly Gln Gln Ser Phe Met Thr Gly Ile Gln Asn Thr Ser Tyr
370                 375                 380

Arg Thr Asn Tyr Glu Asp Tyr Pro Phe Ser Gly Pro Leu His Gly Val
385                 390                 395                 400

Arg Tyr Ala Gly Asp Thr Ala Arg Ser Val Asp Asn Asn Gly Lys Asp
                405                 410                 415
```

```
Val Tyr Ser Ile Tyr Ser Thr Met Phe Pro Leu Glu Thr Asn Asn His
            420                 425                 430

Val His Glu Leu Arg Pro Gly Thr Ala Tyr Tyr Phe Gly Val Lys Gly
        435                 440                 445

His Arg His Asp Ala Thr Asp Arg Arg Thr Gly Asn Ser Ser Gln Lys
    450                 455                 460

Ile Leu Gly Glu Asp Ser Lys Thr Gly Arg Ile Ala Thr Gly Pro Ser
465                 470                 475                 480

Tyr Phe Ile Ser Glu Ile Pro Tyr Tyr Asp Lys Glu Thr Asn Glu Thr
                485                 490                 495

Ile Arg Pro Thr Pro Glu Lys Tyr Asn His Arg Leu Ser Tyr Ile Ser
            500                 505                 510

Ala Tyr Ala Thr Asp Cys Gly Arg Ile Ser Gly Val Arg Gly Asp Gly
        515                 520                 525

Cys Phe Arg Thr Pro Gln Met Cys Ala Trp Thr His Val Ser Ala Asp
    530                 535                 540

Pro Tyr Asn Thr Ile His Pro Asp Lys Ile Thr Gln Ile Ser Ala Val
545                 550                 555                 560

Lys Ala Phe Tyr Ile Trp Asp Thr Gly Glu Gly Gln Val Val Ser Gly
                565                 570                 575

Pro Gly Phe Thr Gly Gly Asp Leu Val Lys Leu Pro Tyr Asn Ala Arg
            580                 585                 590

Leu Lys Ile Arg Leu Lys Pro Thr Ser Thr Ser Lys Lys Tyr Arg Val
        595                 600                 605

Arg Val Arg Tyr Ala Ser Met Gly Ala Gly Thr Leu Arg Ala Glu Lys
    610                 615                 620

Trp Ser Pro Tyr Gly Ser Val Phe Ser Asn Phe Ala Tyr Glu Tyr Thr
625                 630                 635                 640

Gly Asp Ser Asn Lys Phe Asn Asn Phe Lys Tyr Leu Glu Thr Leu Ser
                645                 650                 655

Glu Ser Phe Asn Ile Ser Gly Val Glu Ile Ile Ile Gln Asn Leu Ser
            660                 665                 670

Ser Ser Gln Leu Ile Val Asp Lys Leu Glu Phe Ile Pro Ile
        675                 680                 685
```

<210> SEQ ID NO 7
<211> LENGTH: 643
<212> TYPE: PRT
<213> ORGANISM: Bacillus thuringiensis

<400> SEQUENCE: 7

```
Met Glu Asp Ser Ser Leu Asp Thr Leu Ser Ile Val Asn Glu Thr Asp
1               5                   10                  15

Phe Pro Leu Tyr Asn Asn Tyr Thr Glu Pro Thr Ile Ala Pro Ala Leu
            20                  25                  30

Ile Ala Val Ala Pro Ile Ala Gln Tyr Leu Ala Thr Ala Ile Gly Lys
        35                  40                  45

Trp Ala Ala Lys Ala Ala Phe Ser Lys Val Leu Ser Leu Ile Phe Pro
    50                  55                  60

Gly Ser Gln Pro Ala Thr Met Glu Lys Val Arg Thr Glu Val Glu Thr
65                  70                  75                  80

Leu Ile Asn Gln Lys Leu Ser Gln Asp Arg Val Asn Ile Leu Asn Ala
                85                  90                  95

Glu Tyr Arg Gly Ile Ile Glu Val Ser Asp Val Phe Asp Ala Tyr Ile
            100                 105                 110
```

```
Lys Gln Pro Gly Phe Thr Pro Ala Thr Ala Lys Gly Tyr Phe Leu Asn
            115                 120                 125

Leu Ser Gly Ala Ile Ile Gln Arg Leu Pro Gln Phe Glu Val Gln Thr
        130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
        195                 200                 205

Arg Leu Cys Lys Val Ser Leu Lys Asp Gly Leu Thr Phe Arg Asn Met
210                 215                 220

Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
        275                 280                 285

Asn Tyr Ser Phe Thr Asn Glu Pro Ala Asp Ile Pro Ala Arg Glu Asn
            290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Phe Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
        355                 360                 365

Ala Pro Ala Pro Ala Asp Leu Phe Phe Lys Asn Ala Asp Ile Asn Val
    370                 375                 380

Lys Phe Thr Gln Trp Phe Gln Ser Thr Leu Tyr Gly Trp Asn Ile Lys
385                 390                 395                 400

Leu Gly Thr Gln Thr Val Leu Ser Ser Arg Thr Gly Thr Ile Pro Pro
                405                 410                 415

Asn Tyr Leu Ala Tyr Asp Gly Tyr Tyr Ile Arg Ala Ile Ser Ala Cys
            420                 425                 430

Pro Arg Gly Val Ser Leu Ala Tyr Asn His Asp Leu Thr Thr Leu Thr
        435                 440                 445

Tyr Asn Arg Ile Glu Tyr Asp Ser Pro Thr Thr Glu Asn Ile Ile Val
    450                 455                 460

Gly Phe Ala Pro Asp Asn Thr Lys Asp Phe Tyr Ser Lys Lys Ser His
465                 470                 475                 480

Tyr Leu Ser Glu Thr Asn Asp Ser Tyr Val Ile Pro Ala Leu Gln Phe
                485                 490                 495

Ala Glu Val Ser Asp Arg Ser Phe Leu Glu Asp Thr Pro Asp Gln Ala
            500                 505                 510

Thr Asp Gly Ser Ile Lys Phe Ala Arg Thr Phe Ile Ser Asn Glu Ala
        515                 520                 525
```

```
Lys Tyr Ser Ile Arg Leu Asn Thr Gly Phe Asn Thr Ala Thr Arg Tyr
    530                 535                 540

Lys Leu Ile Ile Arg Val Arg Val Pro Tyr Arg Leu Pro Ala Gly Ile
545                 550                 555                 560

Arg Val Gln Ser Gln Asn Ser Gly Asn Asn Arg Met Leu Gly Ser Phe
                565                 570                 575

Thr Ala Asn Ala Asn Pro Glu Trp Val Asp Phe Val Thr Asp Ala Phe
                580                 585                 590

Thr Phe Asn Asp Leu Gly Ile Thr Thr Ser Ser Thr Asn Ala Leu Phe
                595                 600                 605

Ser Ile Ser Ser Asp Ser Leu Asn Ser Gly Glu Glu Trp Tyr Leu Ser
610                 615                 620

Gln Leu Phe Leu Val Lys Glu Ser Ala Phe Thr Thr Gln Ile Asn Pro
625                 630                 635                 640

Leu Leu Lys

<210> SEQ ID NO 8
<211> LENGTH: 724
<212> TYPE: PRT
<213> ORGANISM: Bacillus thuringiensis

<400> SEQUENCE: 8

Met Gln Asn Asn Asn Phe Asn Thr Thr Glu Ile Asn Asn Met Ile Asn
1               5                   10                  15

Phe Pro Met Tyr Asn Gly Arg Leu Glu Pro Ser Leu Ala Pro Ala Leu
                20                  25                  30

Ile Ala Val Ala Pro Ile Ala Lys Tyr Leu Ala Thr Ala Leu Ala Lys
            35                  40                  45

Trp Ala Val Lys Gln Gly Phe Ala Lys Leu Lys Ser Glu Ile Phe Pro
    50                  55                  60

Gly Asn Thr Pro Ala Thr Met Asp Lys Val Arg Ile Glu Val Gln Thr
65                  70                  75                  80

Leu Leu Asp Gln Arg Leu Gln Asp Asp Arg Val Lys Ile Leu Glu Gly
                85                  90                  95

Glu Tyr Lys Gly Ile Ile Asp Val Ser Lys Val Phe Thr Asp Tyr Val
                100                 105                 110

Asn Gln Ser Lys Phe Glu Thr Gly Thr Ala Asn Arg Leu Phe Phe Asp
            115                 120                 125

Thr Ser Asn Gln Leu Ile Ser Arg Leu Pro Gln Phe Glu Ile Ala Gly
        130                 135                 140

Tyr Glu Gly Val Ser Ile Ser Leu Phe Thr Gln Met Cys Thr Phe His
145                 150                 155                 160

Leu Gly Leu Leu Lys Asp Gly Ile Leu Ala Gly Ser Asp Trp Gly Phe
                165                 170                 175

Ala Pro Ala Asp Lys Asp Ala Leu Ile Cys Gln Phe Asn Arg Phe Val
            180                 185                 190

Asn Glu Tyr Asn Thr Arg Leu Met Val Leu Tyr Ser Lys Glu Phe Gly
        195                 200                 205

Arg Leu Leu Ala Lys Asn Leu Asn Glu Ala Leu Asn Phe Arg Asn Met
    210                 215                 220

Cys Ser Leu Tyr Val Phe Pro Phe Ser Glu Ala Trp Ser Leu Leu Arg
225                 230                 235                 240

Tyr Glu Gly Thr Lys Leu Glu Asn Thr Leu Ser Leu Trp Asn Phe Val
                245                 250                 255
```

```
Gly Glu Ser Ile Asn Asn Ile Ser Pro Asn Asp Trp Lys Gly Ala Leu
            260                 265                 270

Tyr Lys Leu Leu Met Gly Ala Pro Asn Gln Arg Leu Asn Asn Val Lys
        275                 280                 285

Phe Asn Tyr Ser Tyr Phe Ser Asp Thr Gln Ala Thr Ile His Arg Glu
    290                 295                 300

Asn Ile His Gly Val Leu Pro Thr Tyr Asn Gly Gly Pro Thr Ile Thr
305                 310                 315                 320

Gly Trp Ile Gly Asn Gly Arg Phe Ser Gly Leu Ser Phe Pro Cys Ser
                325                 330                 335

Asn Glu Leu Glu Ile Thr Lys Ile Lys Gln Glu Ile Thr Tyr Asn Asp
            340                 345                 350

Lys Gly Gly Asn Phe Asn Ser Ile Val Pro Ala Ala Thr Arg Asn Glu
        355                 360                 365

Ile Leu Thr Ala Thr Val Pro Thr Ser Ala Asp Pro Phe Phe Lys Thr
    370                 375                 380

Ala Asp Ile Asn Trp Lys Tyr Phe Ser Pro Gly Leu Tyr Ser Gly Trp
385                 390                 395                 400

Asn Ile Lys Phe Asp Asp Thr Val Thr Leu Lys Ser Arg Val Pro Ser
                405                 410                 415

Ile Ile Pro Ser Asn Ile Leu Lys Tyr Asp Asp Tyr Tyr Ile Arg Ala
            420                 425                 430

Val Ser Ala Cys Pro Lys Gly Val Ser Leu Ala Tyr Asn His Asp Phe
        435                 440                 445

Leu Thr Leu Thr Tyr Asn Lys Leu Glu Tyr Asp Ala Pro Thr Thr Gln
    450                 455                 460

Asn Ile Ile Val Gly Phe Ser Pro Asp Asn Thr Lys Ser Phe Tyr Arg
465                 470                 475                 480

Ser Asn Ser His Tyr Leu Ser Thr Thr Asp Asp Ala Tyr Val Ile Pro
                485                 490                 495

Ala Leu Gln Phe Ser Thr Val Ser Asp Arg Ser Phe Leu Glu Asp Thr
            500                 505                 510

Pro Asp Gln Ala Thr Asp Gly Ser Ile Lys Phe Thr Asp Thr Val Leu
        515                 520                 525

Gly Asn Glu Ala Lys Tyr Ser Ile Arg Leu Asn Thr Gly Phe Asn Thr
    530                 535                 540

Ala Thr Arg Tyr Arg Leu Ile Ile Arg Phe Lys Ala Pro Ala Arg Leu
545                 550                 555                 560

Ala Ala Gly Ile Arg Val Arg Ser Gln Asn Ser Gly Asn Asn Lys Leu
                565                 570                 575

Leu Gly Gly Ile Pro Val Glu Gly Asn Ser Gly Trp Ile Asp Tyr Ile
            580                 585                 590

Thr Asp Ser Phe Thr Phe Asp Asp Leu Gly Ile Thr Thr Ser Ser Thr
        595                 600                 605

Asn Ala Phe Phe Ser Ile Asp Ser Asp Gly Val Asn Ala Ser Gln Gln
    610                 615                 620

Trp Tyr Leu Ser Lys Leu Ile Leu Val Lys Glu Ser Ser Phe Thr Thr
625                 630                 635                 640

Gln Ile Pro Leu Lys Pro Tyr Val Ile Val Arg Cys Pro Asp Thr Phe
                645                 650                 655

Phe Val Ser Asn Asn Ser Ser Ser Thr Tyr Glu Gln Gly Tyr Asn Asn
            660                 665                 670
```

```
Asn Tyr Asn Gln Asn Ser Ser Met Tyr Asp Gln Gly Tyr Asn Asn
            675                 680                 685

Ser Tyr Asn Pro Asn Ser Gly Cys Thr Cys Asn Gln Asp Tyr Asn Asn
            690                 695                 700

Ser Tyr Asn Gln Asn Ser Gly Cys Thr Cys Asn Gln Gly Tyr Asn Asn
705                 710                 715                 720

Asn Tyr Pro Lys

<210> SEQ ID NO 9
<211> LENGTH: 648
<212> TYPE: PRT
<213> ORGANISM: Bacillus thuringiensis

<400> SEQUENCE: 9

Met His Tyr Tyr Gly Asn Arg Asn Glu Tyr Asp Ile Leu Asn Ala Ser
1               5                   10                  15

Ser Asn Asp Ser Asn Met Ser Asn Thr Tyr Pro Arg Tyr Pro Leu Ala
                20                  25                  30

Asn Pro Gln Gln Asp Leu Met Gln Asn Thr Asn Tyr Lys Asp Trp Leu
            35                  40                  45

Asn Val Cys Glu Gly Tyr His Ile Glu Asn Pro Arg Glu Ala Ser Val
        50                  55                  60

Arg Ala Gly Leu Gly Lys Gly Leu Gly Ile Val Ser Thr Ile Val Gly
65                  70                  75                  80

Phe Phe Gly Gly Ser Ile Ile Leu Asp Thr Ile Gly Leu Phe Tyr Gln
                85                  90                  95

Ile Ser Glu Leu Leu Trp Pro Glu Asp Asp Thr Gln Gln Tyr Thr Trp
            100                 105                 110

Gln Asp Ile Met Asn His Val Glu Asp Leu Ile Asp Lys Arg Ile Thr
        115                 120                 125

Glu Val Ile Arg Gly Asn Ala Ile Arg Thr Leu Ala Asp Leu Gln Gly
130                 135                 140

Lys Val Asp Asp Tyr Asn Asn Trp Leu Lys Lys Trp Lys Asp Asp Pro
145                 150                 155                 160

Lys Ser Thr Gly Asn Leu Ser Thr Leu Val Thr Lys Phe Thr Ala Leu
                165                 170                 175

Asp Ser Asp Phe Asn Gly Ala Ile Arg Thr Val Asn Asn Gln Gly Ser
            180                 185                 190

Pro Gly Tyr Glu Leu Leu Leu Pro Val Tyr Ala Gln Ile Ala Asn
        195                 200                 205

Leu His Leu Leu Leu Arg Asp Ala Gln Ile Tyr Gly Asp Lys Trp
210                 215                 220

Trp Ser Ala Arg Ala Asn Ala Arg Asp Asn Tyr Gln Ile Gln Leu
225                 230                 235                 240

Glu Lys Thr Lys Glu Tyr Thr Glu Tyr Cys Ile Asn Trp Tyr Asn Lys
                245                 250                 255

Gly Leu Asn Asp Phe Arg Thr Ala Gly Gln Trp Val Asn Phe Asn Arg
            260                 265                 270

Tyr Arg Arg Glu Met Thr Leu Thr Val Leu Asp Ile Ile Ser Met Phe
        275                 280                 285

Pro Ile Tyr Asp Ala Arg Leu Tyr Pro Thr Glu Val Lys Thr Glu Leu
290                 295                 300

Thr Arg Glu Ile Tyr Ser Asp Val Ile Asn Gly Glu Ile Tyr Gly Leu
305                 310                 315                 320
```

-continued

```
Met Thr Pro Tyr Phe Ser Phe Glu Lys Ala Glu Ser Leu Tyr Thr Arg
            325                 330                 335

Ala Pro His Leu Phe Thr Trp Leu Lys Gly Phe Arg Phe Val Thr Asn
            340                 345                 350

Ser Ile Ser Tyr Trp Thr Phe Leu Ser Gly Gly Gln Asn Lys Tyr Ser
            355                 360                 365

Tyr Thr Asn Asn Ser Ser Ile Asn Glu Gly Ser Phe Arg Gly Gln Asp
            370                 375                 380

Thr Asp Tyr Gly Gly Thr Ser Ser Thr Ile Asn Ile Pro Ser Asn Ser
385                 390                 395                 400

Tyr Val Tyr Asn Leu Trp Thr Glu Asn Tyr Glu Tyr Ile Tyr Pro Trp
            405                 410                 415

Gly Asp Pro Val Asn Ile Thr Lys Met Asn Phe Ser Val Thr Asp Asn
            420                 425                 430

Asn Ser Ser Lys Glu Leu Ile Tyr Gly Ala His Arg Thr Asn Lys Pro
            435                 440                 445

Val Val Arg Thr Asp Phe Asp Phe Leu Thr Asn Lys Glu Gly Thr Glu
450                 455                 460

Leu Ala Lys Tyr Asn Asp Tyr Asn His Ile Leu Ser Tyr Met Leu Ile
465                 470                 475                 480

Asn Gly Glu Thr Phe Gly Gln Lys Arg His Gly Tyr Ser Phe Ala Phe
            485                 490                 495

Thr His Ser Ser Val Asp Pro Asn Asn Thr Ile Ala Ala Asn Lys Ile
            500                 505                 510

Thr Gln Ile Pro Val Val Lys Ala Ser Ser Ile Asn Gly Ser Ile Ser
            515                 520                 525

Ile Glu Lys Gly Pro Gly Phe Thr Gly Gly Asp Leu Val Lys Met Arg
            530                 535                 540

Ala Asp Ser Gly Leu Thr Met Arg Phe Lys Ala Glu Leu Leu Asp Lys
545                 550                 555                 560

Lys Tyr Arg Val Arg Ile Arg Tyr Lys Cys Asn Tyr Ser Ser Lys Leu
            565                 570                 575

Ile Leu Arg Lys Trp Lys Gly Glu Gly Tyr Ile Gln Gln Gln Ile His
            580                 585                 590

Asn Ile Ser Pro Thr Tyr Gly Ala Phe Ser Tyr Leu Glu Ser Phe Thr
            595                 600                 605

Ile Thr Thr Thr Glu Asn Ile Phe Asp Leu Thr Met Glu Val Thr Tyr
            610                 615                 620

Pro Tyr Gly Arg Gln Phe Val Glu Asp Ile Pro Ser Leu Ile Leu Asp
625                 630                 635                 640

Lys Ile Glu Phe Leu Pro Thr Asn
            645
```

FUSION PROTEINS WITH IMPROVED PROPERTIES

RELATED APPLICATIONS

This application is a U.S. National Phase Application of PCT/CN2017/092393, International Filing Date Jul. 10, 2017 which claims priority to U.S. Provisional Patent Application No. 62/373,072, filed on Aug. 10, 2016, the contents of which are hereby incorporated by reference in the entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file Sequence_Listing_1123969.txt, created on Apr. 2, 2021, 65,042 bytes, machine format IBM-PC, MS-Windows operating system, is hereby incorporated by reference in its entirety for all purposes.

BACKGROUND OF THE INVENTION

In the industrial synthesis context many enzymes are useful for their capability of catalyzing various chemical reactions. The cost of such industrial applications can be very high, however, due to the constant need to replace used enzymes in order to ensure proper efficiency of the reactions. The present invention provides fusion enzymes with improved organic solvent tolerance and enhanced recyclability. These enzymes can be used as biocatalysts in industrial synthesis in an increased number of cycles. Organic tolerant and recyclable enzymes have strong commercial potentials in a variety of industrial applications ranging from synthesis of enantiomerically pure pharmaceutical compounds to production of alternative fuels such as biodiesel.

BRIEF SUMMARY OF THE INVENTION

This invention provides a novel approach to improve the physical properties and therefore reusability of enzymes in various industrial applications. Thus, in a first aspect, this invention provides a fusion protein comprising (1) an enzyme; and (2) a Cry protein or a crystal-forming fragment thereof, such that the fusion protein is capable of self-crystalizing or spontaneously forming crystals once it is expressed within a cell. In some embodiments, the enzyme is a lipase, ligase, hydrolase, esterase, protease, glycosidase, or peptide deformylase. As a result of being fused to a Cry protein or a crystal-forming fragment of a Cry protein, the fusion protein exhibits substantially improved stability at an elevated temperature (e.g., at least 40, 50, 60, 70, 80° C. or higher) and/or in the presence of an organic solvent (e.g., alcohol such as methanol and ethanol, or acetonitrile), even after a prolonged time period (e.g., after at least 12 hours, 24 hours, 1, 2, 3, 4, 5 or more days). For example, the enzymatic activity of the fusion protein is preserved at least 25, 30, 40, 50, 60, 70, 75, 70, 90, 95% or higher of the pre-treatment level after the solvent and/or heat treatment, which confers to the fusion protein a highly advantageous characteristic allowing for great recyclability in industrial applications. In addition to its enhanced thermostability and tolerance for organic solvents, the fusion protein typically retains at least a portion of the enzyme's natural level of activity, for example, at least 10%, 25%, 50%, 75%, 80%, 85%, 90%, 95% or more of the activity possessed by the native enzyme (i.e., without being fused with any fusion partner).

In some embodiments, the Cry protein is the Cry3Aa protein. In some embodiments, the crystal-forming fragment is less than full length of a Cry protein, for example, a fragment of the Cry3Aa protein, e.g., a fragment comprising domain I of the protein, a fragment consisting of the first 290 amino acids of Cry3Aa protein (from the N-terminus), or a fragment consisting of the first 626 amino acids of Cry3Aa protein (from the N-terminus), or the 498-644 fragment of Cry3As protein. In some embodiments, a peptide linker is between the enzyme and the Cry protein or the crystal-forming fragment. In some embodiments, the fusion protein is in crystalline form, and it may be further crosslinked, e.g., by a chemical crosslinking agent such as glutaraldehyde or bis(sulfosuccinimidyl)suberate (BS3). In some embodiments, the fusion protein consists essentially of an enzyme, located at the N-terminus of the fusion protein, and the Cry protein or crystal-forming fragment thereof, located at the C-terminus of the fusion protein. Optionally, the fusion protein may include a peptide linker inserted between the enzyme and the Cry protein or the crystal-forming fragment thereof. Some exemplary fusion proteins of this invention include those provided in the Examples and Figures of this disclosure, e.g., a fusion resulted from any combination of (1) full length Cry3Aa, Cry3Aa(1-290), Cry3Aa(1-626), or Cry3Aa(498-644) with (2) a suitable enzyme such as a lipase (e.g., lipA), Dieselzyme (e.g., Dieselzyme 4, DLZM4), a peptide deformylase (PDF), or a p-nitrobenzyl esterase (pnbA).

In a second aspect, the present invention provides a polynucleotide sequence encoding the fusion protein described above and herein. In some embodiments, the polynucleotide sequence is present in an expression cassette, which is typically a recombinantly produced nucleotide structure comprising a promoter operably linked to the polynucleotide sequence encoding the fusion protein. In some embodiments, the expression cassette may be present in the form of a polynucleotide vector, such as a plasmid or a viral vector. In a related aspect, this invention provides a host cell comprising the fusion protein described above and herein, a host cell comprising the polynucleotide sequence encoding the fusion protein, and a host cell comprising the expression cassette or vector that contains the polynucleotide sequence encoding the fusion protein. In some cases, the host cell is a bacterial cell or one derived from a bacterium, especially a cell of a *Bacillus* sp. bacterium, such as *Bacillus subtilis* (Bs) or *Bacillus thuringiensis* (Bt) cell. In some embodiments, the bacterium is *E. coli*.

In a third aspect, the present invention provides a method for recombinantly producing the fusion protein of this invention. The method includes the steps of (i) introducing the polynucleotide sequence encoding the fusion protein described above and herein into a host cell; and (ii) culturing the cell under conditions permissible for the expression of the fusion protein. The polynucleotide sequence encoding the fusion protein may be in the form of an expression cassette or a vector such as a plasmid. In some embodiments, the host cell expressing the fusion protein of this invention is a bacterial cell, especially of *Bacillus* sp. such as a *Bacillus subtilis* (Bs) cell or *Bacillus thuringiensis* (Bt) cell. Another bacterial strain, such as *E.coli*, may also be used. In some cases, the method of recombinantly producing the fusion protein further includes a step (iii) of purifying the fusion protein after it has been expressed by the host cell. Optionally, an additional step (iv) may be included in this method, where the fusion protein is then chemically crosslinked, for example, by a chemical crosslinking agent such as glutaraldehyde or bis(sulfosuccinimidyl)suberate (BS3). Typically, the fusion protein assumes a crystalline form or crystalized form upon its expression within the host cells. It may be purified and then crosslinked in the crystal form; or it may be purified and then solubilized if necessary.

In a fourth aspect, the present invention provides a composition comprising the fusion protein described above and herein, namely a self-crystalizing fusion protein comprising an enzyme fused to a Cry protein or a crystalizing fragment thereof, and a substrate to the enzyme. In some embodiments, the fusion protein is crystalized and optionally chemically crosslinked. In some embodiments, water and one or more organic solvents are further included in the composition. In some embodiments, a solid support is also included in the composition, with the fusion protein immobilized on the solid support.

In a fifth aspect, the present invention provides a method for performing a reaction using the fusion protein described above and herein, the reaction being one that is typically catalyzed by the native enzyme encompassed in the fusion protein. This method includes the step of incubating the fusion protein of this invention with a substrate to the enzyme under conditions permissible for the substrate to be catalyzed by the enzyme. In some cases, the fusion protein is in the crystalline form, and optionally crosslinked, such as by a chemical crosslinking agent glutaraldehyde or bis (sulfosuccinimidyl)suberate (BS3). In some embodiments, the method further comprises a cleaning step, performed after the reaction is completed to remove the reaction product(s) and cleaning the fusion protein for reuse in a second reaction.

BRIEF DESCRIPTION OF THE DRAWINGS

FIG. 1. Electron micrograph of *Bacillus* sp. highlighting its crystal inclusion.

FIG. 2. Fluorescence images (100×) of Cry3Aa-GFP crystals (reproduced from reference 19).

FIG. 3. Electron micrographs of purified Cry3Aa protein crystals (a) and Cry3Aa-GFP fusion protein crystals (b) (reproduced from reference 19).

FIG. 4. Hydrolysis of pNPA, the substrate for lipA and pnb stability studies. pNP absorbs light at 405 nm. Enzymatic hydrolysis by pnbA or lipA of 4-nitrophenylacetate (pNPA) yields the yellow product 4-nitrophenol (pNP).

FIG. 5. Thermal stability of wild-type lipA protein (solid line) and Cry3Aa-lipA crystals (dashed line). Samples were heated at various temperatures in a PCR block and residual activity was measured in triplicate.

FIG. 6. Cry3Aa-lipA (dashed) and free lipA (black) reaction rates against pNPA hydrolysis with increasing concentrations of acetonitrile (ACN) (6*a*) and ethanol (EtOH) (6*b*). These data illustrate that Cry3A-lipA crystals are more active than free lipA in these organic solvents.

FIG. 7. Cry3Aa-lipA (dashed) and free lipA (black) were incubated in 50% indicated solvent, and analyzed for residual activity after 24 hours, Cry3Aa-lipA crystals are shown to be much more stable than the free lipA enzyme in nearly all organic solvents tested.

FIG. 8. Activity of Cry3Aa-PMlip crystals against p-nitrophenyl palmitate (pNPP) compared to Cry3Aa crystal control. The Cry3Aa-PMlip crystals clearly have lipase activity against pNPP.

FIG. 9. GC trace of *Burkholderia cepacia* lipase (Sigma), Cry3Aa-PMlip and Cry3Aa monitoring their transesterase activity against canola oil. The data clearly show that Cry3Aa-PMlip can act similarly to *Burkholderia cepacia* lipase, a known commercially available biodiesel lipase.

FIG. 10. List of mutations in engineered dieselzymes, reproduced from reference 27.

FIG. 11. Operational stability of covalently immobilized wild-type PMlip, DLZM4, and BClip. Each cycle represents the % conversion over 20 hrs, adapted from reference 27.

FIG. 12. SDS-PAGE of purified and solubilized Cry3Aa-pnbA crystals.

FIG. 13. SDS-PAGE of purified wild-type pnbA protein.

FIG. 14. Free pnbA (black) and Cry3Aa-pnbA crystals (white) reaction rates against pNPA hydrolysis with increasing concentrations of ACN (14*a*) and EtOH (14*b*).

FIG. 15. Free pnbA (black) and Cry3Aa-pnbA crystals (dashed) were incubated with increasing concentrations of 4-nitrophenyl acetate and rate curves and parameters were calculated using Prism.

FIG. 16. Recyclability of Cry3Aa-pnbA (dashed) and Cry3Aa-lipA (black) crystals. Crystals were assayed for activity using 4npA, centrifuged and washed with phosphate buffer, and assayed again in subsequent reaction cycles. The activities were normalized to the activity in cycle 1.

FIG. 17. Cry3Aa-lipA crystals were incubated with or without 1% glutaraldehyde for 6 hours, and then washed in Tris buffer. Crystals were then incubated in pH 11 buffer for 2 hours, centrifuged and the protein amount was determined in the supernatant by Bradford.

Figure 18:
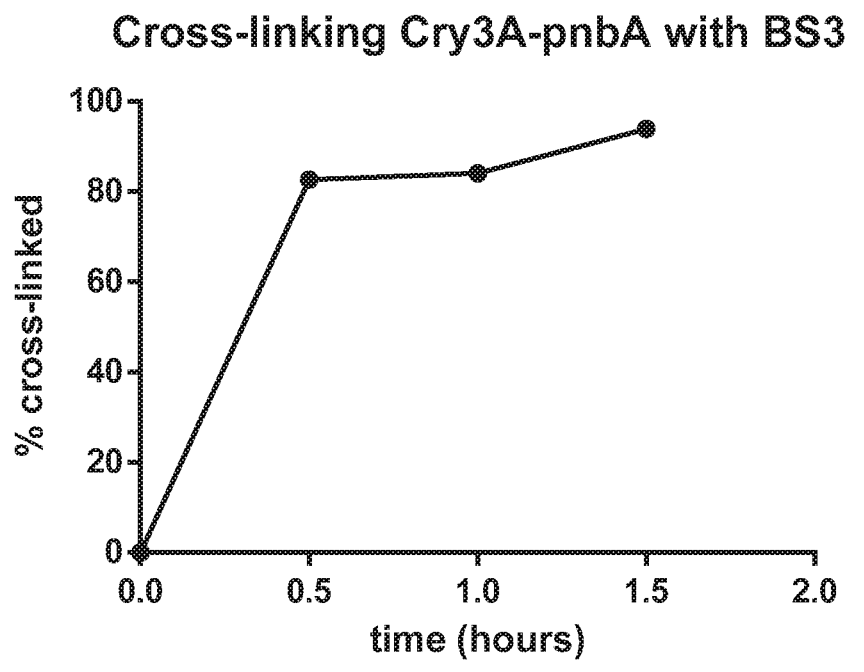

FIG. 18. Cry3A-pnbA crystals were incubated with BS3 cross-linker and at various timepoints an aliquot was evaluated for its ability to solubilize at pH 11.

FIG. 19. Recyclability of crosslinked Cry3Aa-pnbA (dashed) and cross-linked Cry3Aa-lipA (black) crystals. Crystals were assayed for activity using 4npA, centrifuged and washed with phosphate buffer, and assayed again in subsequent reaction cycles.

FIG. 20. Free pnbA (black), and cross-linked Cry3A-pnbA (checkered) were assayed for activity in different concentration of ACN (20*a*) or EtOH (20*b*).

FIG. 21. Free lipA (black), and cross-linked Cry3Aa-lipA (checkered) were assayed for activity in different concentration of ACN (21*a*) or EtOH (21*b*).

FIG. 22. Free PDF (black) and Cry3Aa-PDF (white) were incubated with different concentrations of indicated solvent and fMAS substrate for 30 min, and the formate produced was analyzed in a subsequent reaction by a coupled reaction with formate dehydrogenase. The NADH produced was monitored at 340 nm on a Tecan M1000, and rates were normalized to the rate at 0% solvent.

FIG. 23. SDS-PAGE of solubilized Cry3Aa(1-290)-lipA, Cry3Aa-lipA, and Cry3Aa.

FIG. 24. Free lipA (black) and Cry3Aa(1-290)-lipA (dotted) were assayed for activity in different concentrations of ACN (24*a*) or EtOH (24*b*).

FIG. 25. Free lipA (black) and Cry3Aa(1-290)-lipA (dashed) were incubated in 50% ACN and at indicated time-points an aliqot was taken and diluted to 10% ACN and analyzed for residual activity against pNPA substrate.

FIG. 26. Thermal stability of free lipA (black) and Cry3Aa(1-290)-lipA (dashed). Samples were heated at various temperatures in a PCR block and residual activity was measured in triplicate.

FIG. 27. Table of all Cry3A truncations that are fused to lipA.

FIG. 28. Scanning Electron Microscopy (SEM) of Cry3Aa-lipA variants. All form uniform particles of approximately the same size.

FIG. 29. Activity of Cry3Aa-lipA truncation variants in terms of rate (Absorbance at 405 nm over time) vs. enzyme concentration in (µg/ml). Cry3Aa(498-644)-lipA activity is significantly higher than the other constructs.

FIG. 30. Thermal stability of all Cry-truncation lipA fusion constructs. Samples were heated at various temperatures in a PCR block for 1 hour and residual activity was measured in triplicate.

FIG. 31. Free lipA (blue) and Cry3Aa(1-626)-lipA (red) were assayed in triplicate in various concentrations of ACN (a) or EtOH (b).

FIG. 32. Free lipA (blue) and Cry3Aa(1-626)-lipA (red) were incubated in 50% indicated solvent, and analyzed for residual activity after 24 hours. Samples were diluted to 10% solvent prior to measuring residual activity in triplicate.

FIG. 33. Thermal stability of Cry3Aa(1-626)-lipA (red) and his-lipA aggregates (purple). Samples were heated at various temperatures for 1 hour and residual activity was measured in triplicate.

FIG. 34. Thermal stability of soluble Cry3Aa(1-626)-lipA (green) and his-lipA (pink) at pH 11. Cry3Aa(1-626)-lipA crystals were solubilized at pH 11 overnight to obtain soluble protein. Samples were heated for 1 hour at pH 11 at various temperatures and measured for residual activity in triplicate.

FIG. 35. Recyclability of Cry3Aa(1-626)-lipA in the synthesis of biodiesel. The reaction for each cycle is as follows: 3:1 methanol:coconut oil, 30% water, 1.0% and 2.5% catalyst w/w of oil, 2,000 rpm, 30° C., 48 hours.

FIG. 36. Cry3Aa-DLZM4 (red) and Cry3Aa(1-626)-DLZM4 (blue) activity against the substrate p-nitrophenyl-palmitate (pNPP). pNPP hydrolyzes to form p-nitrophenol which absorbs at 405 nm.

FIG. 37. Free DLZM4 (blue) and Cry3Aa(1-626)-DLZM4 (orange) were incubated in 50% of MeOH and aliquots were taken at given time points for up to 50 hours, diluted to 10% solvent and analyzed for residual activity against pNPP. Activities were normalized to the activity at 0 hours.

FIG. 38. Free DLZM4 (black) and Cry3Aa(1-626)-DLZM4 (striped) were incubated in 50% of MeOH and aliquots were taken at 0 and 5 days, diluted to 10% solvent and analyzed for residual activity against pNPP. Activities were normalized to the activity at 0 days.

FIG. 39. Free DLZM4 (blue) and Cry3Aa(1-626)-DLZM4 (orange) were incubated in 50% of EtOH and aliquots were taken at given time points for up to 50 hours, diluted to 10% solvent and analyzed for residual activity against pNPP. Activities were normalized to the activity at 0 hours.

FIG. 40. Free DLZM4 (black) and Cry3Aa(1-626)-DLZM4 (striped) were incubated in 50% of EtOH and aliquots were taken at 0 and 5 days, diluted to 10% solvent and analyzed for residual activity against pNPP. Activities were normalized to the activity at 0 days.

FIG. 41. Free DLZM4 (blue) and Cry3Aa(1-626)-DLZM4 (orange) were diluted in 50% MeOH and heated at given temperatures for 1 hour. Residual activity was determined by pNPP hydrolysis, and rates were normalized to the rate at 30° C.

FIG. 42. Biodiesel production: free BCL enzyme (blue) and Cry3Aa(1-626)-DLZM4 (orange) biodiesel conversion over the first 24 hours.

FIG. 43. Recyclability of Cry3A(1-626)-DLZM4 biodiesel synthesis over five 24-hour reaction cycles.

FIG. 44. SDS-PAGE of his-Cry3A-lipA protein production in E. coli. 100 kDa purified band corresponds to full length his-Cry3A-lipA.

FIG. 45. Activity of soluble his-Cry3A-lipA and insoluble his-Cry3A-lipA proteins produced from E. coli. Activity was measured using pNPA as a substrate. Data demonstrate that E. coli can produce active inclusions of Cry-enzymes.

DEFINITIONS

The term "Cry protein," as used herein, refers to any one protein among a class of crystalline proteins produced by strains of *Bacillus thuringiensis*. Some examples of "Cry proteins" include, but are not limited to, Cry1Aa, Cry1Ab Cry2Aa, Cry3Aa, Cry4Aa, Cry4Ba, Cry11Aa, Cry11Ba, and Cry19Aa. Their amino acid sequences and polynucleotide coding sequences are known and can be found in publications such as U.S. Patent Application published as US2010/0322977. Their GenBank Accession Nos are:

Cry1Aa AY197341.1 (SEQ ID NO:1)
Cry1Ab AY847289.1 (SEQ ID NO:2)
Cry2Aa AF273218.1 (SEQ ID NO:3)
Cry3Aa AJ237900.1 (SEQ ID NO:4)
Cry4Aa AB513706.1 (SEQ ID NO:5)
Cry4Ba AB161456.1 (SEQ ID NO:6)
Cry11Aa AL731825.1 (SEQ ID NO:7)
Cry11Ba LC153032.1 (SEQ ID NO:8)
Cry19Aa Y07603.1 (SEQ ID NO:9)

In addition to the wild-type Cry proteins, the term "Cry protein" also encompasses functional variants, which (1) share an amino acid sequence identity of at least 80%, 81%, 82%, 83%, 84%, 88%, 89%, 90%, 91%, 92%, 93%, 94%, 95%, 96%, 97%, 98%, 99%, or 99.5% to the polypeptide sequence of any one of the Cry proteins listed in US2010/0322977; and (2) retain the ability to spontaneously form crystals within host cells as can be confirmed by known methods such as electron micrograph (see description in, e.g., references 16-19). Similarly, a "crystal-forming fragment" of a Cry protein is a fragment of any of the known Cry proteins (i.e., less than full length of the wild-type Cry protein) that still retains the ability of self-crystalization, which is demonstrated both by crystallization by the fragment alone and by causing a fusion protein to self-crystalize when the fragment is present in the fusion protein with another protein of interest (e.g., an enzyme). In addition to being a truncated form of a Cry protein, a "crystal-forming fragment" may further contain one or more modifications to the native amino acid sequence such as insertions, deletions, or substitutions, especially conservative modifications, such that the resultant "crystal-forming fragment" shares an amino acid sequence identity of at least 80%, 81%, 82%, 83%, 84%, 88%, 89%, 90%, 91%, 92%, 93%, 94%, 95%, 96%, 97%, 98%, 99%, or 99.5% to the polypeptide sequence of the corresponding fragment of a wild-type Cry protein.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a Cry protein or a crystal-forming fragment of a Cry protein sequence comprised in the fusion protein of this invention has at least 80% identity, preferably 85%, 90%, 91%, 92%, 93, 94%, 95%, 96%, 97%, 98%, 99%, or 100% identity, to a reference sequence, e.g., the amino acid sequence of a corresponding wild-type Cry protein or fragment), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see. e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

A "fusion protein consisting essentially of an enzyme and a Cry protein or a crystal-forming fragment thereof" is a fusion protein that contains only an enzyme (such as lipase, ligase, hydrolase, esterase, protease, or glycosidase, etc.) and a Cry protein or a crystal-forming fragment thereof, but does not contain any other discernable elements such as any full-length proteins, functional domains of proteins, or tags providing any particular binding affinity of antigenicity. This fusion protein, however, may contain one or more amino acid sequences that (1) provide linkage and proper spatial separation between the enzyme and the Cry protein/crystal-forming fragment thereof to preserve functionality or (2) provide the correct reading frame and/or appropriate start/termination of the fusion protein. Such linkage amino acid sequences are relatively shorts and typically no longer than 100 or 50 amino acids, such as between 1 to 100, 1 or 2 to 50, 2 or 3 to 25, 3 or 4 to 10 amino acids.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral vector derived from a viral genome, or nucleic acid fragment/construct. Typically, an expression cassette includes a polynucleotide to be transcribed, operably linked to a promoter. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

DETAILED DESCRIPTION OF THE INVENTION

I. Introduction

Figure 1:
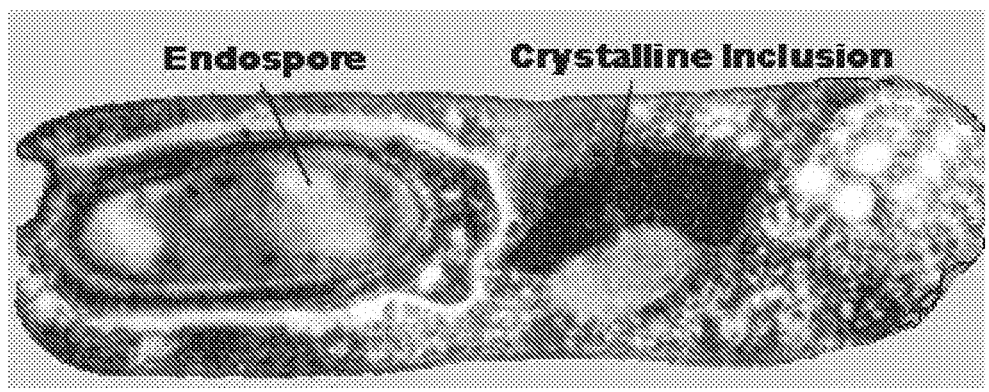

There has been growing interest in using enzymes to catalyze industrial reactions due to their high reactivity, excellent regio- and enantiospecificity, and low environmental toxicity. In order to financially compete with chemical catalysis, biocatalysts are optimized so they can be recycled multiple times. Additionally, biocatalysts are generally optimized so they can withstand high concentrations of organic solvents—conditions that can promote substrate solubility and enzyme activity. By generating novel fusion proteins capable of self-crystallization, the present inventors have developed an innovative and effective strategy to produce enzymes with enhanced recyclability and organic solvent tolerance.

Currently, generating organic solvent-tolerant enzymes such as lipases for industrial use requires laborious techniques such as directed evolution. The inventors devised a novel method to recombinantly generate enzymes that are highly tolerant to organic solvents. These enzymes can also be readily recycled for reuse in subsequent reaction cycles. These properties are highly desirable and advantageous in the context of optimizing biocatalysts for commercial applications.

II. Production of Cry Fusion Proteins

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, such as the polynucleotide sequence encoding a lipase or hydrolase, a polynucleotide encoding a Cry protein or fragment, and synthetic oligonucleotides can be verified after cloning or subcloning using, e.g., the chain termination method for sequencing double-stranded templates of Wallace et al., *Gene* 16: 21-26 (1981).

B. Coding Sequence for a Cry Fusion Protein

Polynucleotide sequences encoding Cry fusion proteins of this invention can be readily constructed by combining the coding sequences for the fusion partners, such as a Cry3Aa protein and *Bacillus subtilis* lipase A (lipA). The sequences for Cry proteins and enzymes are generally known and may be obtained from a commercial supplier.

In addition to the use of full length wild-type Cry proteins for constructing the Cry fusion proteins of this invention, fragments of Cry proteins and/or variants of Cry proteins may also be useful. A DNA sequence encoding a Cry protein can be modified to generate fragments or variants of the Cry protein. So long as the fragments and variants retain the ability to spontaneously form crystals when expressed in a host cell, especially a *Bacillus* bacterial cell, they can be used for producing the fusion proteins and render the fusion proteins the ability to undergo spontaneous crystallization. Typically, the variants bear a high percentage of sequence identity (e.g., at least 80, 85, 90, 95, 97, 98, 99% or higher) to the wild-type Cry protein sequence, whereas the fragments may be substantially shorter than the full length Cry protein, such as having some amino acids (e.g., 10-300 or 20-200 or 50-100 amino acids) removed from the N- or C-terminus of the full length Cry protein. For example, a useful Cry3Aa fragment may be as short as the first 290 amino acids from the N-terminus, encompassing Domain I of the protein. Other examples of such fragments include a Cry protein fragment having its first 57 amino acids from N-terminus removed and a Cry protein fragment having its C-terminal 18 amino acids removed. The ability of a fusion protein to undergo spontaneous crystallization can be verified by electron micrograph, whereas the fusion protein's enzymatic activity can be confirmed by established assays for each specific enzyme. Surprisingly, the present inventors discovered during their studies that the presence of a Cry protein in a fusion protein affords a significant increase to the enzyme in its ability to remain active when exposed to organic solvents. In other words, the fusion protein is far more tolerant to organic solvents, even at high concentrations, than the enzyme by itself. The inventors further revealed that a fragment of Cry3Aa comprising Domain I of the protein is able to confer to a fusion protein significantly enhanced tolerance, stability, and activity in the presence of high concentration of organic solvents, and the level of such enhancement is notably greater than the full length protein Cry3Aa.

In some cases, a peptide linker or spacer is used between the coding sequences for the Cry protein/fragment and the enzyme. One purpose is to ensure the proper reading frame for the fusion protein such that the coding sequences for both Cry protein/fragment and the enzyme are in frame. Another purpose is to provide appropriate spatial relationship between the Cry protein/fragment and the enzyme, such that each may retain its original functionality: the Cry protein/fragment is able to cause self-crystallization of the fusion protein, and the enzyme remains active in its catalytic capacity. Also, one or more linkers may be placed at the very beginning and/or the very end of the open reading frame, so as to facilitate proper start and termination of the coding sequence translation. Such linkage amino acid sequences are usually shorts and typically no longer than 100 or 50 amino acids, such as between 1 to 100, 1 or 2 to 50, 2 or 3 to 25, 3 or 4 to 10 amino acids.

C. Sequence Modification for Preferred Codon Usage in a Host Organism

The polynucleotide sequence encoding a Cry fusion protein of this invention can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of a Cry fusion protein.

III. Expression, Purification, and Crosslinking of Cry Fusion Proteins

Following verification of the coding sequence, a fusion protein of this invention can be produced using routine techniques in the field of recombinant genetics, relying on the polynucleotide sequences encoding the Cry fusion protein disclosed herein.

A. Expression Systems

To obtain high level expression of a nucleic acid encoding a fusion protein of this invention, one typically subclones a polynucleotide encoding the fusion protein in the correct reading frame into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella,* and *Caulobacter.* Kits for such expression systems are commercially available.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function. In some cases, a constitutive promoter is used, whereas in other cases an inducible promoter rather than a constitutive promoter is preferred.

In addition to the promoter, the expression vector typically includes a transcription unit or expression cassette that contains all the additional elements required for the expression of the fusion protein of this invention in host cells. A typical expression cassette thus contains a promoter operably linked to the nucleic acid sequence encoding the fusion protein and signals required for efficient polyadenylation of the transcript, ribosome binding sites, and translation termination. The nucleic acid sequence encoding the fusion protein may be linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the coding sequence to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used, especially those suitable for expression in cells of *Bacillus* sp, such as *Bt* and *Bs.* Standard bacterial expression vectors include plasmids such as pBR322 based plasmids, pSKF, pET23D, and fusion expression systems such as GST and LacZ.

The elements that are typically included in expression vectors also include a replicon that functions in bacteria such as *Bacillus* sp.and *E. coli,* a gene encoding antibiotic resistance to permit selection of bacteria that harbor recombinant plasmids, and unique restriction sites in nonessential regions of the plasmid to allow insertion of coding sequences. The particular antibiotic resistance gene chosen is not critical, any of the many resistance genes known in the art are suitable. Similar to antibiotic resistance selection markers, metabolic selection markers based on known metabolic pathways may also be used as a means for selecting transformed host cells.

B. Transfection Methods

Standard transfection methods are used to produce bacterial, mammalian, yeast, insect, or plant cell lines that express large quantities of a recombinant fusion protein of this invention, which are then purified using standard techniques (see, e.g., Colley et al., *J. Biol. Chem.* 264: 17619-17622 (1989); *Guide to Protein Purification,* in *Methods in Enzymology,* vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the fusion protein of this invention.

C. Purification of Cry Fusion Proteins

Once the expression of a Cry fusion protein in transfected host cells is confirmed, e.g., via electron micrograph for detecting protein crystals or an immunoassay such as Western blotting analysis, the host cells are then cultured in an appropriate scale for the purpose of purifying the recombinant Cry fusion protein.

When the Cry fusion proteins of the present invention are produced recombinantly by transformed bacteria in large amounts, for example after promoter induction, the proteins are present in crystalline form or insoluble aggregates within the host cells. Thus, one can readily isolate the crystals from the cell lysate based on their distinct density by utilizing techniques such as centrifugation and density gradient separation followed by one or more rinsing steps to further remove contaminants from the protein crystals.

There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

While the Cry fusion protein crystals tend to remain insoluble at lower or neutral pHs, placing them in alkaline solutions with pH at or greater than 10 or 11 can often effectively dissolve the protein. Once dissolved, the protein can then be analyzed by gel separation (e.g., on an SDS gel) and immunoassays to confirm its identity based on the appropriate molecular weight and immunoreactivity.

D. Crosslinking Cry Fusion Proteins

Crosslinking is a commonly used technique for a broad ranges of goals, such as to stabilize protein tertiary and quaternary structure for analysis; to capture and identify unknown protein interactors or interaction domains; to conjugate an enzyme or tag to an antibody or other purified protein; to immobilize antibodies or other proteins for assays or affinity-purification; and to attach peptides to larger "carrier" proteins to facilitate handling/storage. The present inventors have observed that crosslinking tends to further enhance the desirable properties of the Cry fusion protein crystals such as thermostability and tolerance to organic solvents. Thus, in some cases there is a preference to further crosslink a Cry fusion protein upon its recombinant production and purification.

Despite the complexity of protein structure, including composition with 20 different amino acids, only a small number of protein functional groups comprise selectable targets for practical crosslinking methods. In fact, just four protein chemical targets account for the vast majority of crosslinking and chemical modification techniques: (1) primary amines (—NH2): this group exists at the N-terminus of each polypeptide chain and in the side chain of lysine (Lys, K) residues; (2) carboxyls (—COOH): this group exists at the C-terminus of each polypeptide chain and in the side chains of aspartic acid (Asp, D) and glutamic acid (Glu, E); (3) sulfhydryls (—SH): this group exists in the side chain of cysteine (Cys, C). Often, as part of a protein's secondary or tertiary structure, cysteines are joined together between their side chains via disulfide bonds (—S—S—); and (4) carbonyls (—CHO): these aldehyde groups can be created by oxidizing carbohydrate groups in glycoproteins. For each of these protein functional-group targets, there exist one to several types of reactive groups that are capable of targeting them and have been used as the basis for synthesizing crosslinking and modification reagents. Crosslinkers are selected on the basis of their chemical reactivities (i.e., specificity for particular function groups) and other chemical properties that facilitate their use in different specific applications.

After a fusion protein of the present invention, e.g., a Cry3Aa-lipA fusion protein, is recombinantly produced in host cells (such as *Bacillus subtilis* cells or *Bacillus thuringiensis* cells) in a crystalline form and then properly purified, it can then be chemically crosslinked to further increase the level of enhancement in the protein's properties such as thermosstability and tolerance to organic solvents. Well-known chemical crosslinking reagents can be used for this purpose in accordance with the established procedures. Some examples of suitable crosslinking reagents include glutaraldehyde, bis(sulfosuccinimidyl)suberate (BS3), phenol-formaldehyde, Lys to lys cross-linking:DSG (disuccinimidyl glutarate), Lys to cys cross-linking: Sulfo-EMCS (N-ε-maleimidocaproyl-oxysulfosuccinimide ester), Cys to cys cross-linking, BMH (bismaleimidohexane).

IV. Applications of Cry Fusion Proteins

Another aspect of the present invention relates to the use of a Cry fusion protein described herein to perform reactions typically catalyzed by the enzyme present in the fusion protein, such as hydrolysis, esterification, ligation, proteolysis, and the like. As organic solvents are often able to facilitate such reactions and the fusion protein of this invention is highly tolerant to the presence of organic solvents, a reaction performed using the Cry fusion protein of this invention often not only a water-based solvent but also one or more organic solvents, e.g., ethanol, methanol, acetonitrile, and dimethylformamide.

As the inventors discovered that chemical crosslinking of the crystalline Cry fusion proteins leads the proteins to have a higher level of resistance to organic solvents and a higher level of thermostability, potentially can retain enzymatic activity for use in more cycles of reactions, in some cases it is preferable that crosslinked crystalline fusion proteins (as opposed to uncrosslinked fusion proteins) are used. Furthermore, the fusion proteins may be immobilized to a solid surface, especially a surface within a reaction chamber where the reaction is to take place, such as the surface of a removable inner structure of the reaction chamber, for ease of cleaning, recycling, and reuse of the fusion proteins. In some cases, this reaction process includes a cleaning step, performed after the completion of one round of the reaction and removal of the reaction product(s) as well as any remaining substrate, during which the fusion protein is rinsed or washed in preparation of being used again with fresh substrate in a subsequent round of reaction.

EXAMPLES

The following examples are provided by way of illustration only and not by way of limitation. Those of skill in the art will readily recognize a variety of non-critical parameters that could be changed or modified to yield essentially the same or similar results.

Example 1: Production and Activity of Cry3Aa-lipA

Introduction

Background of Research

Figure 2:
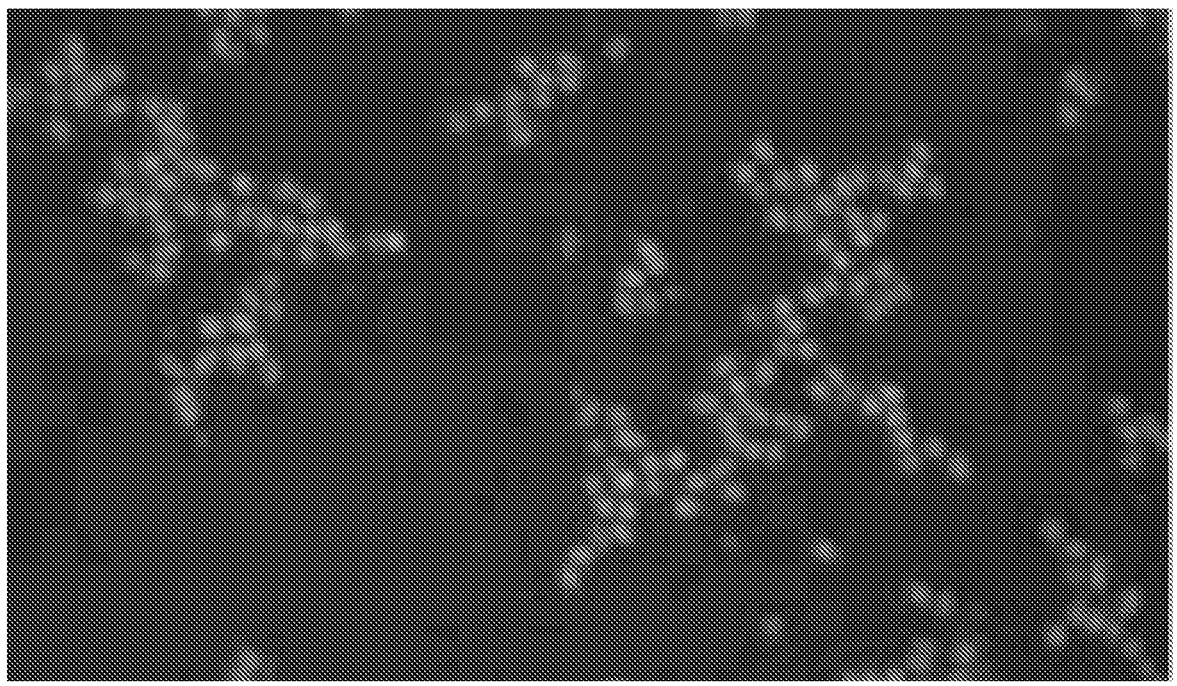
Figure 3A:
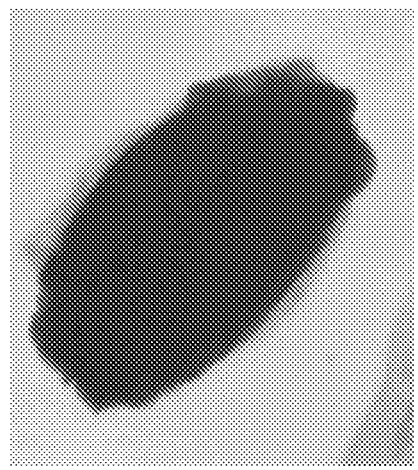
Figure 3B:
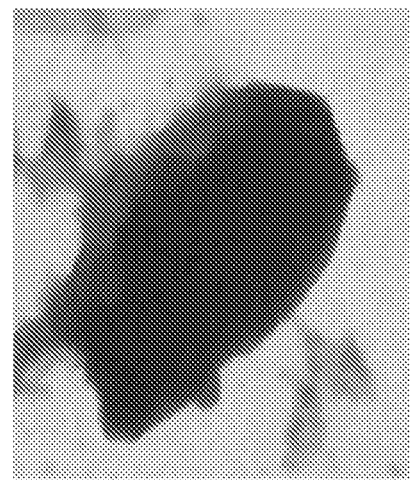
Figure 4:
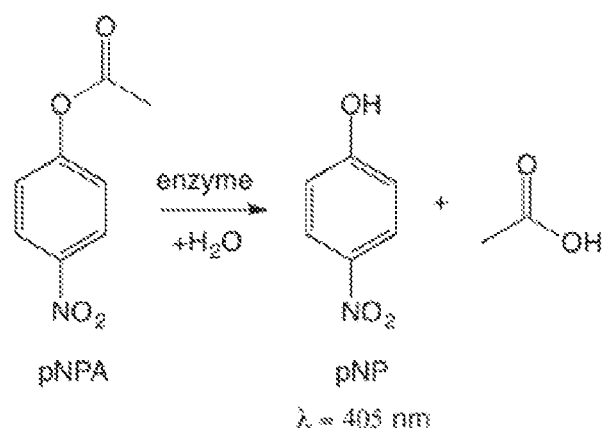
Figure 5:
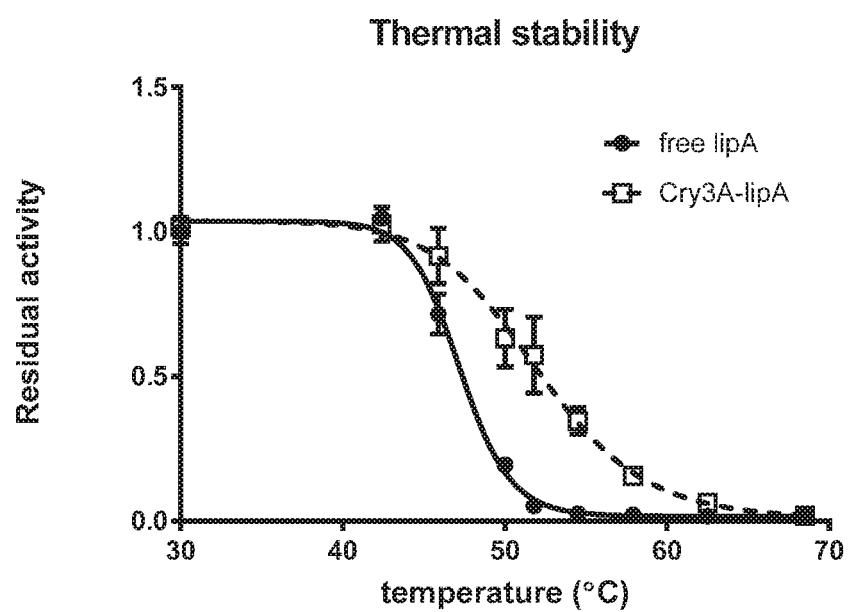
Figure 6A:
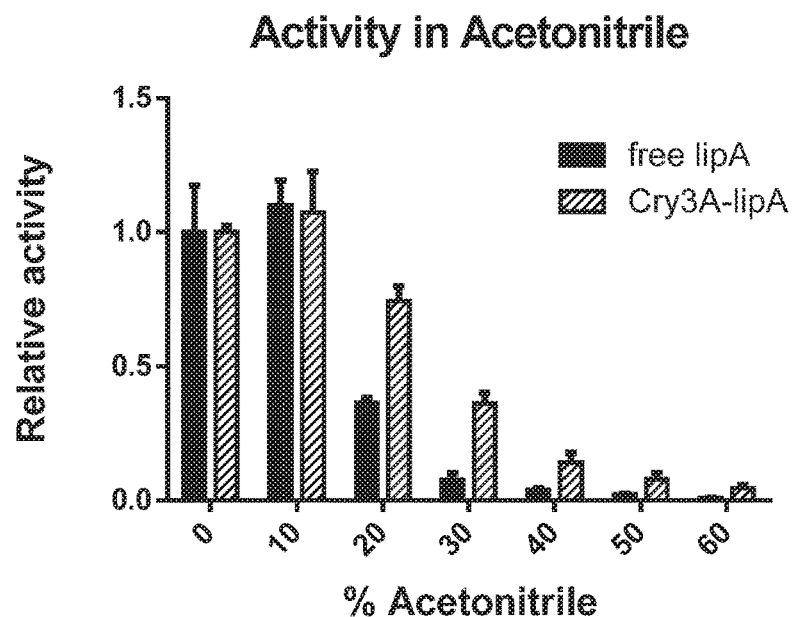
Figure 6B:
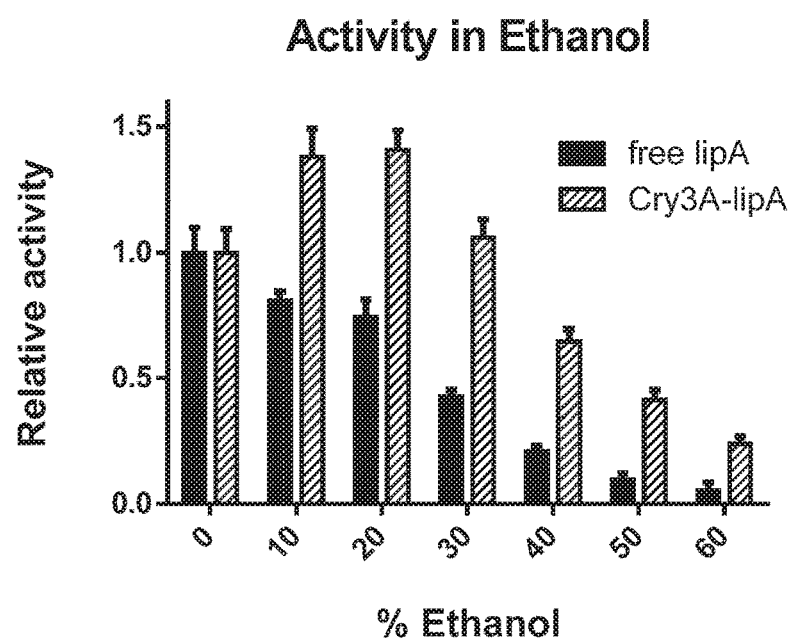
Figure 7:
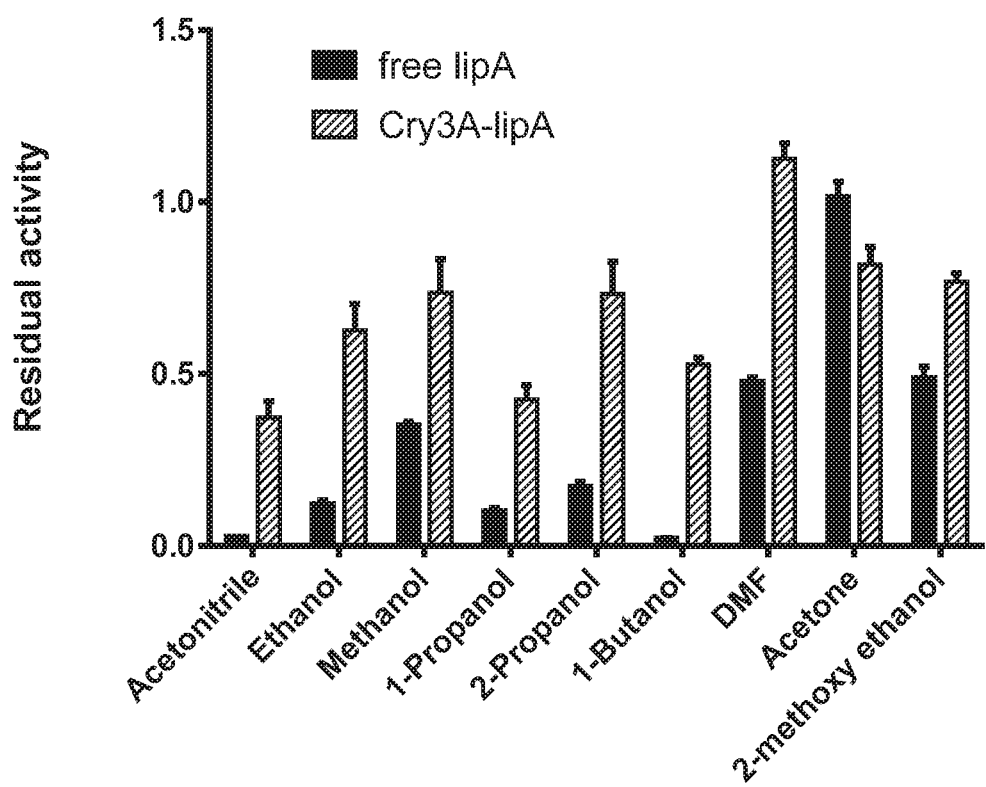
Figure 8:
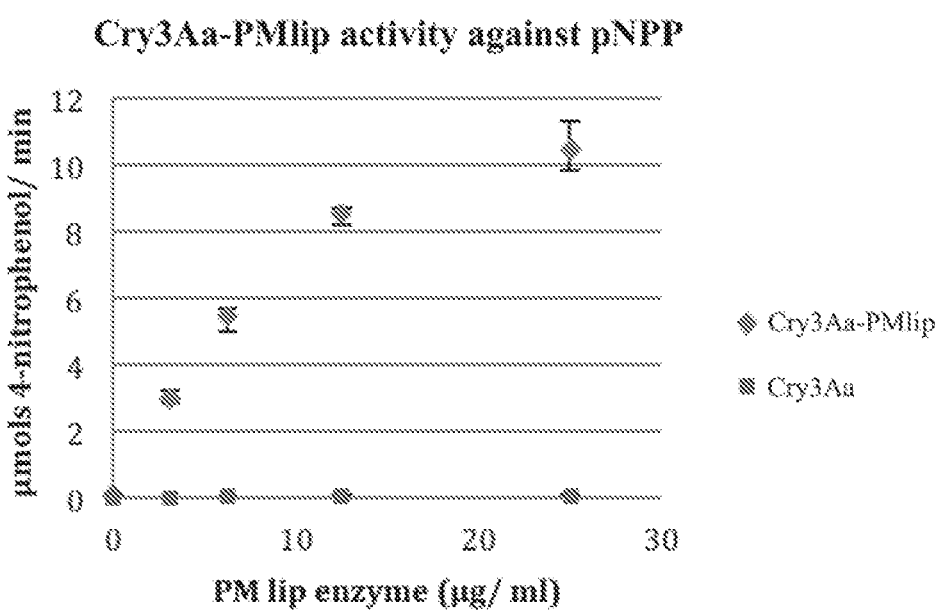
Figure 9:
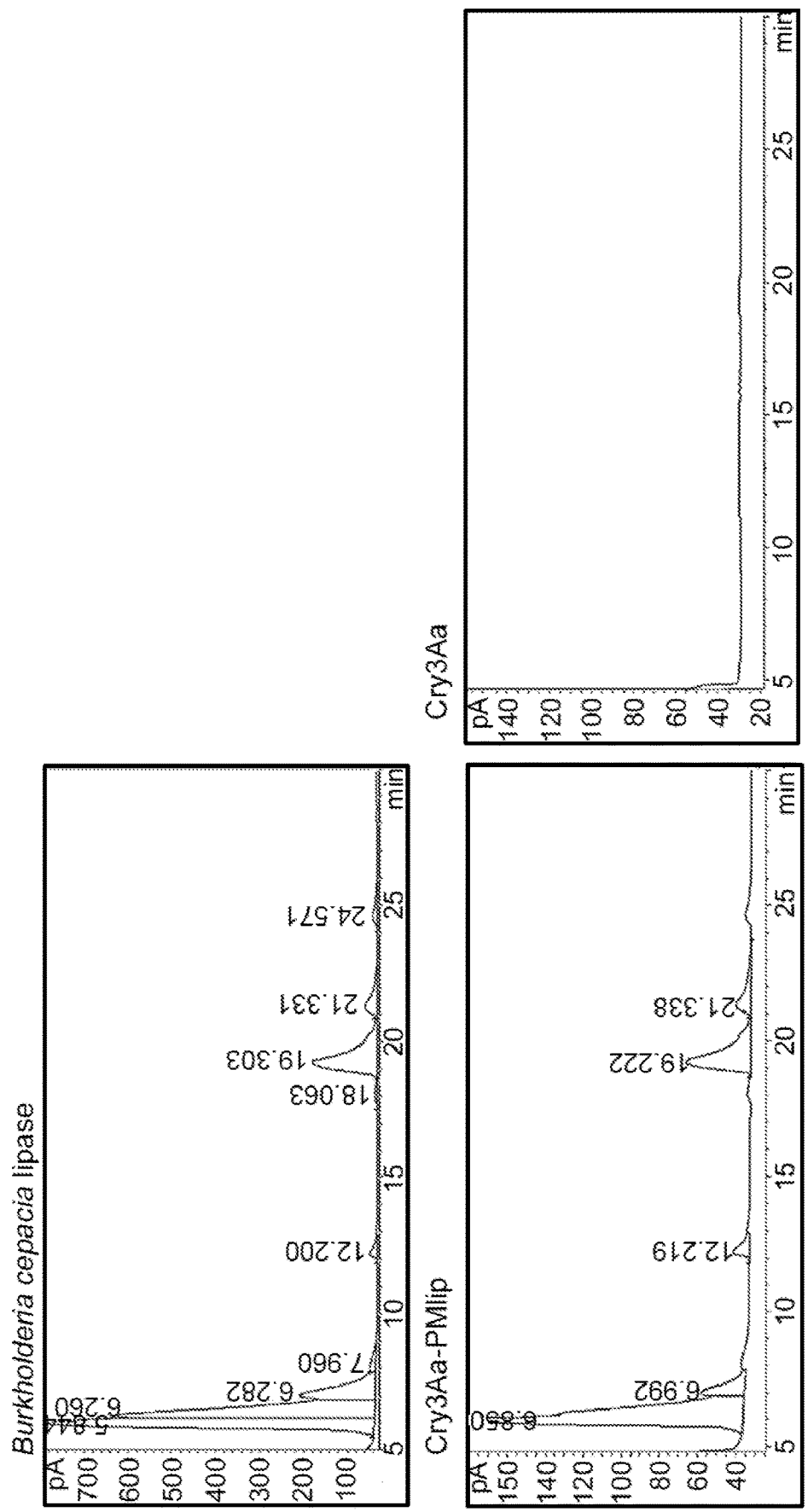
Figure 11:
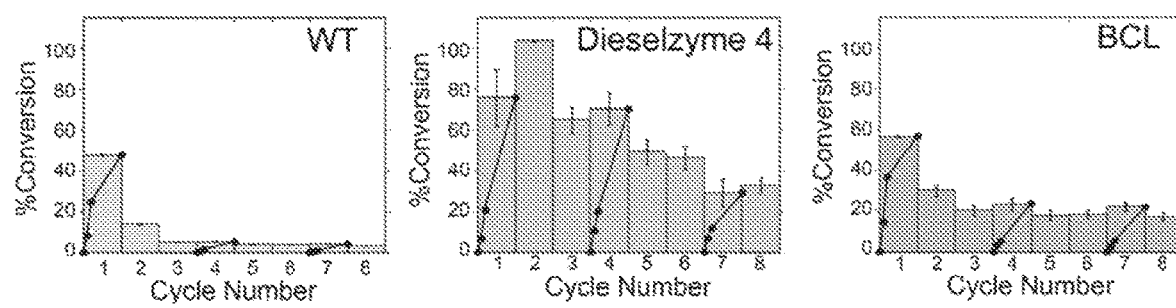
Figure 12:
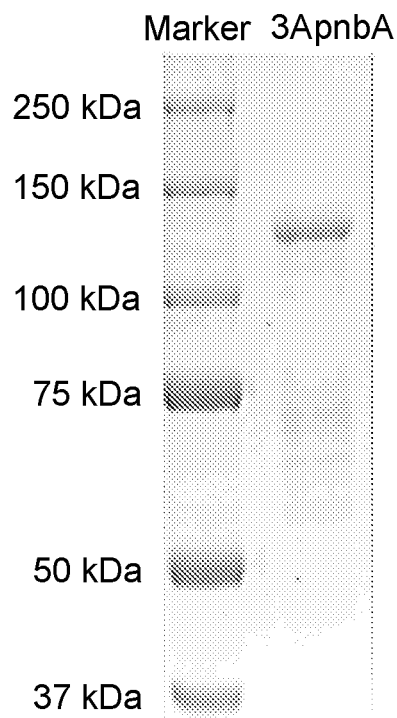
Figure 13:
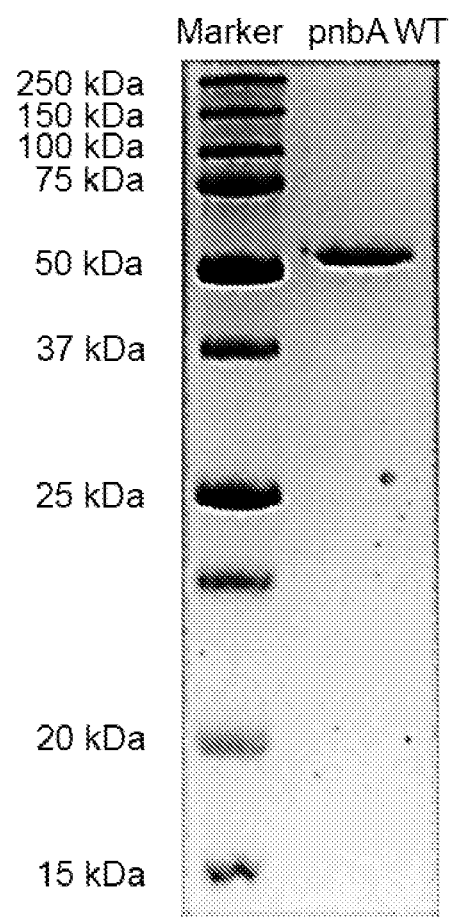
Figure 14A:
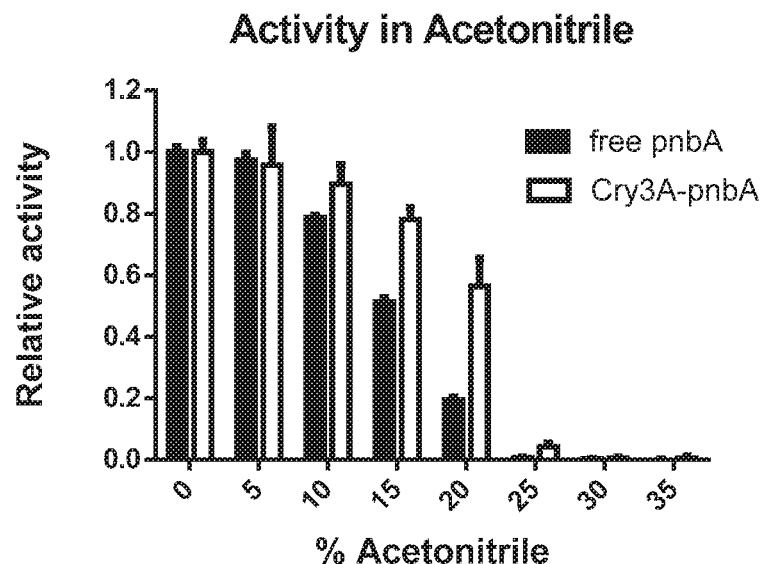
Figure 14B:
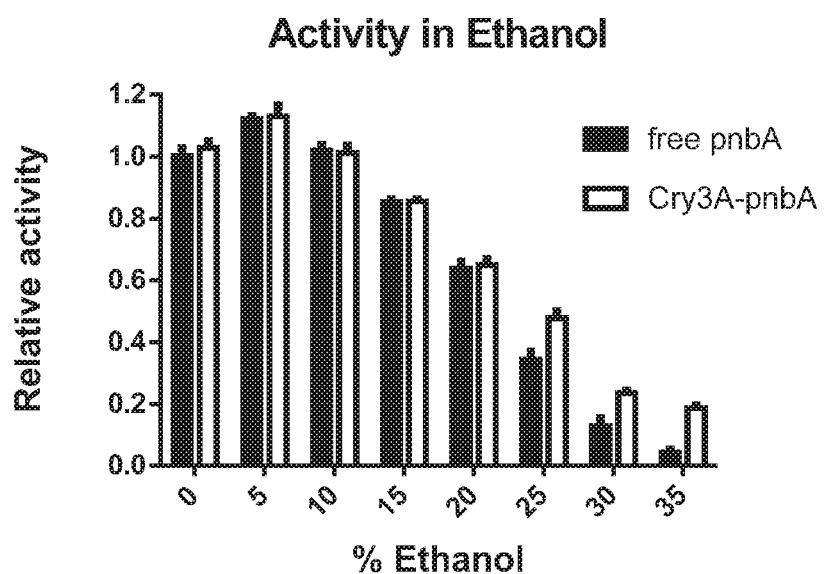
Figure 15:
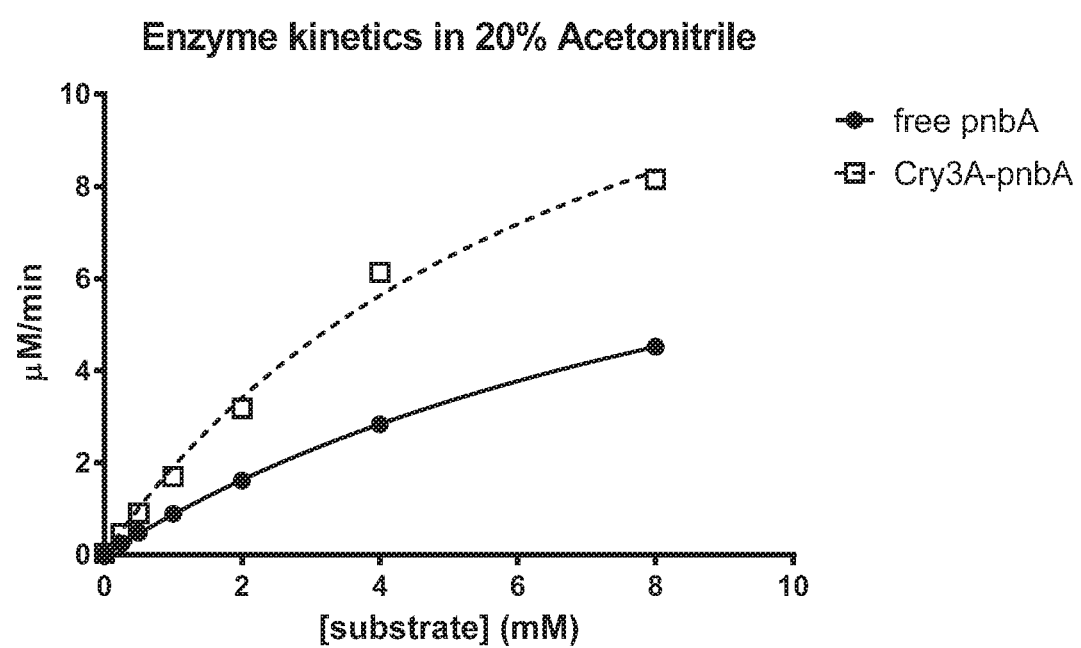
Figure 16:
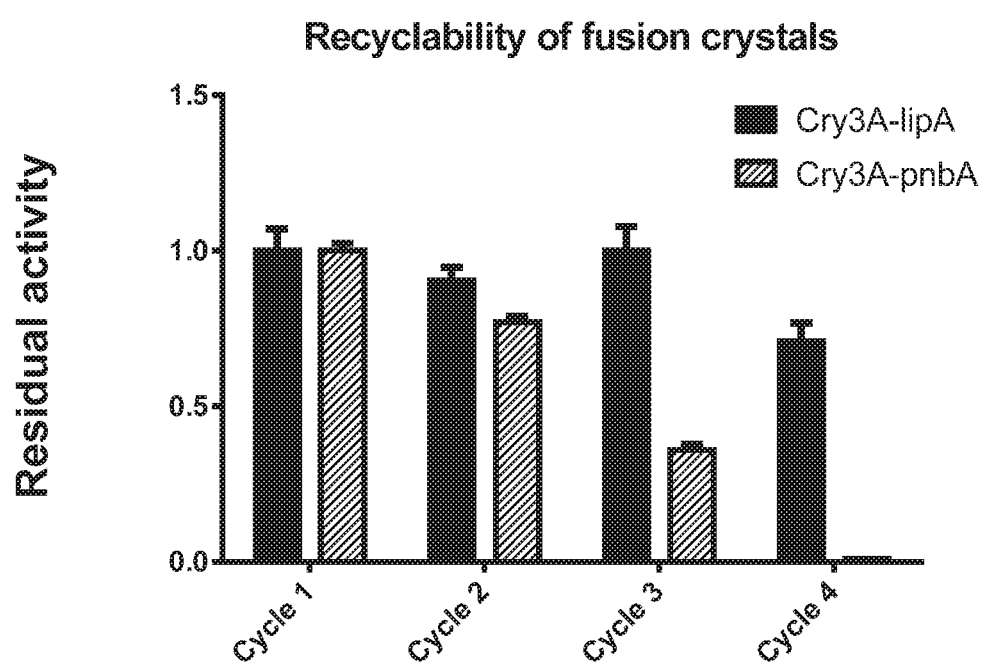
Figure 17:
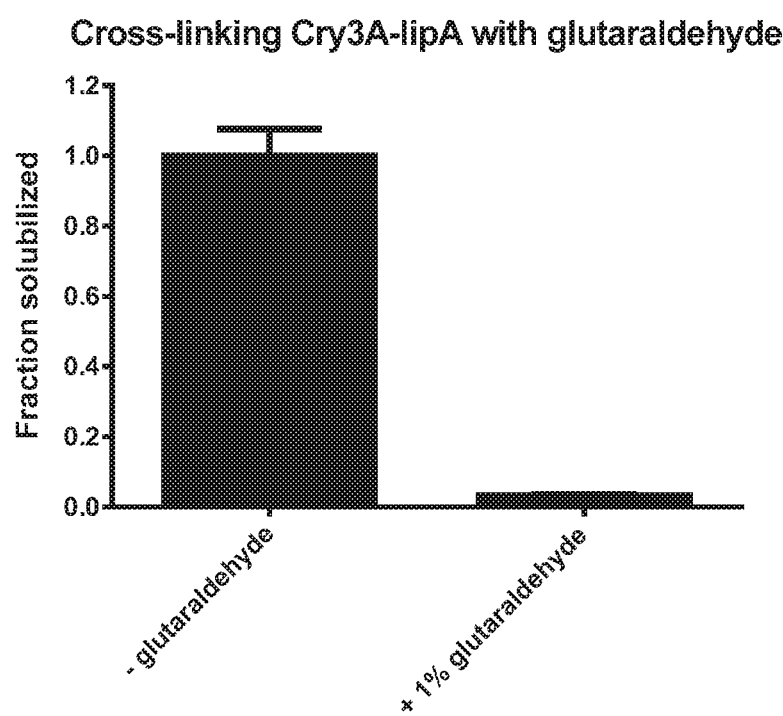

In recent years there has been growing interest in green chemistry, the development of novel processes that reduce the production of hazardous chemicals and waste that are harmful to the environment. Given this impetus, one direction that many chemical companies are exploring is the increased use of enzymes for industrial syntheses given their high reactivities, excellent regio- and enantio-specificities, and low toxicity to natural ecosystems. Enzyme biocatalysts are known to catalyze a diverse set of reactions allowing for their use in the synthesis of a wide range of compounds ranging from enantiomerically pure pharmaceuticals (1) to alternative fuels such as biodiesel (2).

One limitation of enzymes as biocatalysts, however, is their potential instability. Enzymes in their native form can be rendered catalytically inactive by organic solvents and high temperatures, limiting their scope of application. With the advent of recombinant DNA technology, biomolecular engineering techniques such as site directed mutagenesis (3), directed evolution (4) and library generation by gene shuffling (5) have contributed to the development of enzymes stable to high temperature and/or organic solvents. Many classes of enzymes including lipases (6), esterases (4), and proteases (7) have been subjected to directed evolution with large success in stability enhancement compared to their wild-type counterparts.

Immobilization of Biocatalysts

A major hurdle to the practical application of enzymes as industrial catalysts is the cost of production and useable lifetime. While biomolecular engineering techniques can be used to improve enzyme stability, these methods do not necessarily facilitate rapid production and isolation, particularly when high purities are required. A cost-effective biocatalyst should be able to be recycled over many reaction cycles, with minimal loss of activity. One common approach to resolve these issues is enzyme immobilization. This method allows enzymes to be filtered and reused in subsequent reaction cycles, and prevents the enzyme from mixing with the desired product. Immobilization can also augment the thermostability, and in some cases organic solvent tolerance, by limiting an enzyme's conformational flexibility that would otherwise occur in solution (8). This rigidity also contributes to mechanical stability, a requirement for use in large scale reactors where these enzymes would be constantly agitated (9).

Traditional enzyme immobilization techniques involve the covalent attachment of the enzyme biocatalyst to a solid support. This results in 90-99% of the biocatalyst composite being inactive thus lowering the catalytic productivity per weight (10). Furthermore, covalent attachment adds an additional production step, which translates to additional costs and can lead to a reduction in catalytic activity. As such, more advanced approaches to enzyme immobilization are being explored and developed—particularly those that do not involve a separate solid carrier.

Crosslinked Proteins as Immobilized Biocatalysts

Given this interest, one strategy that has been explored involves engineering the enzyme itself to be the particulate, such as the crosslinked enzyme crystals (CLECs) (11), CLECs are produced by isolating the desired enzyme biocatalyst, crystallizing it by addition of a precipitating agent (e.g. high salt, PEG), and then crosslinking it with an appropriate reagent (e.g. glutaraldehyde) to produce a stable and active composite. CLECs have been shown to exhibit enhancement in enzyme thermostability, and organic solvent tolerance for catalysis, as well as improved mechanical stability, rigidity and resistance to proteolytic degradation (12, 13). The major drawback that has limited the broad application of CLECs in industrial syntheses has been the laborious crystallization step that requires very pure protein, and multiple rounds of optimization with no guarantee of being able to crystallize the desired protein in question.

An alternate approach developed by Sheldon and coworkers involves skipping the crystallization step, and preparing the immobilized biocatalyst by aggregating the enzyme using a precipitant followed by successive crosslinking soaked with glutaraldehyde (14). They found that these crosslinked enzyme aggregates or CLEAs were active and stable in organic solvents during the synthesis of ampicillin by penicllin G acylase (14). This novel immobilization strategy was patented and later commercialized by CLEA Technologies. Today, CLEAs have been applied to many different types of enzymes including amidases, proteases, lipases, esterases, oxidoreductases and nitrilases (15). In recent years, the use of CLEAs in industrial biocatalysis has received increased attention, but there remain specific concerns. First, many conditions must be optimized to produce an active CLEA, including precipitant, crosslinker, and particle size. This process can be laborious and can lead to an inactive product after a tremendous time investment. CLEA particles normally range from 5 μm-50 μm and their sizes are often heterogeneous (8). The larger particles are enzymatically less efficient due to substrate diffusion limitations, limiting their potential activity, while filtering a heterogeneous population remains a challenge.

While the development of other "carrier free" immobilization strategies remains enticing, to the best of our knowledge there has been no new report of such a method in recent years. In this study, the present inventors developed a novel strategy to overcome various problematic issues with the previously known methods with a focused application on immobilizing lipases for biodiesel production.

Cry Proteins for Enzyme Immobilization

Crystal proteins (Cry) such as Cry3Aa are proteins that are directly crystallized within the bacterium *Bacillus thu-* ringiensis (*Bt*) (FIG. 1) (16-18). It was previously illustrated that production of the Cry3Aa fused to GFP or mCherry reporter proteins in *Bt* would yield fluorescent protein crystals indicating that the reporter proteins are folded and functional (FIG. 2) (19). Electron microscopy (FIG. 3) performed on native Cry3Aa crystals and Cry3Aa-GFP crystals showed them to be of identical size, demonstrating that the fusion partner does not disrupt the crystal packing. Unlike typical protein crystals, which can dissolve under changes of condition, the Cry3Aa fusion crystals are stable to a variety of conditions. Most importantly, they remain as crystals around neutral pH 7—the pH optimum for most enzymes and would only begin to solubilize in extremely basic conditions (pH>10). This eliminates the crosslinking step that is required for most enzyme immobilization approaches since Cry3Aa fusion protein crystals remain immobilized under normal reaction conditions.

It has been further established that enzymes like luciferase could be fused to Cry3Aa, with no loss of activity. Since Cry3Aa-luciferase crystals were active, and given that Cry3Aa crystals are very stable, it has been hypothesized that Cry3Aa would serve as a promising platform for enzyme immobilization. The most attractive features of this immobilization approach are the consolidation of the production and immobilization of the target enzyme into a single step, and based on previous fusion protein crystals, can be applied to a wide variety of proteins.

This study seeks to investigate the feasibility of this approach for the production and immobilization of lipases, a class of hydrolase enzymes that in nature hydrolyze mono-, di- and triacylglycerols to glycerol and free fatty acids. Lipases are popular in biotechnology because they can catalyze the hydrolysis or synthesis of ester bonds with high reactivities, and substrate selectivities and enantiospecificities making them attractive catalysts for the synthesis of therapeutics, agrochemicals and cosmetics (20-22). In addition to exploring the feasibility of the production methodology, the impact of Cry crystal incorporation on thermostability and organic solvent tolerance is also studied.

Results and Discussion

Production and Activity of Cry3Aa-lipA

The initial studies have focused on a construct comprised of Cry3Aa fused to *Bacillus subtilis* lipase A (lipA). This enzyme made an attractive first target because not only had lipA been used as a biocatalyst for the production of enantiopure cyclohexane-trans-1,2-diols (23), the lipA-producing bacteria, *Bacillus subtilis* (*Bs*), is a close relative of *Bacillus thuringiensis* (*Bt*). Thus it was expected that the *Bs* lipA would fold and function properly in *Bt* without codon optimization. Additionally, while previous reports have observed that the formation of insoluble aggregates in model organisms like *E. coli* can lead to decreased yields (24), this would not be a concern for the Cry3Aa-lipA fusion protein since it should form a solid crystal in *Bt,* which is insoluble but well-ordered. It was therefore hypothesized that there should be minimal loss of active enzyme during production.

The lipA gene was fused to the C-terminus of Cry3Aa using traditional molecular biology techniques. A plasmid containing this construct was transformed into *Bt,* and the Cry3Aa-lipA crystals could be produced and isolated as described previously (19). Of note was the high yield of Cry3Aa-lipA crystals—on average 100 milligrams per litre which made the production of the fusion protein crystals extremely robust. The Cry3Aa-lipA crystals were shown to be active according to an assay based on the substrate p-nitrophenyl acetate (pNPA) (Sigma), which upon hydrolysis forms the yellow product p-nitrophenol (pNP) with an absorption peak at 405 nm (FIG. 4). All absorbance measurements were performed in a 96 well plate on a Tecan Infinite M1000 Pro.

Thermostability of Cry3Aa-lipA

With the lipase activity of the Cry3Aa-lipA established, the impact of Cry3Aa-derived immobilization on lipA's thermostability was then determined. Cry3Aa-lipA crystals were produced in high yield (~100 mg/L) using the *Bt* expression system. For comparison, the wild-type lipA enzyme (free lipA) was expressed utilizing an N-terminal histag, or using the pETSUMO system to produce untagged enzyme. Both forms of free lipA have similar activities and stabilities (data not shown). It is worth noting that the yields of lipA protein were relatively low (2-5 mg/L) due in part to the protein precipitation. These data highlight one potential advantage of the Cry3Aa fusion immobilization approach—biocatalyst yield.

The thermostabilities of the Cry3Aa-lipA and free lipA were determined by heating for 1 hours in a PCR block at different temperatures and then measuring the residual activity in triplicate, and normalizing each to their respective activities at 30° C. The results, shown in (FIG. 5), indicate that the Cry3Aa-lipA crystals are more thermostable than the wild-type enzyme. The Cry3Aa-lipA crystal $T_m$ (temperature of residual 50% activity) of 52° C. is 5° C. higher than the free enzyme.

Organic Solvent Tolerance of Cry3Aa-lipA

One commonly observed feature of immobilized enzymes is their increased tolerance to organic solvents. To assess the robustness of the Cry3Aa-lipA crystals, its activity was tested and compared to that of the purified lipA protein under two scenarios: 1) at increasing concentrations of two common organic solvents, and 2) over a long incubation time in various 50:50 aqueous organic solvent mixtures. Under the former scenario, the lipase activity with pNPA was monitored in increasing concentrations of acetonitrile (ACN) and ethanol (EtOH) in triplicate and normalized to their activity at 0% solvent. The data confirm that Cry3Aa-lipA crystals exhibit higher-level organic solvent tolerance as a function of concentration than the free lipA enzyme for both organic solvents tested (FIG. 6). Significant differences were observed under 30% solvent, where the Cry3aA-lipA crystals were 4.7-fold and 2.5-fold more active than free lipA in ACN and EtOH respectively.

The data in FIG. 6 provide insight into the lipase activity as function of concentration after a fixed time, but does not describe the stability of the lipase in aqueous organic solvents over time. Since long-term stability of the biocatalyst is a key consideration in reaction cycles which take some time to reach completion, the long-term stability of lipA was studied in aqueous organic solvents over time by incubating Cry3Aa-lipA crystals and lipA enzyme in 50% various organic solvents and measuring the residual activity after 24 hours. The data provided in FIG. 7 show that Cry3Aa-lipA crystals are much more stable than free lipA enzyme measured over a 24 h period for nearly all solvents tested. Based on these data, it is concluded that the Cry3Aa framework is well suited for stabilizing lipA for long-term stability in organic solvents.

Methods and Further Studies

Cry3Aa for Facile Immobilization of Biodiesel Lipases

Given the promising results obtained for Cry3Aa-lipA, further studies are to be conducted to determine whether this methodology would be suitable for industrial relevant lipases, such as those used for biodiesel production. Biodiesel is an alternative fuel that can be produced from the transesterification of common vegetable oils with methanol (2, 25). It is relevant to geographic areas where soybean, canola and related vegetable oils are common waste byproducts produced by the many restaurants and food factories. The recycling of these cooking oils to fatty acid methyl esters (FAMEs) would be beneficial as the resulting FAME biodiesel could be used to power medium- to heavy-sized vehicles and vessels in the commercial sector, while its recycling could help to reduce the disposal of waste oils in landfills.

Currently, the industrial recycling of vegetable oil to biodiesel is dominated by chemically mediated acid or base catalyzed reactions, but recently the use of lipase biocatalysts has gained increasing interest. Lipases from *Candida antarctica* (*Ca*) and *Proteus mirabilis* (*Pm*) have been demonstrated to produce FAMEs (26, 27). Thus it will be explored whether this Cry3Aa technology can produce the immobilized forms of these lipases that are active. The first step will be to fuse the *Ca* or *Pm* lipase genes to cry3Aa and express the resultant gene fusions in *Bt* for crystal production. The activity of each Cry3Aa-lipase fusion will be tested against the lipase substrate p-nitrophenyl palmitate (pNPP), which works similarly to pNPA (FIG. 4) but has a longer fatty acid chain that better mimics the fatty acids found in biodiesel.

some preliminary experiments have been performed to confirm the general feasibility of this approach. The *Pm* lipase gene was successfully fused to Cry3Aa, and the resulting fusion construct Cry3Aa-PMlip was produced. Importantly, Cry3Aa-PMlip crystals were confirmed to exhibit activity against pNPP (FIG. 8), while the incubation of canola oil with Cry3Aa-PMlip yielded a similar profile to that for the commercially available *Burkholderia cepacia* lipase (Sigma), a known biodiesel lipase (FIG. 9).

Exploring the Impact of Cry3Aa Crystal Immobilization on the Thermostability of Biodiesel Lipases As mentioned above, it has already been demonstrated that *Pm* lipase (PMlip) immobilization as a Cry3Aa fusion protein crystal results in an active catalyst. These experiments will be repeated for the *Candida antarctica* lipase (CAlip). The next step will be to examine their thermostabilities relative to the wild-type enzymes. The lipases from *Candida antarctica* (*Ca*) and *Proteus mirabilis* (*Pm*) will be expressed and purified as described in (24, 27), respectively. Cry3Aa fused *Ca* lipase (Cry3Aa-CAlip), free *Ca* lipase (CAlip), Cry3Aa fused *Pm* lipase (Cry3Aa-PMlip) and free *Pm* lipase (PMlip) with equivalent reaction rates will be heated in a PCR block at various temperatures (25° C.-90° C.) for 30 minutes and then assayed for their residual activity against pNPP. The experiment will be performed in triplicate in a 96-well plate and the activity will be monitored using a Tecan infinite M1000 Pro. It is expected that the Cry3Aa fused lipases will increase the $T_m$ values relative to the free lipases.

Exploring the Ability of Cry3Aa Crystal Immobilization on the Ability of Biodiesel Lipases to Tolerate Organic Solvents Lipases used in biodiesel production must be resistant to MeOH or EtOH, since they are the likely substrates in the transesterification reaction converting oil to FAME. Therefore, enhancing the MeOH or EtOH tolerance of biodiesel enzymes is advantageous as it can lead to decreased reaction times and increased recyclability. In this regard, the activity of Cry3Aa fused biodiesel lipases will be examined in increasing organic solvent concentrations (ACN, EtOH, MeOH) to ascertain how well these enzymes behave in a given organic solvent. Their activities in high concentrations of the aforementioned organic solvents will also be investigated as a function of time to gain insight into their stability over time.

The experimental design will be similar to the previous organic solvent tolerance studies with Cry3Aa-lipA except that the substrate used will be pNPP. To test activity, concentrations of Cry3Aa-CAlip and free CAlip as well as Cry3Aa-PMlip and free PMlip with equivalent rates of hydrolysis will be subjected to 0%, 10%, 20%, 30%, 40%, 50%, 60%, 70% and 80% of either ACN, EtOH or MeOH. and analyzed for their ability to hydrolyze pNPP. Each experiment will be performed separately in triplicates and the free lipases will be compared to the Cry3Aa immobilized forms. The activities will be monitored in a 96-well plate on a Tecan infinite M1000 Pro. It is expected that the Cry3Aa fusion lipases will retain higher activity in higher concentrations of organic solvent than the free lipases.

To establish organic solvent stability over time, the Cry3Aa-CAlip, Cry3Aa-PMlip and free lipases will be incubated respectively in 0%, 50%, 60%, 70%, 80%, 90% and 100% of either ACN, EtOH or MeOH for up to 48 h. At specific time points aliquots will be taken, diluted to 5-10% given solvent, and analyzed for residual activity against the pNPP substrate. This experiment will be done in triplicates and the results averaged. The activity at each time point will be divided by the maximum activity at t0 (usually with 0% solvent but not always) to give a percentage of activity remaining. It is expected that the data will show the Cry3Aa-lipase fusion crystals retain higher activity than the free lipase enzyme in all organic solvents over time.

Once it is established that the Cry3Aa-mediated immobilization can enhance the organic solvent activity and stability of both biodiesel enzymes, the next step is to evaluate the ability of the Cry3Aa fusion lipases to produce biodiesel, and to maintain stability over multiple reaction cycles against that of the lipases immobilized by traditional techniques. To this end, free PMlip and free CAlip will be covalently immobilized onto hydrophobic oxirane beads as described previously (27). To produce biodiesel, Cry3Aa lipase fusions and oxirane bead immobilized lipases will be incubated with 1.5 ml canola oil and 0.625 ml of a 1:1 ratio of MeOH/EtOH: 0.1M $NaH_2PO_4$ pH 7.0 buffer. The amount of each lipase added will be tailored such that less than 40% conversion occurs over 6 hours. This way the differences in conversion rates for each enzyme will be due to the exposure time to MeOH or EtOH, which is our intention for this aim. After 20 h, the reaction of all immobilized lipases will be washed with hexanes to remove residual fatty acids, followed by water to remove residual glycerol and MeOH/

EtOH. The reaction will then be repeated up to 8 cycles. Gas chromatography (GC) will be used for biodiesel analysis. Aliquots of each reaction will be diluted in hexane containing 0.5 mg/ml heptadecanoate (internal standard) and analyzed by the GC HP 6890 series (Agilent, School of Life Sciences) with a flame ionized detector (FID) equipped with a Select Biodiesel column (30 m×0.32 mm, 0.25 μm, Agilent). The percent conversion will be determined by comparison to a biodiesel sample prepared from canola oil using an excess of *Burkholderia cepacia* lipase (Sigma) (2). It is expected that the Cry3Aa fusion lipases will behave as well as or better than the covalently-modified lipases in terms of maintaining high fatty acid conversion rates over long periods of incubation in MeOH.

Figure 19:
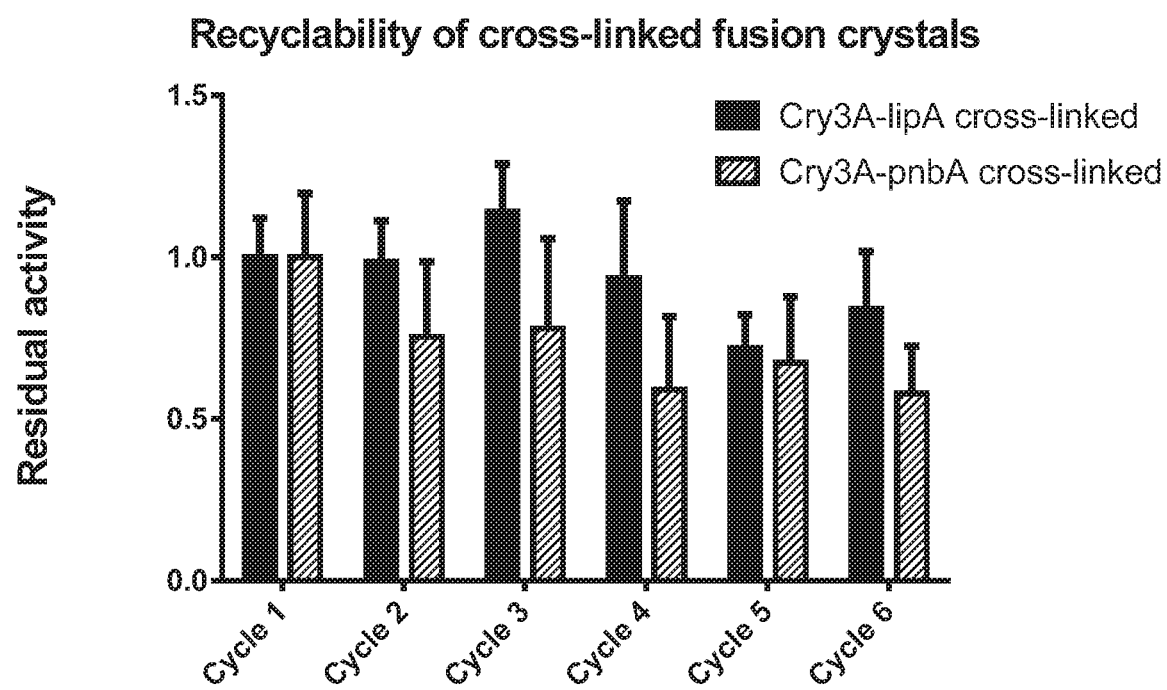
Figure 20A:
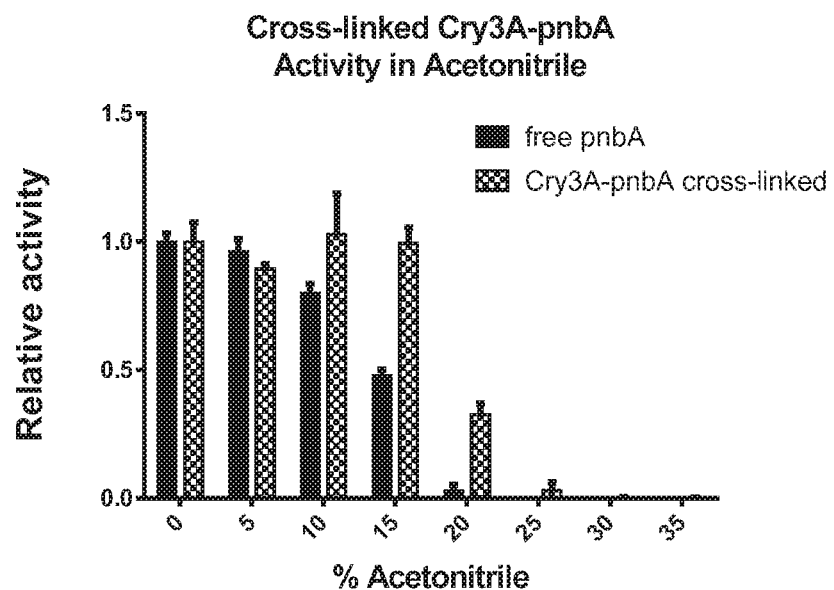
Figure 20B:
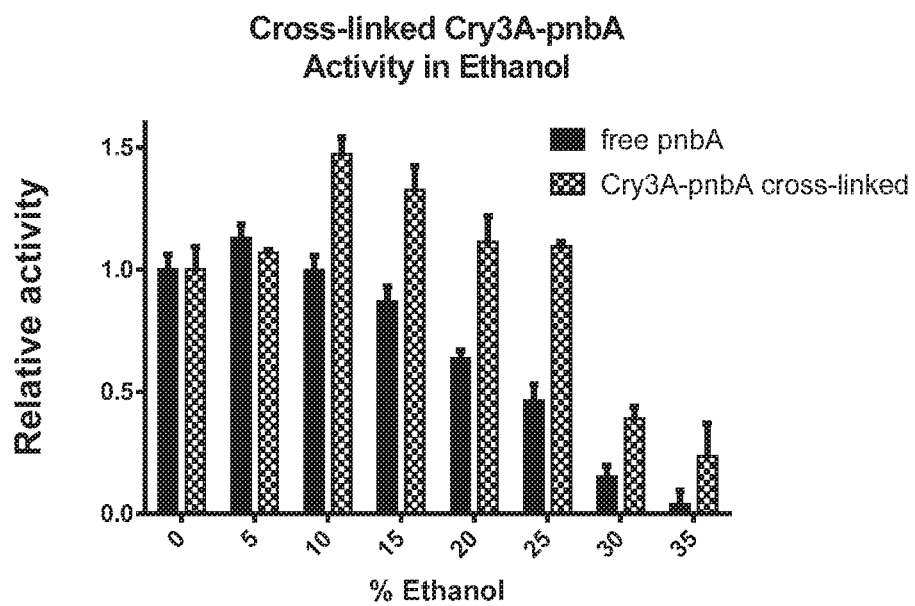
Figure 21A:
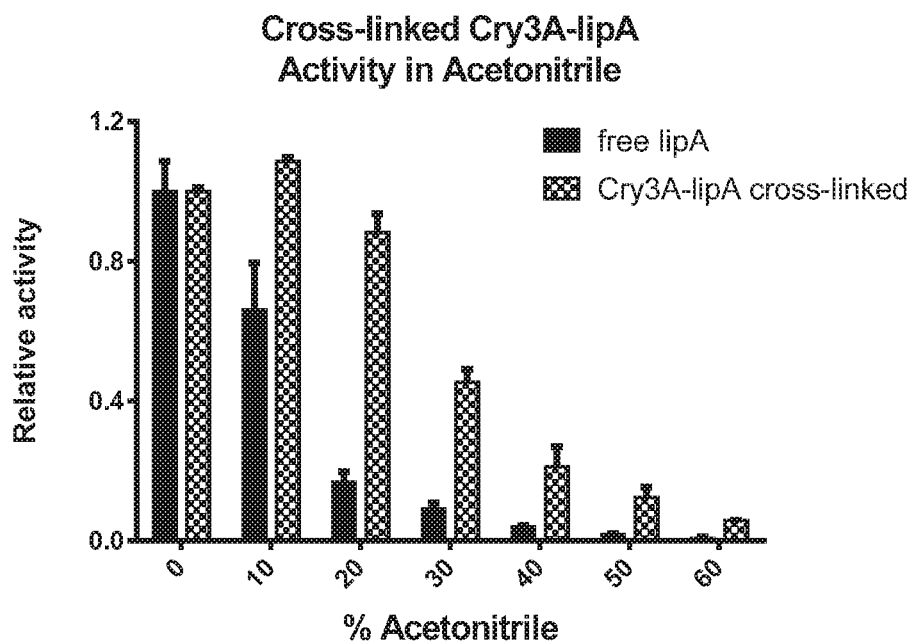
Figure 21B:
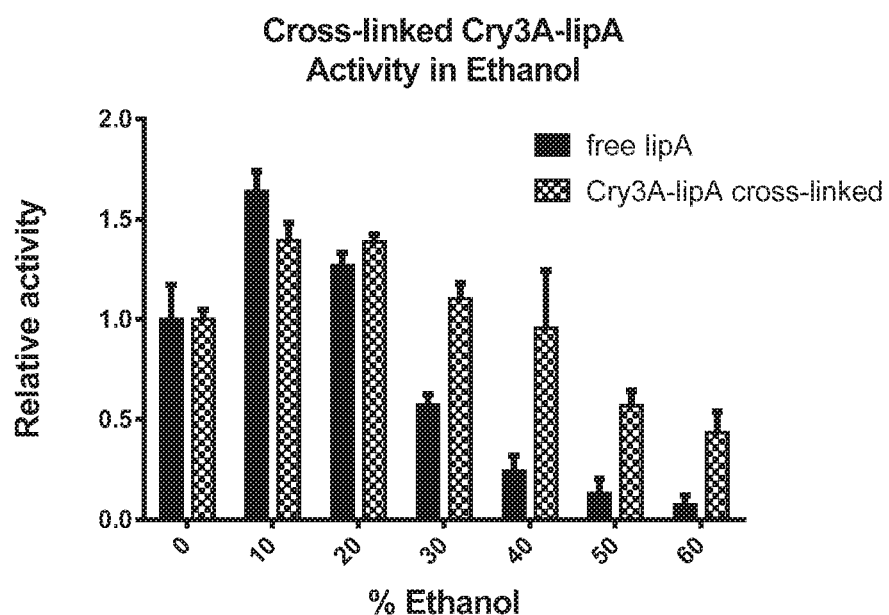
Figure 22A:
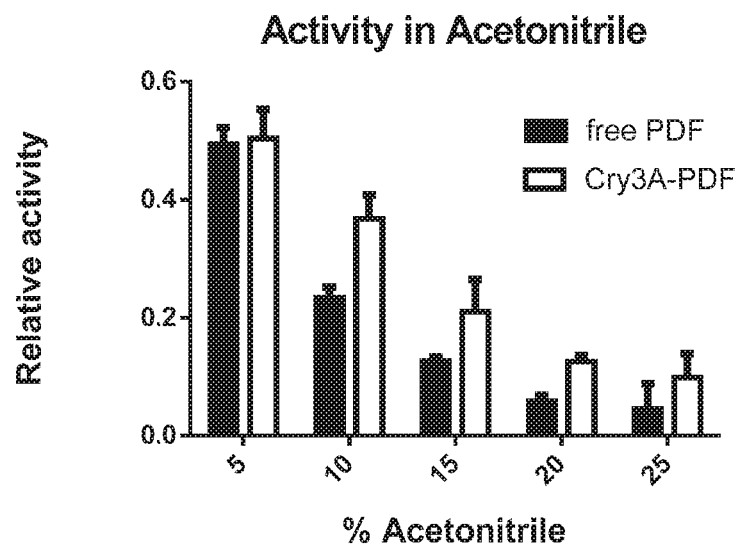
Figure 22B:
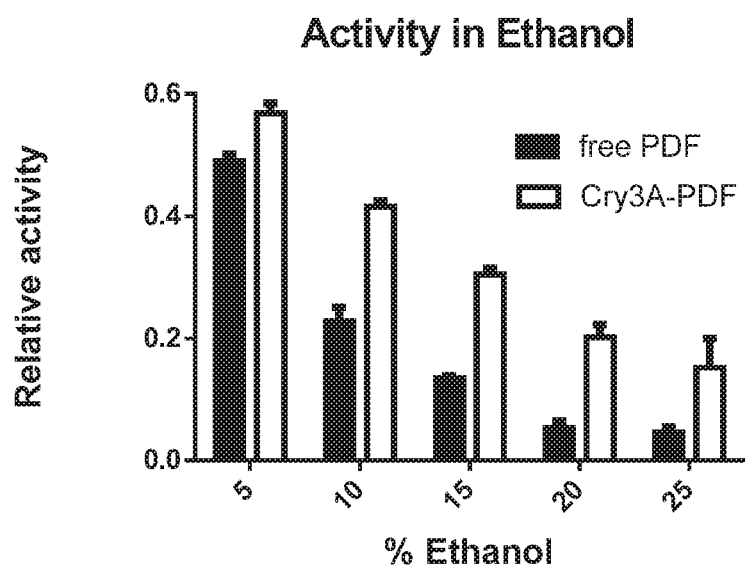
Figure 23:
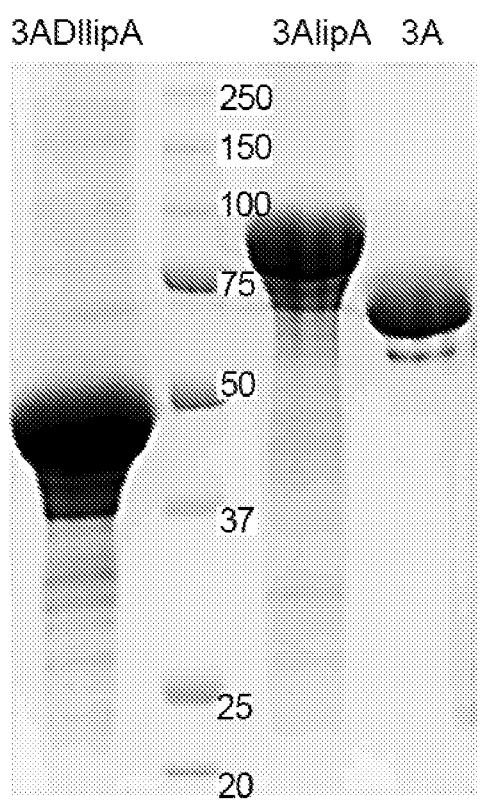
Figure 24A:
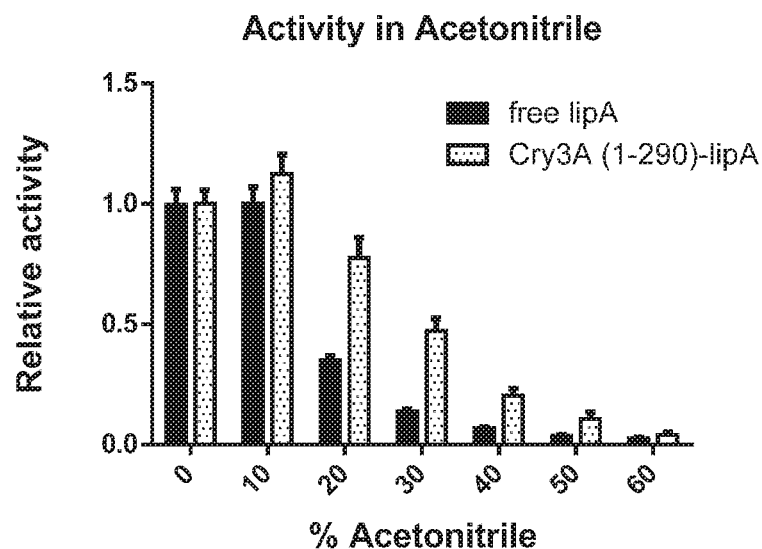
Figure 24B:
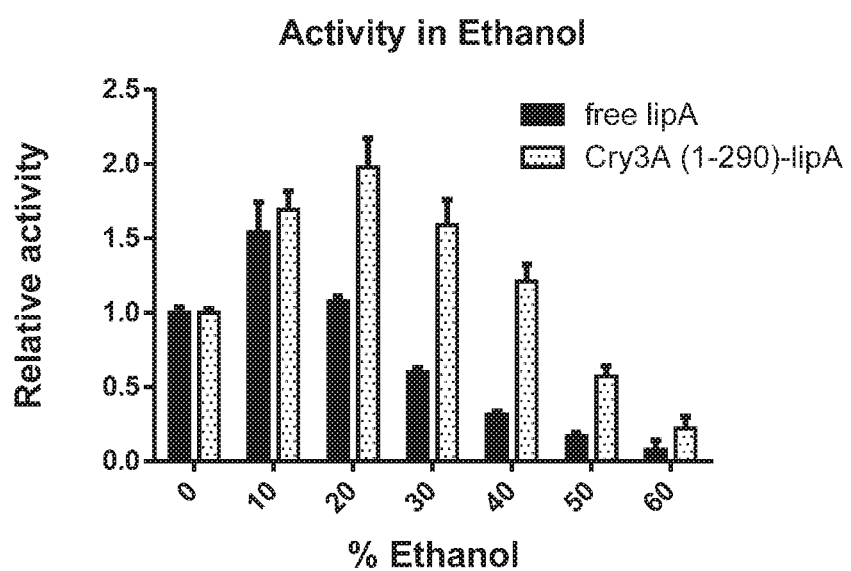
Figure 25:
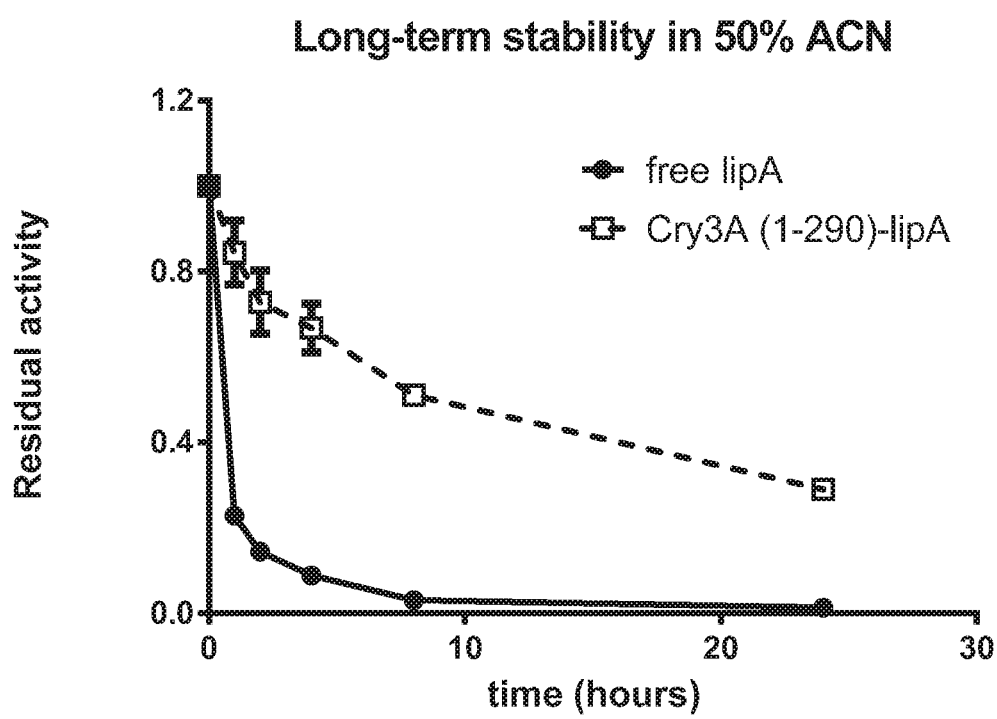
Figure 26:
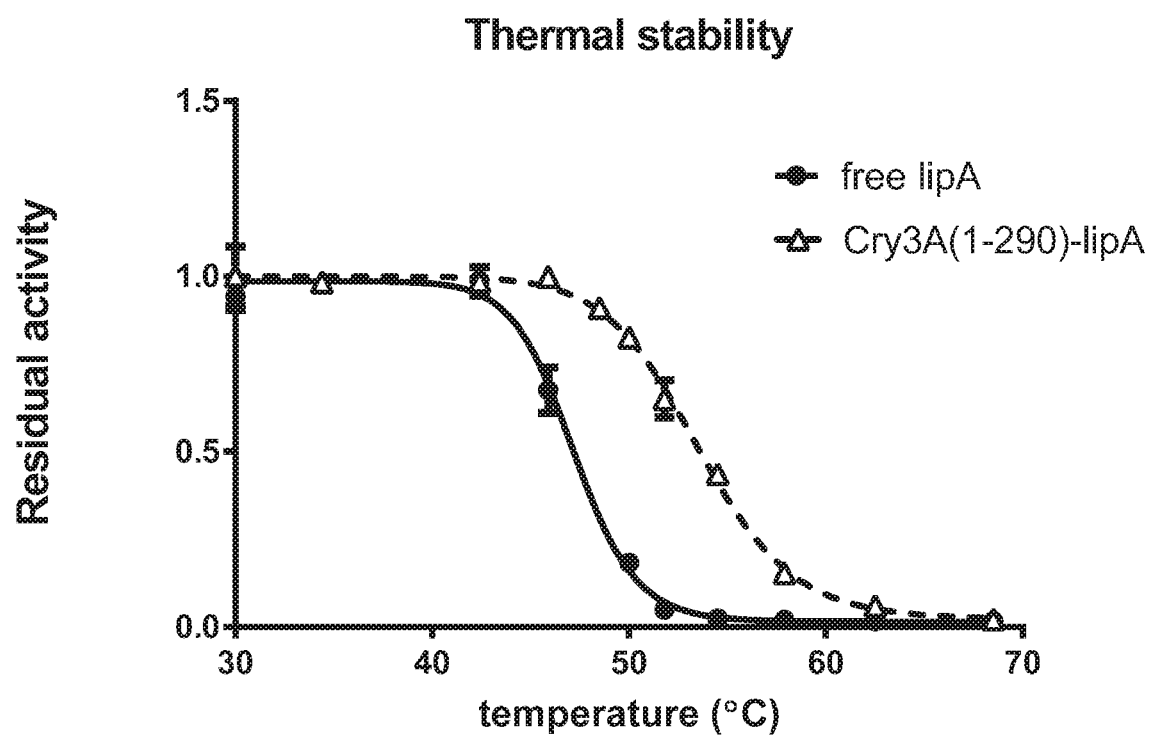
Figure 28:
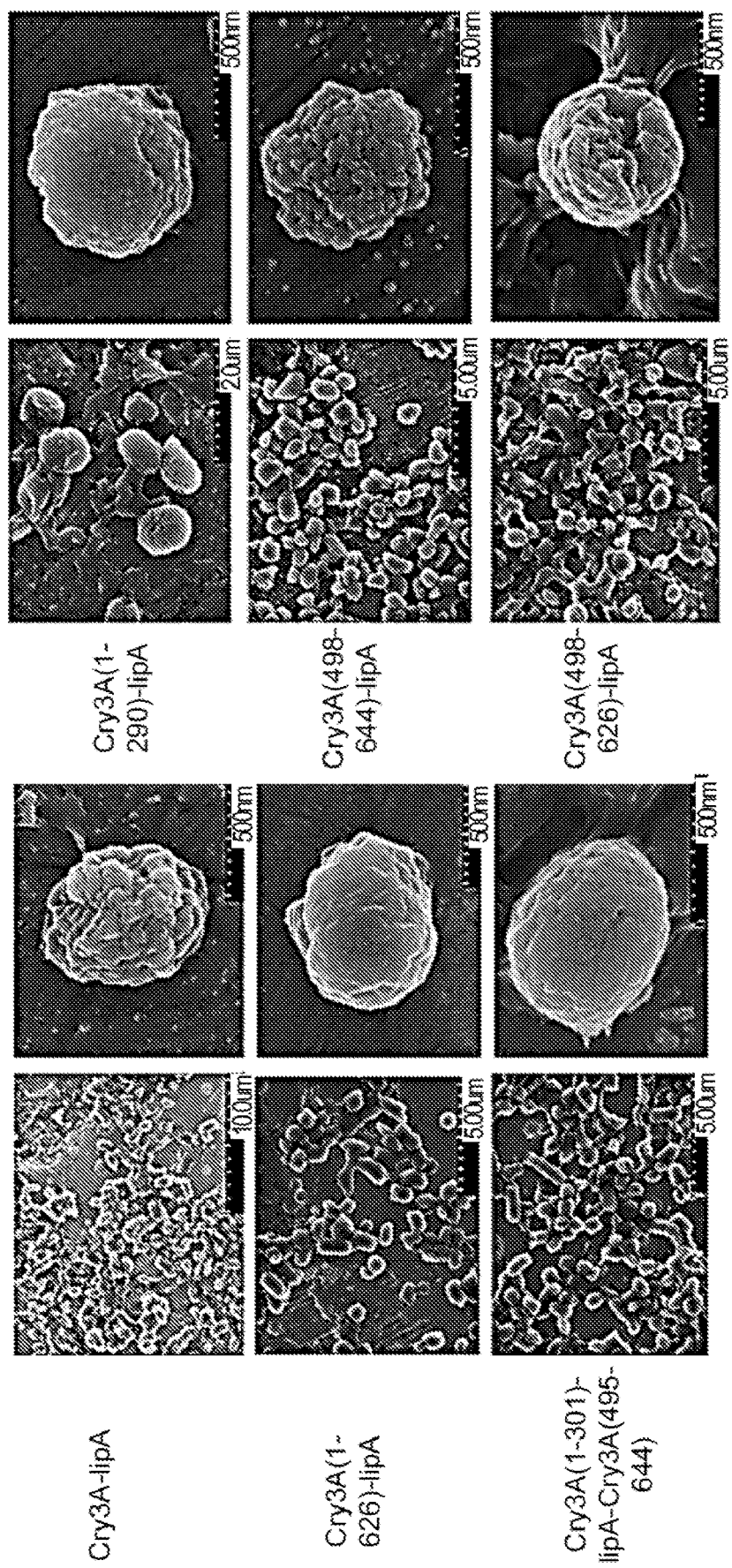
Figure 29:
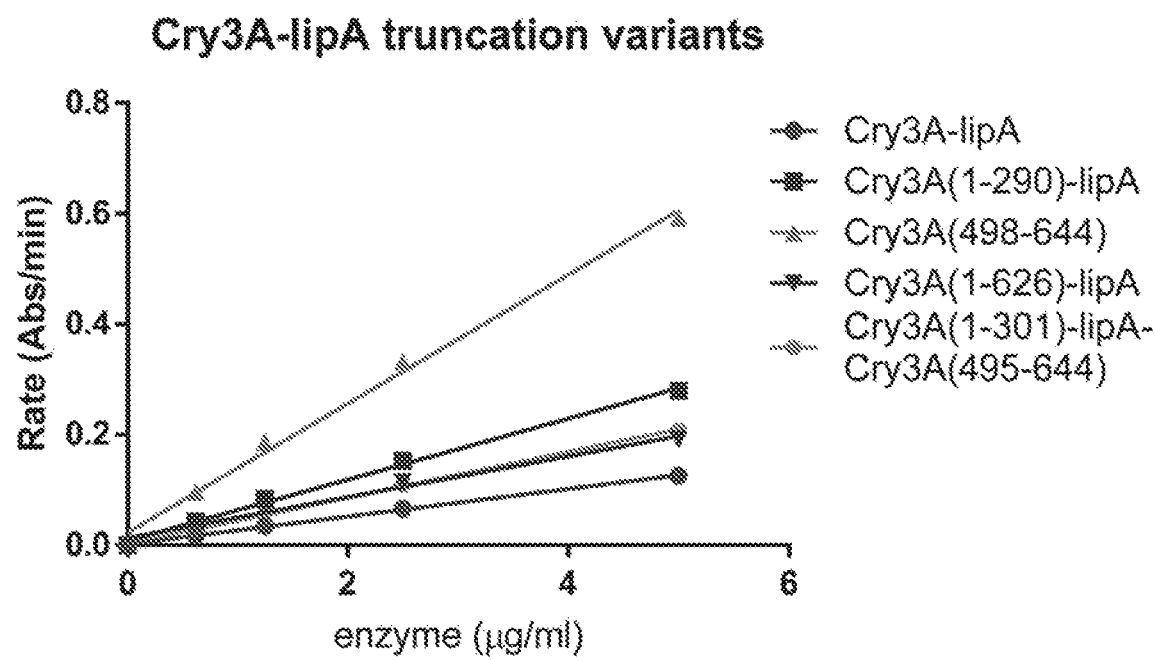
Figure 30:
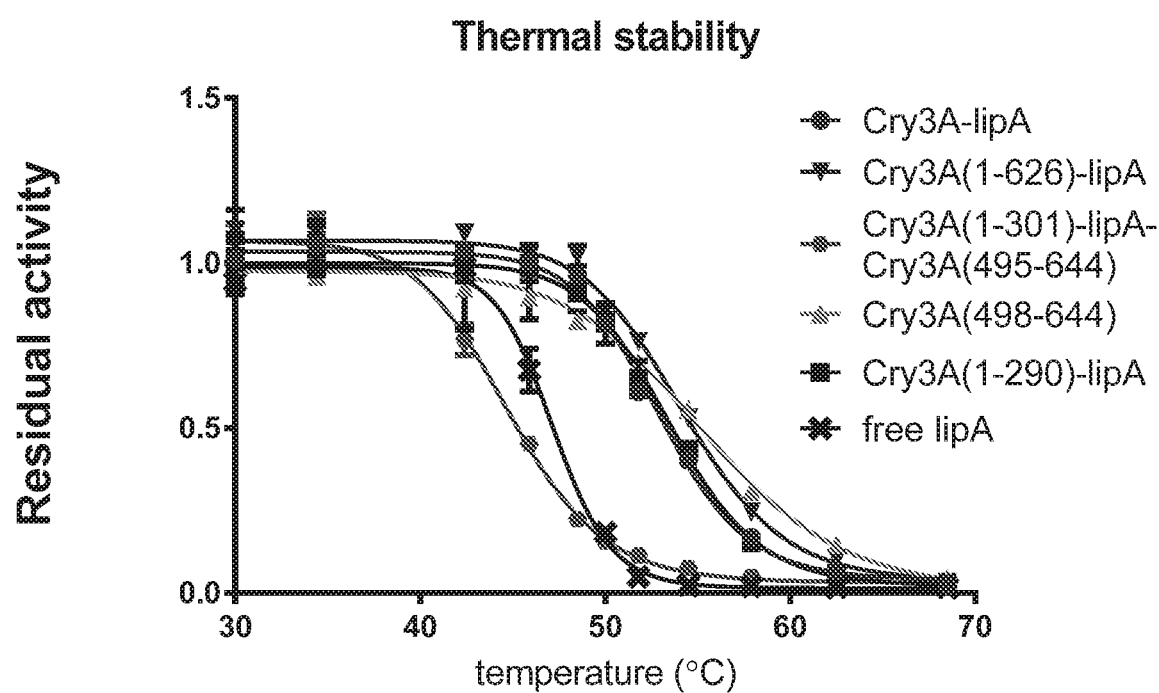
Figure 31A:
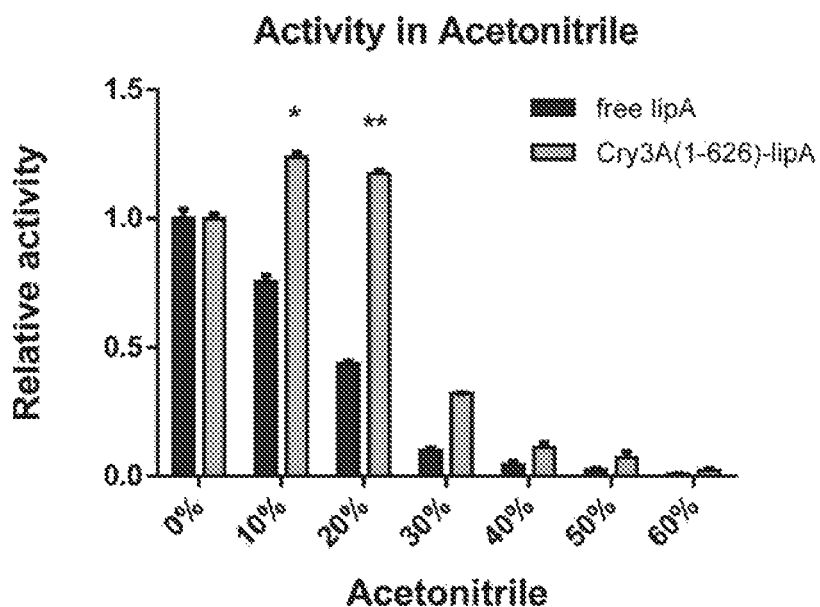
Figure 31B:
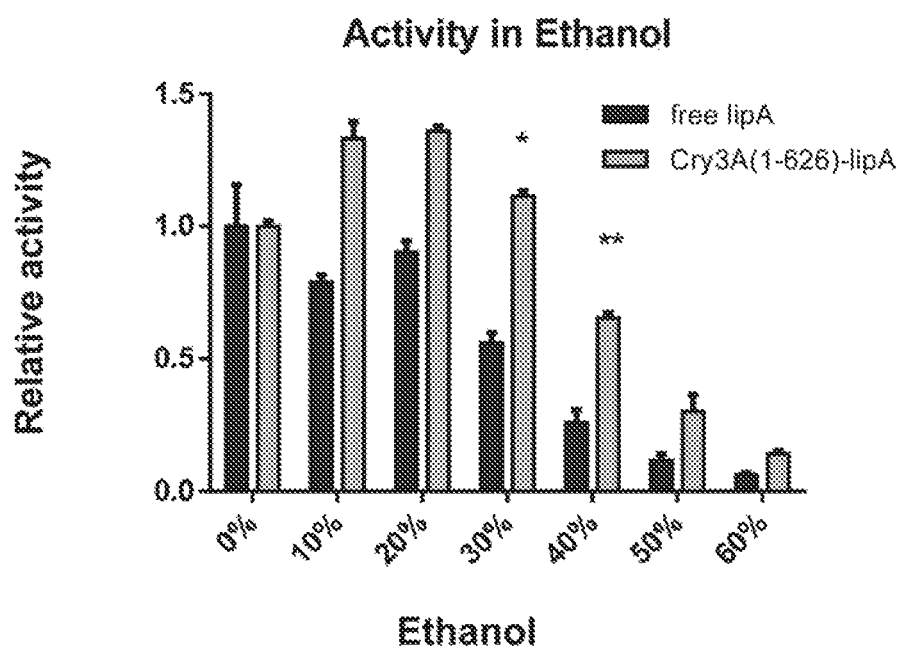
Figure 32:
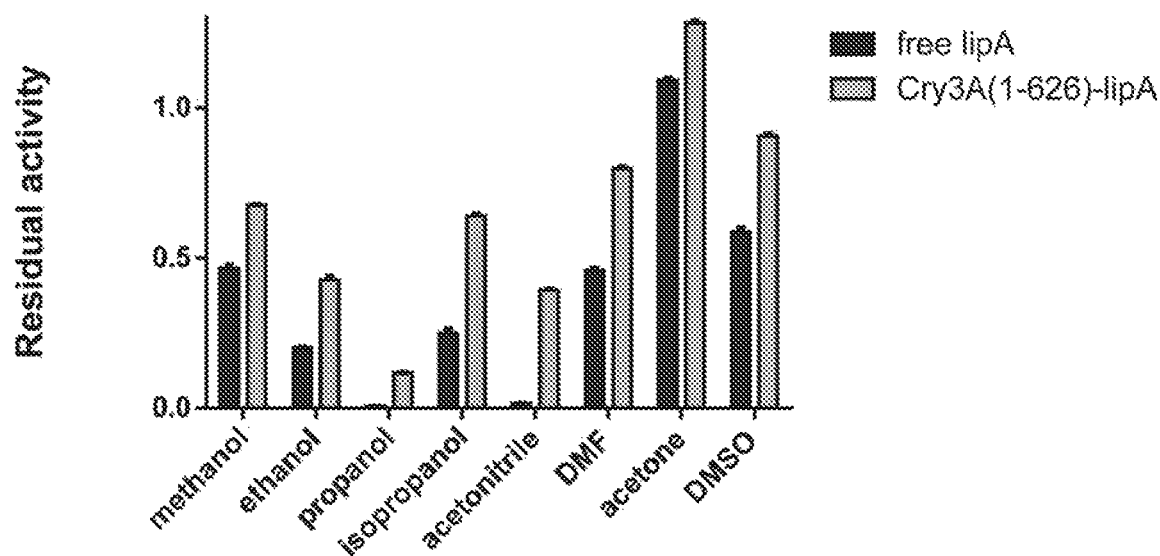
Figure 33:
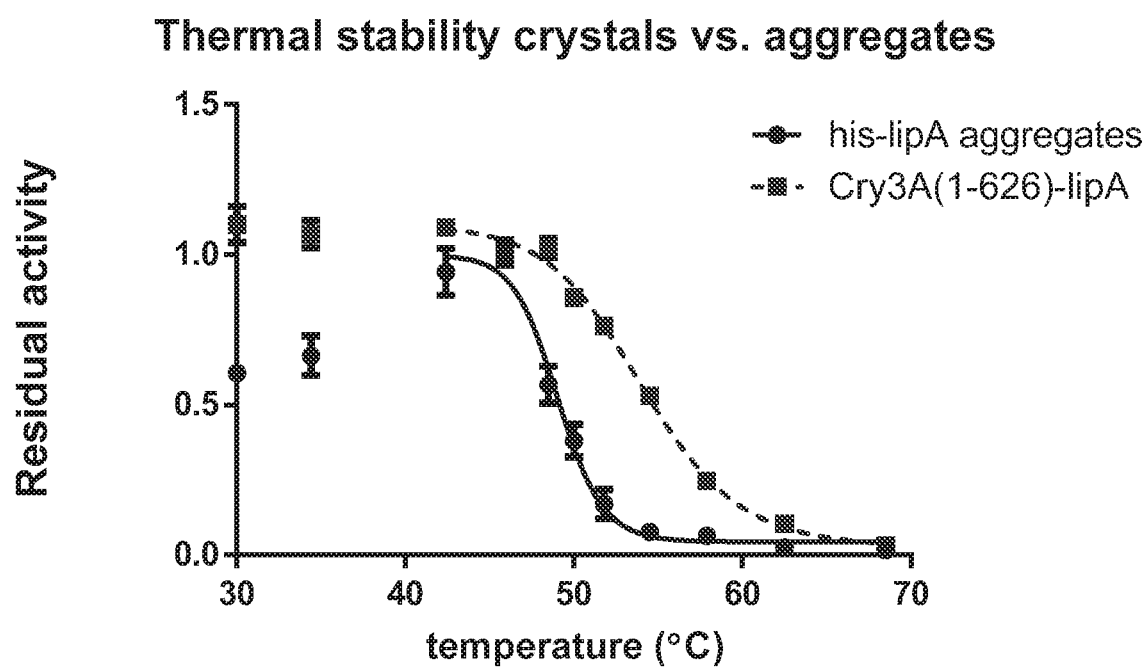
Figure 34:
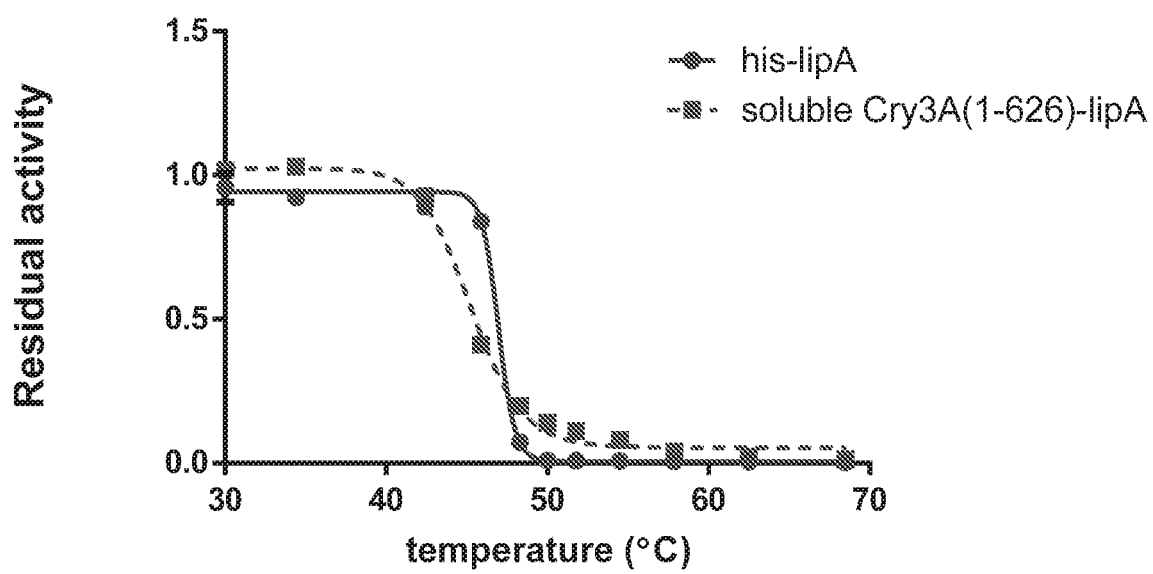
Figure 35:
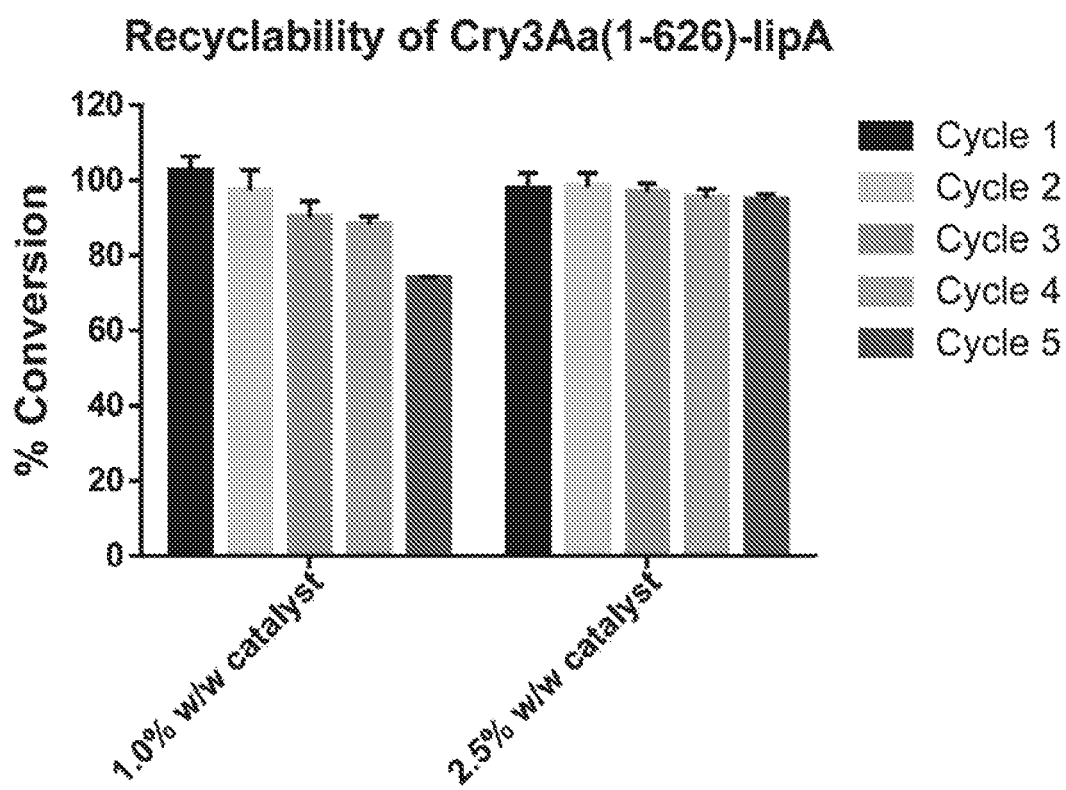
Figure 36:
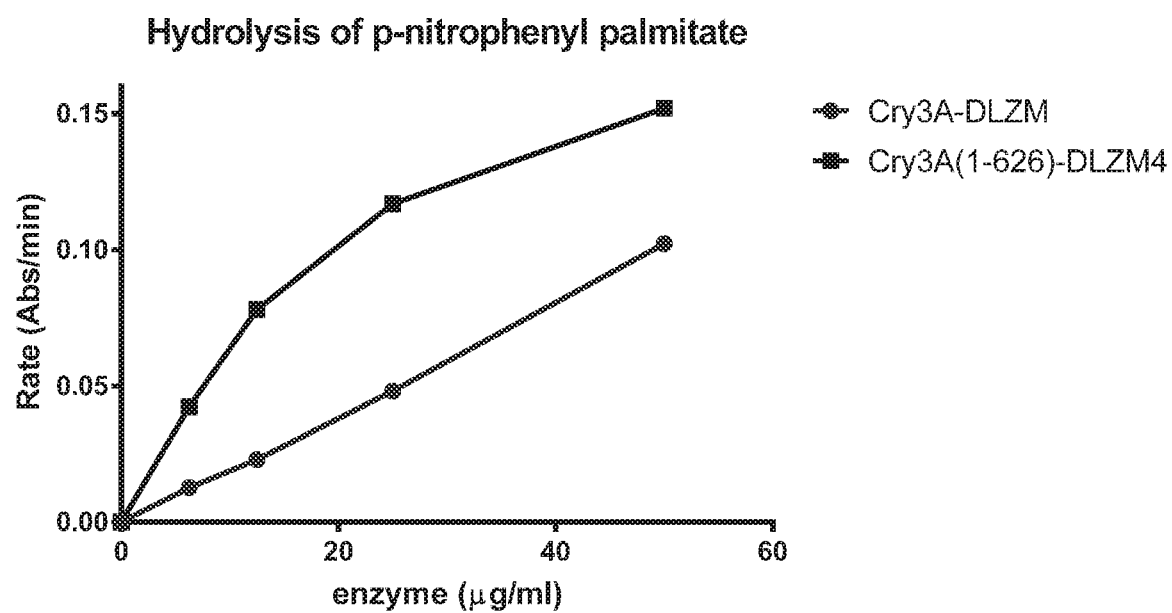
Figure 37:
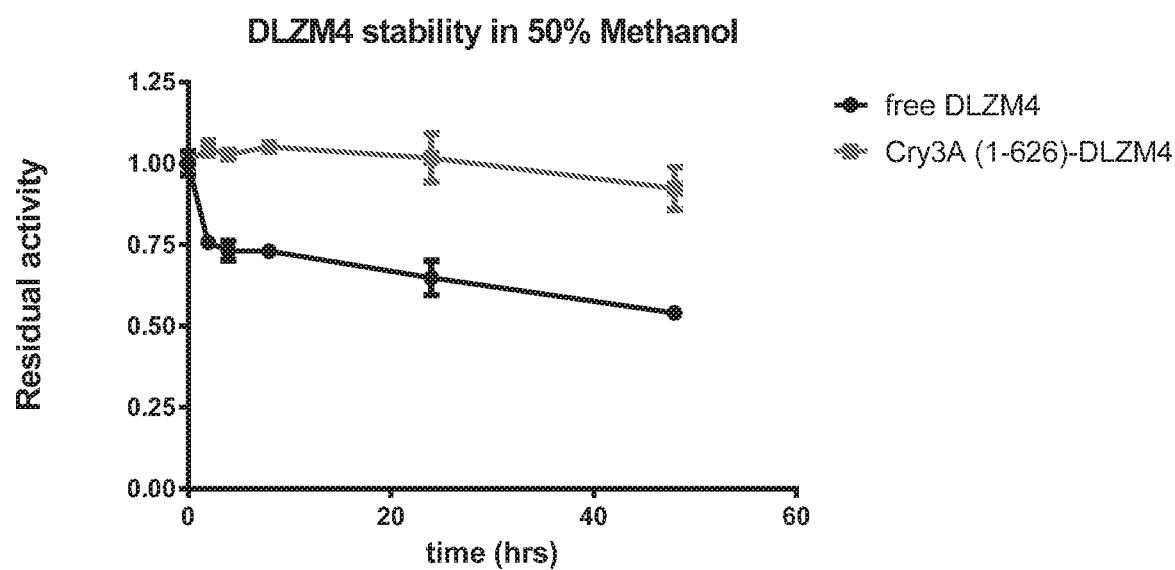
Figure 38:
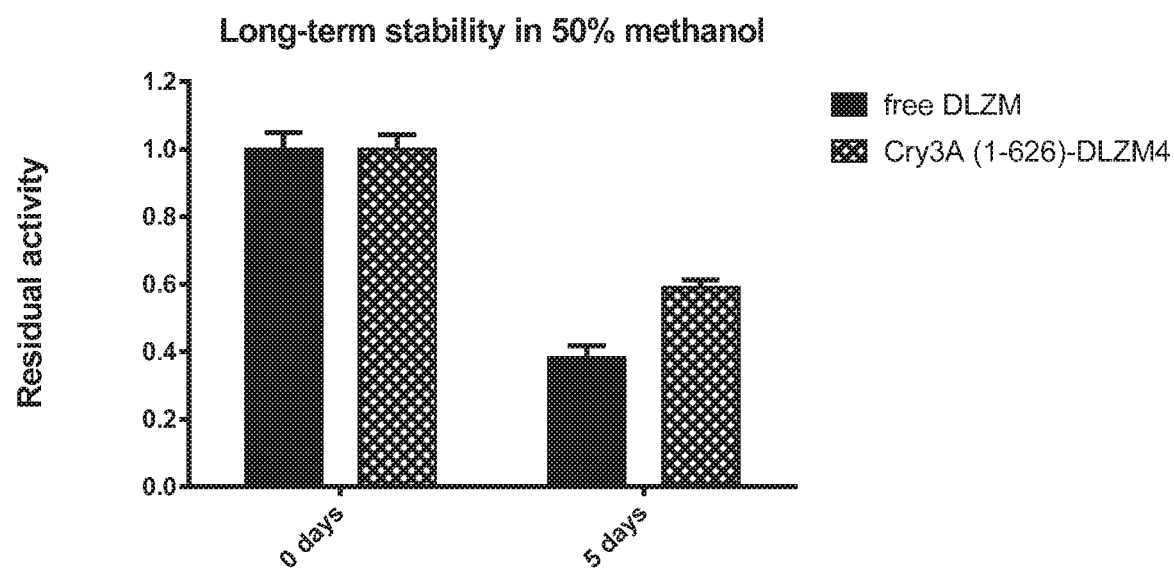
Figure 39:
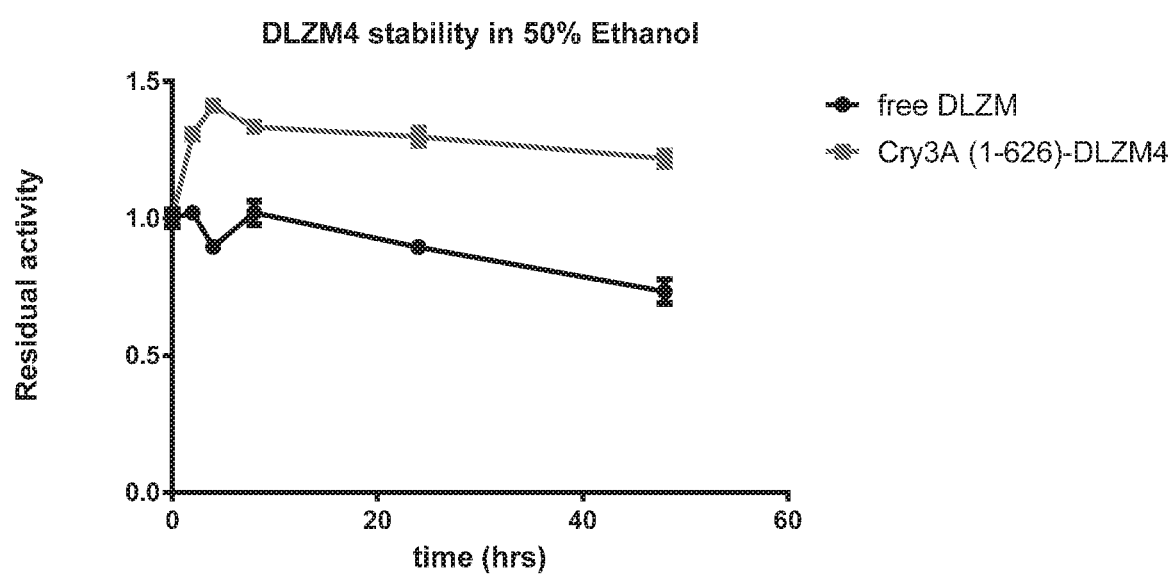
Figure 40:
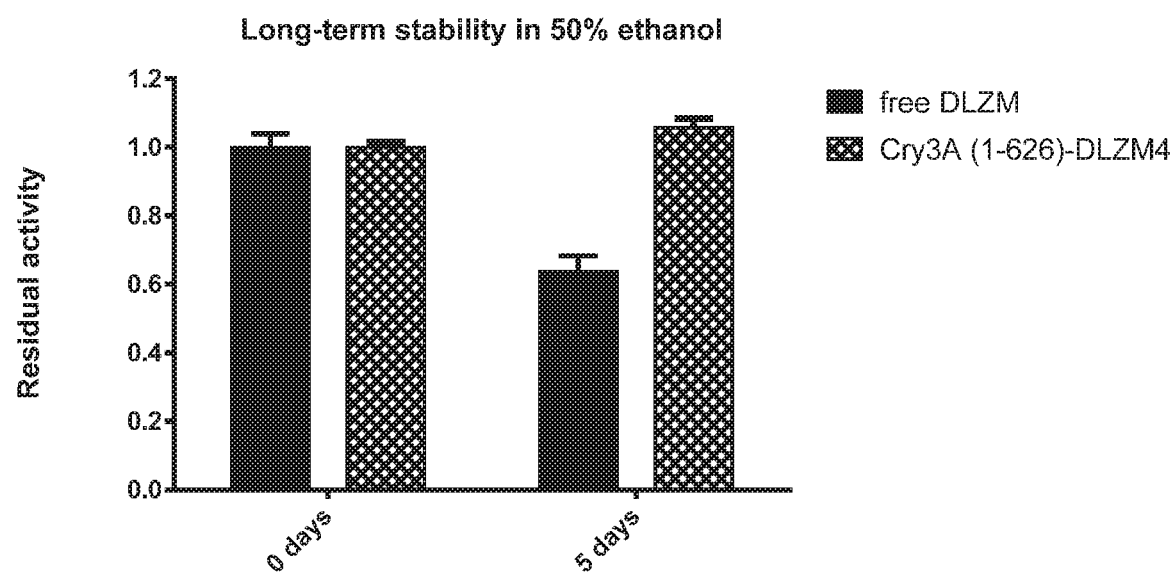
Figure 41:
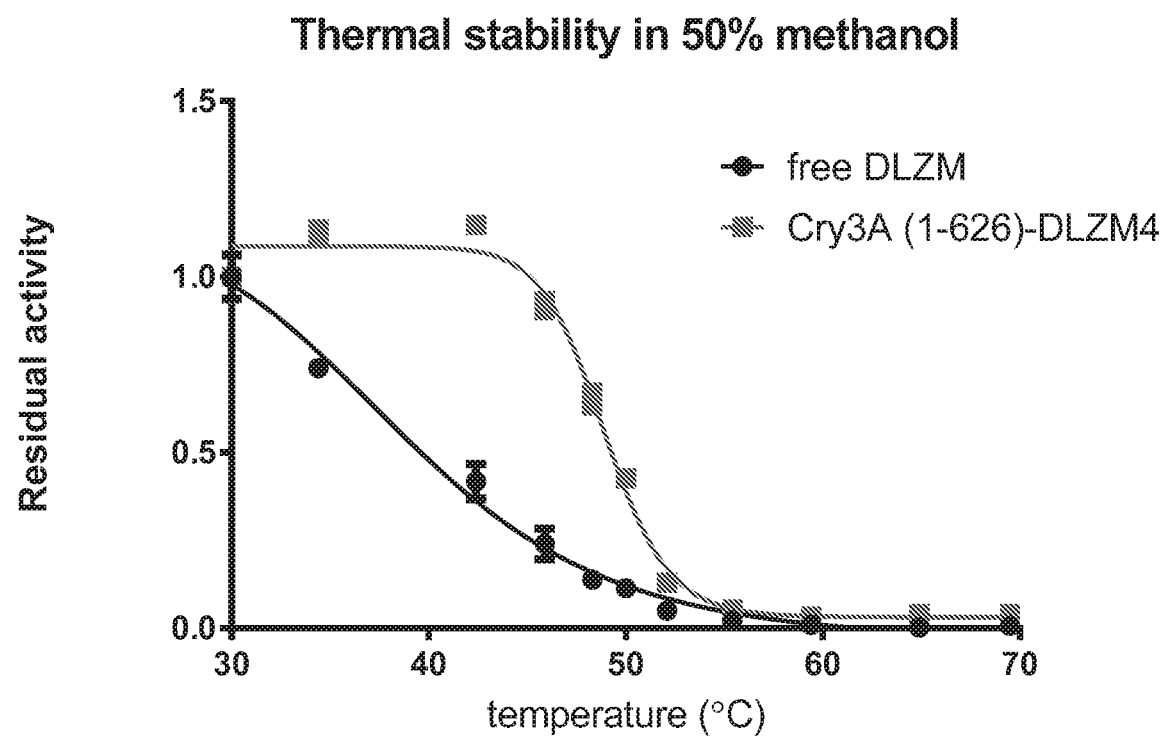
Figure 42:
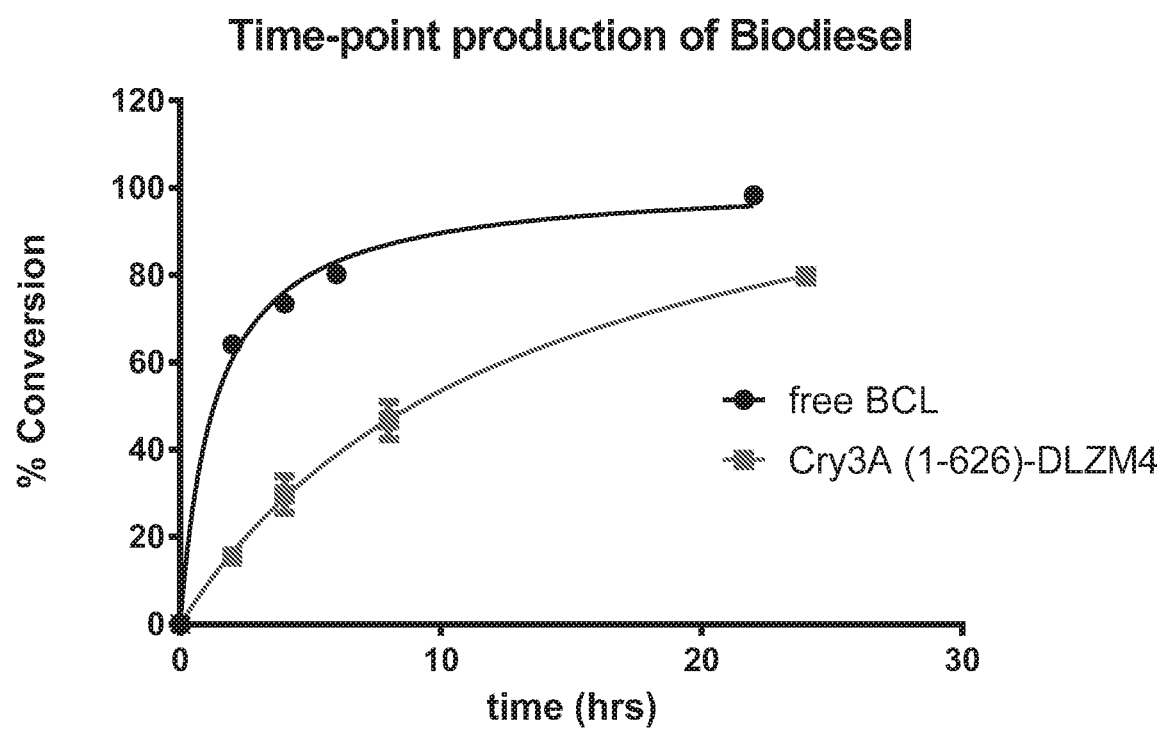
Figure 43:
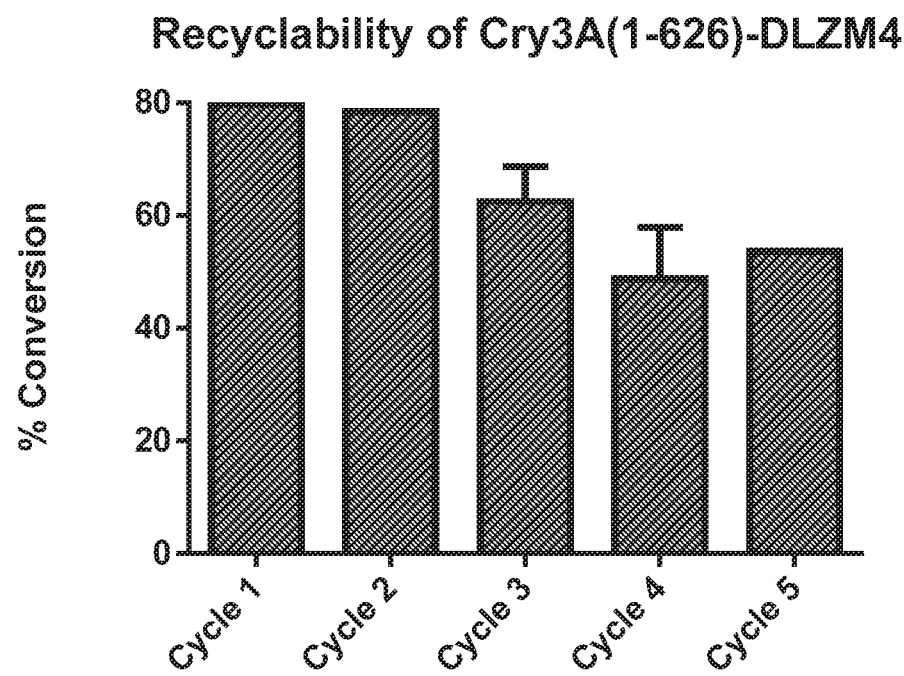
Figure 44:
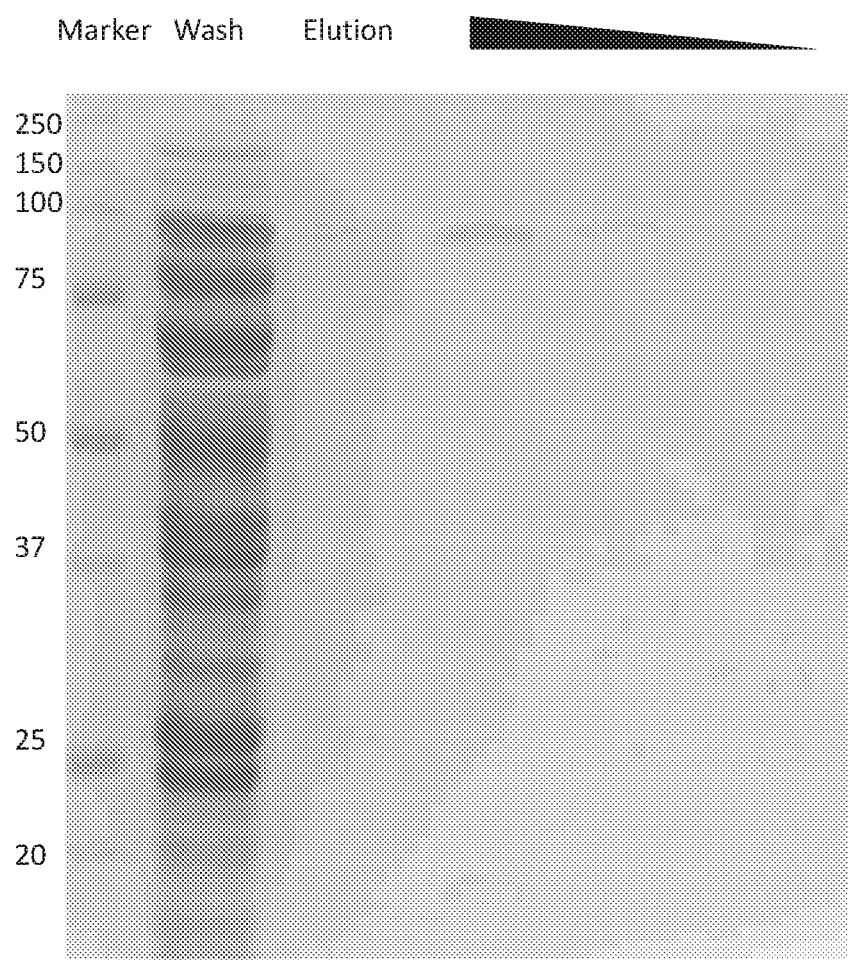
Figure 45:
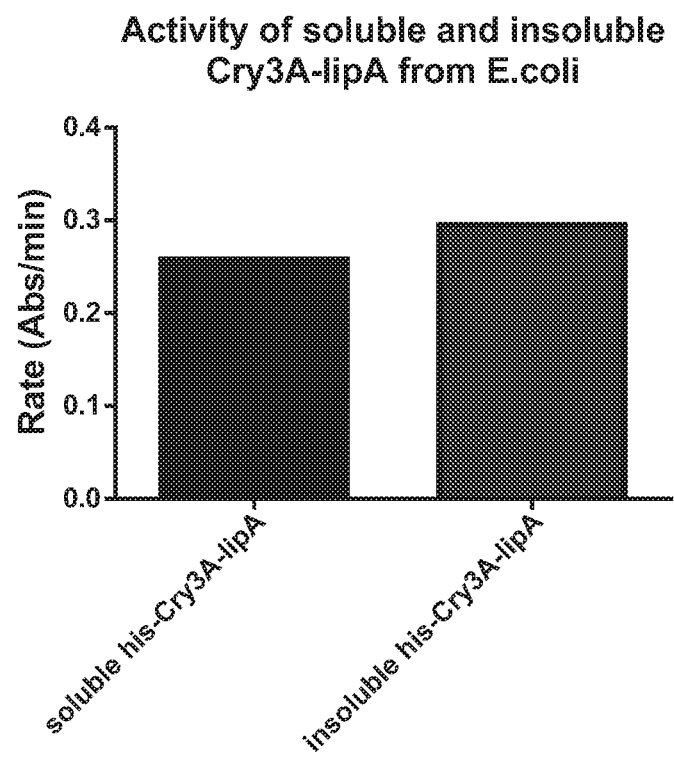

Exploring the Ability of Cry3Aa Crystal Immobilization to Enhance the Organic Solvent Stability of Pre-Evolved Biodiesel Lipases Directed evolution can produce very stable enzymes, and in combination with immobilization, can produce a biocatalyst with optimum industrial properties. In this last aim, it will be determined whether Cry3Aa-mediated immobilization of a pre-evolved enzyme can improve its stabilize and recyclability even further. Recently, PMlip has been evolved to be MeOH tolerant specifically for biodiesel production purposes (27). The evolved enzyme called Dieselzyme 4 (DLZM4) contains 13 mutations (FIG. 10) and outperforms the wild-type PMlip (WT) and the methanol tolerant *Burkolderia cepacia* lipase (BClip) (FIG. 11). It is expected that Cry3Aa-mediated immobilization of DLZM4 can further enhance its MeOH/EtOH tolerance and recyclability. To test this, the codon optimized PMlip gene will first be synthesized with the 13 mutations (FIG. 10) previously reported (27). After cloning this gene into a *E.coli* expression vector for free lipase and the Cry3Aa fusion expression vector the inventors have developed for the Cry3Aa-lipase fusion crystal, the free DLZM4 enzyme and Cry3Aa-DLZM4 crystals will be produced and purified. Immobilization of the free DLZM4 will be performed as described in the last section. Cry3Aa-DLZM4 and the oxirane-immobilized DLZM4 will then be incubated with canola oil and MeOH/EtOH, and the percent conversion over eight 20-h reaction cycles will be evaluated by GC. It is expected that the Cry3Aa immobilized DLZM4 will be further enhanced in its ability to convert canola oil to FAME over the 8 reaction cycles when compared to oxirane immobilized DLZM4. Previous studies havw shown that oxirane immobilized DLZM4 conversion drops below 80% after the second cycle (FIG. 11), it is expected that Cry3Aa-DLZM4 fusion crystals can maintain their 90-100% conversion rates into the third and fourth cycles.

Example 2: Esterase and Lipase Fusion Proteins

In this study, the present inventors successfully produced pnbA esterase crystals and lipA lipase crystals and demonstrated that both are more stable than the wild-type counterparts in organic solvents. Particularly, lipA lipase crystals are also more stable against thermal denaturation than the wild-type lipase.

Cry3A-pnbA Fusion Crystals

The first enzyme examined was p-nitrobenzyl esterase (pnbA) from *Bacillus subtilis* 168. This enzyme was chosen because the reaction is easy to monitor, its production in Bt is straightforward since it is a native *Bacillus* enzyme, and it has been widely used as a biocatalyst for antibiotic production. The enzyme crystals could be easily expressed in Bt and purified via density gradient separation and washing. The crystals were solubilized at pH 11.0 and analyzed on an SDS-PAGE gel to check for purity and size comparison (FIG. 12). In order to compare the stabilities of the crystal and soluble forms, the wild-type pnbA esterase was purified from *E. coli* using the pET-SUMO fusion system, generating native pnbA (FIG. 13).

Organic solvents can increase reaction rates by increasing substrate solubility, can enhance substrate specificity and promote production of various products. However, enzymes are unstable in many organic solvents, especially water miscible solvents, and therefore are inactive. Thus the inventors first sought out to reconcile whether Cry3A-pnbA crystals had higher reaction rates in water miscible organic solvents. Some of the most widely used water miscible organic solvents in organic reactions are acetonitrile (ACN) and ethanol (EtOH) thus the stabilities of both crystalline and soluble pnbA esterase in these two solvents were tested.

The substrate used for this reaction was 4-nitrophenol acetate. Upon hydrolysis this substrate forms the product 4-nitrophenol which absorbs light at 405 nm (FIG. 4).

Equivalent amounts of soluble and crystalline pnbA were subjected to increasing concentrations of organic solvent and the activities were monitored over a period of 10 minutes. In all organic solvents tested, the pnbA crystals have higher activity than the wild-type pnbA protein (FIG. 14). The largest difference in activity was in 20% ACN where the pnbA crystals retain 56% activity and the wild-type only retains 19% activity (FIG. 14*a*). As such, the enzyme kinetics at this particular concentration of ACN was determined. Equivalent amounts of enzymes were subjected to increasing concentrations of 4-nitrophenol acetate in 20% ACN. The kcat/Km for the crystalline pnbA is about 2.3 fold higher than the soluble enzyme, further demonstrating the higher catalytic efficiency of enzyme crystals in organic solvents over the soluble form (FIG. 15).

Cry3A-lipA Fusion Crystals Recyclability

An efficient biocatalyst should be able to be recycled and reused in subsequent reaction cycles while maintaining structural integrity and minimizing activity loss. To this end, the recyclability with the Cry3A crystals fused to the lipase A and pnbA enzymes was tested. It has been shown that lipA retains a relatively high reaction rate over 4 cycles (FIG. 16). However, Cry3A-pnbA activity is lost drastically over the 4 reaction cycles.

One likely possibility for the reduction of activity after multiple reaction cycles could be due solubilization of the crystals during the reaction and wash steps. Normally, Cry3A solubilizes at alkaline pH (10-11), but it has been found that some Cry3A-pnbA solubilizes at neutral pH. To reduce the solubilization and thus increase the recyclability, lipA crystals were crosslinked with 1% glutaraldehyde, which should hold the Cry monomers together. It was shown that, after crosslinking the lipA crystals, solubilization of the crystals at pH 11 was almost completely abolished (FIG. 17). For Cry3A-pnbA crystals bis(sulfosuccinimidyl)suberate (BS3) was used as the cross-linker, which prevented solubilization of Cry3A-pnbA crystals (FIG. 18). In both cases nearly 100% of the enzymes activity was retained (data not shown).

Next, it was evaluated whether crosslinking could improve recyclability. As expected, crosslinking was shown to improve the recyclability of both enzymes, especially the more fragile Cry3A-pnbA enzyme (FIG. 19).

Organic Solvent Tolerance of Crosslinked Crystals

Since the recyclability of both enzyme crystals was improved after cross-linking, it was then investigated whether the solvent stability of the cross-linked crystals was affected. The free enzyme and cross-linked Cry3A-enzymes were incubated with increasing amounts of ACN or EtOH. In both cases, cross-linked Cry3A-pnbA crystals (FIG. 20) and cross-linked Cry3A-lipA crystals (FIG. 21) were much more active in ACN or EtOH than the free enzymes respectively. These data demonstrate that cross-linking does not affect organic solvent stability, and in fact, may strengthen the tolerance.

Other Hydrolytic Enzymes

Another hydrolytic enzyme was fused to Cry3A to determine if this technology could be expanded to more than simples esterases. Peptide deformylase (PDF) is an enzyme that cleaves off the formyl group from the N terminal methionine, and can be used as a deprotection agent in peptide synthesis. The PDF from *Borrelia burgdorferi* was chosen for this study because it adopts $Zn^{2+}$ as the catalytic metal as opposed to the more easily oxidized $Fe^{2+}$ employed by many other PDFs (28). As illustrated in (FIG. 22), Cry3A-PDF is more active in both ACN and EtOH than free PDF, supporting that the Cry3A framework can extend organic solvent tolerance to other enzymes.

Truncation of Cry3A

The inventors investigated the extent of truncation of Cry3Aa in the Cry3Aa fusion, which would still yield active and stable crystals. Cry3Aa is 644 amino acids long and contains 3 separately folded domains. They have previously demonstrated that domain I of Cry3A, the N-terminal 290 amino acids, while fused to GFP formed green fluorescent crystals. In this study, the lipA gene was fused to domain I of Cry3Aa (Cry3Aa (1-290)-lipA) and expressed in *Bt* and then the crystals were purified. The crystals were solubilized at pH 11.0 and ran on an SDS-PAGE gel to show the intact fusion at the correct size (FIG. 23). These crystals were more active in terms of Units/mg than the full length Cry3Aa-lipA fusion crystals, and were similarly stable. Like Cry3Aa-lipA, Cry3Aa (1-290)-lipA activity in ACN and EtOH was much higher than free lipA (FIG. 24), and Cry3Aa (1-290)-lipA was much more stable in ACN than free lipA over the long incubation period (FIG. 25). Furthermore, Cry3Aa (1-290)-lipA was also more thermostable than free lipA (FIG. 26). These data clearly illustrate that full length Cry3Aa is not necessary to successfully immobilize and stabilize the enzyme fusion, at least in the case of lipA protein. Since domain I of Cry3Aa fused to lipA yielded stable and active crystals, it was hypothesized that lipA fusion to other domains of Cry3A may give similar results. Therefore, several Cry3A truncation-lipA fusion constructs were made outlined in (FIG. 27). Scanning electron microscopy revealed that all constructs form uniform crystals of similar size (FIG. 28). All constructs were active against the substrate 4npA, and in terms of units/mg Cry3A (495-644)-lipA had the highest activity (FIG. 29). To determine if these truncated Cry3A-lipA fusions retained their stability the thermal stability of each was measured. Except for Cry3A (1-301)-lipA-Cry3A(495-644), all constructs were more stable than free lipA with $T_m$ values 5-8° C. higher than free lipA (FIG. 30).

Further Characterization of Cry3A(1-626)-lipA

In terms of moles lipA, Cry(1-626)-lipA was among the most active truncated fusion constructs, the inventors thus set out to further characterize the organic solvent tolerance of this species. Cry(1-626)-lipA was much more active in ACN and EtOH than free lipA (FIG. 31) as well as exhibited enhanced long-term stability in various organic solvents (FIG. 32). Intriguingly, Cry3A(1-626)-lipA was more thermal stable than his-lipA aggregates supporting the notion that a well ordered packing is required to promote stability (FIG. 33). However, when Cry3A(1-626)-lipA was solubilized at pH 11 and subsequently used in the thermal stability experiments all stability was lost (FIG. 34), highlighting the fact that it is the crystalline nature of Cry3A(1-626)-lipA that promotes stability.

Cry3Aa(1-626)-lipA Synthesis of Biodiesel

Lipases are popular enzymes used to make biodiesel. In order to compete with chemical catalysis good recyclability of immobilized lipases is key. We tested the recyclability of Cry3Aa(1-626)-lipA in the synthesis of biodiesel from coconut oil and methanol over 5 reaction cycles. We tested two different enzyme loadings: 1.0% catalyst and 2.5% catalyst w/w of oil. The former is the minimum amount need to reach 100% and the latter is an amount more consistent with current % catalyst in the literature. Each cycle reaction contains 3:1 methanol:coconut oil, 30% water, and done at 2,000 rpm, 30° C. for 48 hours. The samples were subjected to gas chromatography (GC) and the % conversion was calculated by comparing to a 48 hour BCL reaction set as 100%. As displayed in (FIG. 35), Cry3Aa(1-626)-lipA retains over 70% conversion and 94% conversion after 5 cycles for 1.0% and 2.5% w/w catalyst respectively.

Another Enzyme for the Production of Biodiesel

One potential application of using the Cry3A fusion crystals of this invention is the production of alternative fuels such as biodiesel. An enzyme was recently evolved for this purpose, termed Dieselzyme 4 (DLZM4). The inventors fused this enzyme to a truncated form of Cry3A(1-626) (Cry3A(1-626)-DLZM4) and evaluated its organic solvent stability compared to the free enzyme. This truncated form of Cry3A was used because it has been found to give a 4-fold higher activity compared to the full length Cry3A-DLZM4 (FIG. 36). A flexible linker was included and the C terminal 18 residues of Cry3A was deleted to improve the flexibility of DLZM4 inside the crystal, which resulted in higher activity.

The long-term organic solvent stability was evaluated in the solvents methanol (MeOH) and ethanol (EtOH), which can both be used as substrates for biodiesel production. As shown in (FIGS. 37-40), Cry3A(1-626)-DLZM4 is more stable in both solvents up to 5 days.

In addition, it was found that the Cry3A(1-626)-DLZM4 crystals were more resistant to heat while incubated in 50% MeOH (FIG. 41). Future studies will examine the long-term thermal stability of the Cry3A(1-626)-DLZM4 fusion crystals as well as its recyclability when used for producing biodiesel from canola oil and MeoH/EtOH.

Cry3A(1-626)-DLZM4 Synthesis of Biodiesel

The inventors next sought to determine whether Cry3A (1-626)-DLZM4 crystals could produce biodiesel. The use of Dieselzyme 4 (DLZM) is described in, e.g., international patent application number PCT/US2013/067348, published as WO2014/074352. For the synthesis reaction 0.282 ml of canola oil was mixed with 0.118 ml of a 1:1 MeOH: 0.1M sodium phosphate solution and 1.8 mg of Cry3A*-DLZM. This corresponds to a 5:1 MeOH:oil w/w ratio in 25% water. As a positive control, a large excess of free *Burkholderia cepacia* lipase (BCL) was used in the same conditions (9). At 0, 2, 4, 8, 24 hours 10 μl of the oil layer was extracted and mixed with 0.3 ml of n-hexane spiked with methyl-heptadecanoate as the internal standard. The samples were subjected to gas chromatography (GC) and the % conversion was calculated by comparing to a 48 hour BCL reaction set as 100%. After 24 hours using 1.8 mg Cry3A(1-626)-DLZM4 the yield reached 80% biodiesel (FIG. 42). Cry3A (1-626)-DLZM4 continued to produce biodiesel to at least 50% yield over five 24 hour reaction cycles (FIG. 43).

All patents, patent applications, and other publications, including GenBank Accession Numbers, cited in this application are incorporated by reference in the entirety for all purposes.

REFERENCES (1) K. Drauz and H. Waldmann, Enzyme catalysis in organic synthesis, *Wiley-VCH,* Weinheim, 2002.
(2) M. Kaieda, Samukawa, A. Kondo, and H. Fukuda, *J Biosci Bioeng,* 2001, 91, 12-15.
(3) F. Cedrone, A. Meneze and E. Quemeneur, *Curr Opin Struct Biol,* 2000, 10, 405-410.
(4) L. Giver, A. Gershenson, P. Freskgard, and F. H. Arnold, *Proc Natl Acad Sci USA,* 1998, 95, 12809-12813.
(5) F. H. Arnold, *FASEB J,* 1993, 7, 744-749.
(6) N. Zhang, W. C. Suen, W. Windsor, L. Xiao, V. Madison, A. Zaks, *Protein Eng,* 2003, 16, 599-605.
(7) K. Chen and F. H. Arnold, *Proc Natl Acad Sci USA,* 1993, 90, 5618-5622.
(8) R. A. Sheldon and S. van Pelt, *Chem Soc Rev,* 2013, 42, 6223-6235.
(9) V. A. Martins Dos Santon, E. J. Leenen, M. M. Rippoll, C. van der Sluis, T. van Vliet, J. Tramper and R. H. Wijffels, *Biotechnol Bioeng,* 1997, 56, 517-29.
(10) L. Cao, L. van Langeny and R. A. Sheldon, *Curr Opin Biotechnol,* 2003, 14, 387-394.
(11) F. A. Quiocho and F. M. Richards, *Proc Natl Acad Sci USA,* 1964, 52, 833-839.
(12) A. L. Margolin, *Trends Biotechnol,* 1996, 14, 223-230.
(13) J. Lalonde, *Chem Tech,* 1997, 27, 38-45.
(14) L. Cao, F. van Rantwijk and R. A. Sheldon, *Org Lett,* 2000, 2, 1361-1364.
(15) S. Talekar, A. Joshi, G. Joshi, P. Kamat, R. Haripurkar and S. Kambale, *RSC Advances,* 2013, 3, 12485-12511.
(16) H. W. Park, B. Ge, L. S. Bauer and B. A. Federici, *Appl Environ Microbiol,* 1998, 64, 3932-3938.
(17) E. Schnepf, N. Crickmore, J. Van Rie, D. Lereclus, J. Baum, J. Feitelson, D. R. Zeigler and D. H. Dean, *Microbiol Mol Biol Rev,* 1998, 62, 775-806.
(18) H. R Whiteley and H. E. Schnepf, i Annu Rev Microbiol, 1986, 40, 549-576.
(19) M. S. Nair, M. M. Lee, A. Bonnegarde-Bernard, J. A. Wallace, D. H. Dean, M. C. Ostrowski, R. W. Burry, P. N. Boyaka and M. K. Chan, *PLoS One,* 2015, 10, e0127669.
(20) K. E. Jaeger and T. Eggert, *Curr Opin. Biotechnol,* 2002, 13, 390-397.
(21) A. Liese and S. Lütz, In: Ullmann's encyclopedia of industrial chemistry, electronic release. 7th edition. *Wiley-VCH,* Weinheim, 2004.
(22) K. Buchholz, V. Kasche, and U. T. Bornscheuer, Biocatalysts and enzyme technology. *Wiley-VCH* Weinheim, 2005.
(23) J. Detry, T. Rosenbaum, S. Lütz , D. Hahn, K. E. Jaeger, M. Müller, and T. Eggert, *Appl Microbiol Biotechnol,* 2006, 72, 1107-16.
(24) K. Blank, J. Morfill, H. Gumpp, and H. E. Gaub. *J Biotechnol,* 2006, 125, 474-483.
(25) M. G. Jang, D. K. Kim, S. C. Park, J. S. Lee, and S. W. Kim. *Renewable Energy,* 2012, 42, 99e104.
(26) C. Luna, C. Verdugo, E. D. Sancho, D. Luna, J. Calero, A. Posadillo, F. M. Bautista and A. A. Romero. *Bioresources Bioprocessing,* 2014, 1:11.
(27) T. P Korman, B. Sahachartsiri, D. M. Charbonneau, G. L Huang, M. Beauregard and J. U. Bowie. *Biotechnol Biofuels,* 2013, 6:70.
(28) K. T. Nguyen, J. C. Wu, J. A. Boylan, F. C. Gherardini, D. Pei, *Arch Biochem Biophys,* 2007, 2, 217-25.

What is claimed is:

1. A fusion protein comprising:
   (1) an enzyme;
   (2) a Cry3Aa protein fragment consisting of residues 1-290, 1-301, or 1-626 of the amino acid sequence of SEQ ID NO: 4; and
   (3) optionally an additional amino acid sequence of no more than 50 amino acids,
   wherein the fusion protein forms a crystal upon being expressed in a host cell and has enzyme activity while in crystal form.

2. The fusion protein of claim 1, wherein the enzyme is an esterase, a lipase, or a peptide deformylase.

3. The fusion protein of claim 2, wherein the esterase is p-nitrobenzyl esterase (pnbA).

4. The fusion protein of claim 2, wherein the lipase is a *Candida antarctica* (*Ca*) lipase, *Proteus mirabilis* (*Pm*) lipase, or Dieselzyme (DLZM).

5. The fusion protein of claim 1, which is crystalized and crosslinked.

6. The fusion protein of claim 1, wherein the fusion protein comprises a hydrolase at the C-terminus and the Cry3Aa protein fragment at the N-terminus, optionally with a peptide linker present between the hydrolase and the Cry3Aa protein fragment.

7. A composition comprising the fusion protein of claim 1 and a substrate to the enzyme.

8. The composition of claim 7, wherein the fusion protein is crystalized and/or chemically crosslinked.

9. The composition of claim 7, further comprising a solid support, wherein the fusion protein is immobilized on the solid support.

10. A method of performing a reaction, comprising the step of incubating the fusion protein of claim 1 with a substrate to the enzyme under conditions permissible for the substrate to be catalyzed by the enzyme.

11. The method of claim 10, wherein the fusion protein is immobilized on a solid support.

12. The method of claim 10, further comprising, after the reaction is completed, removing the reaction product and reusing the fusion protein in a second reaction.

* * * * *